US009364542B2

(12) United States Patent
Chang

(10) Patent No.: US 9,364,542 B2
(45) Date of Patent: Jun. 14, 2016

(54) PROTEIN FORMULATIONS CONTAINING AMINO ACIDS

(71) Applicant: Byeong Seon Chang, Sherman Oaks, CA (US)

(72) Inventor: Byeong Seon Chang, Sherman Oaks, CA (US)

(73) Assignee: Excelse Bio, Inc., Thousand Oaks, CA (US)

( * ) Notice: Subject to any disclaimer, the term of this patent is extended or adjusted under 35 U.S.C. 154(b) by 68 days.

(21) Appl. No.: 13/662,281

(22) Filed: Oct. 26, 2012

(65) Prior Publication Data

US 2014/0127227 A1    May 8, 2014

Related U.S. Application Data

(60) Provisional application No. 61/552,688, filed on Oct. 28, 2011.

(51) Int. Cl.

| | |
|---|---|
| *A61K 47/18* | (2006.01) |
| *C07K 16/28* | (2006.01) |
| *C07K 16/10* | (2006.01) |
| *A61K 38/48* | (2006.01) |
| *A61K 38/57* | (2006.01) |
| *A61K 38/47* | (2006.01) |
| *C07K 16/24* | (2006.01) |
| *C07K 16/22* | (2006.01) |
| *A61K 39/395* | (2006.01) |
| *C07K 16/32* | (2006.01) |

(52) U.S. Cl.
CPC .............. *A61K 47/183* (2013.01); *A61K 38/47* (2013.01); *A61K 38/4846* (2013.01); *A61K 38/57* (2013.01); *A61K 39/39591* (2013.01); *C07K 16/1027* (2013.01); *C07K 16/22* (2013.01); *C07K 16/241* (2013.01); *C07K 16/2863* (2013.01); *C07K 16/2866* (2013.01); *C07K 16/2887* (2013.01); *C07K 16/32* (2013.01)

(58) Field of Classification Search
None
See application file for complete search history.

(56) References Cited

U.S. PATENT DOCUMENTS

| | | | |
|---|---|---|---|
| 5,358,708 A | 10/1994 | Patel | |
| 6,525,102 B1 | 2/2003 | Chen et al. | |
| 7,666,413 B2 | 2/2010 | Liu et al. | |
| 7,767,644 B2 | 8/2010 | Schumann et al. | |
| 2003/0104996 A1 | 6/2003 | Li et al. | |
| 2003/0190316 A1 | 10/2003 | Kakuta et al. | |
| 2004/0022792 A1 | 2/2004 | Klimke et al. | |
| 2007/0053900 A1 | 3/2007 | Liu et al. | |
| 2008/0071063 A1 * | 3/2008 | Allan et al. | ................ 530/387.1 |
| 2008/0213282 A1 | 9/2008 | Jacob et al. | |
| 2009/0280129 A1 | 11/2009 | Liu et al. | |
| 2009/0291076 A1 * | 11/2009 | Morichika et al. | ......... 424/133.1 |
| 2010/0285011 A1 | 11/2010 | Morichika et al. | |
| 2012/0064086 A1 | 3/2012 | Liu et al. | |

FOREIGN PATENT DOCUMENTS

| | | |
|---|---|---|
| EP | 1491208 A1 | 12/2004 |
| EP | 1532983 A1 | 5/2005 |
| EP | 1977763 A1 | 10/2008 |
| EP | 1599222 B1 | 3/2009 |
| WO | 9629989 A1 | 10/1996 |
| WO | 2004062689 A1 | 7/2004 |
| WO | 2007109221 A2 | 9/2007 |
| WO | 2011095543 A1 | 8/2011 |
| WO | 2013063510 | 5/2013 |

OTHER PUBLICATIONS

"Recent U.S. Patents on Protein Drug Formulation: 2000-2007", by Hong Zhao and Elizabeth M. Topp, Recent Patents on Drug Delivery & Formulation 2008, 2, 200-208, Department of Pharmaceutical Chemistry, The University of Kansas, Recent Patents on Drug Delivery & Formulation, 2008, vol. 2, No. 3.

"Challenges in the development of high protein concentration formulations", Shire, et al., J. Pharma. Sci. 93(6): 1390-1402 (2004).

* cited by examiner

*Primary Examiner* — Brian J Gangle
*Assistant Examiner* — Andrea McCollum
(74) *Attorney, Agent, or Firm* — One3 IP Management, P.C.; Annette S. Parent; Dean G. Stathakis

(57) ABSTRACT

Provided are stable protein formulations that contain at least one amino acid. In certain embodiments, amino acid combinations either at least two, or three, or four, or more amino acids are included. By virtue of inclusion of the amino acids, the formulation has low viscosity and a protein in the formulations is physically, chemically, and biological stable even at high concentrations. In further embodiments, by virtue of inclusion of the amino acids, a protein in the formulations is physically, chemically, and biological stable even at high concentrations.

22 Claims, 20 Drawing Sheets

PROTEIN FORMULATIONS CONTAINING AMINO ACIDS

PRIORITY CLAIM

This US Non-Provisional patent application claims priority pursuant to 35 U.S.C. §119(e) to U.S. Provisional patent application 61/552,688, filed on Oct. 28, 2011, the contents of which is hereby incorporated by reference in its entirety.

FIELD OF INVENTION

This invention relates generally to stable protein formulations and their preparation and uses.

BACKGROUND

Pharmaceutical proteins and polypeptides, among other biopharmaceuticals, pose formulation challenges that can be intractable. Pharmaceutical proteins often cannot be administered orally, because they are degraded by the digestive process. Transdermal administration also generally is not suitable for proteins, because they are too large to pass through the skin effectively. Pulmonary delivery has been developed to the extent that one insulin product has been introduced to the market, but with limited success.

Consequently, pharmaceutical proteins typically are administered by injection; but, there are problems in formulating proteins for injection as well. Proteins in conventional solutions generally are unstable. They are prone to degradation, such as deamidation, aggregation and precipitation, from both chemical and physical processes. Aggregation, precipitation, and viscosity are particularly problematic for most proteins, especially at high protein concentrations. Proteins generally are more stable when lyophilized than they are in solution. However, inconvenience and patient compliance limit the successful marketing of lyophilized drug products and the preference for liquid formulations.

Proteins often cannot be formulated at sufficiently high concentrations for injection of effective amounts. In cases where the solubility and/or stability of the protein is limited, products are formulated at lower concentrations and delivered by intravenous infusion. However, high concentration protein-based medicines are desired by both patients and manufacturers. One reason is that is allows smaller volumes of liquid to be administered to an individual. Nevertheless, increasing the protein concentration may result in deleterious effects. The goal of high concentration and lyophilization has been elusive, in part because of deleterious viscoelastic and other properties occurring as concentration increases. Increased concentration sometimes, for instance, increases the tendency to aggregate or form gels, as well as increases the difficulty in administering these solutions through standard subcutaneous syringe and needle configurations.

In one example, antibody and antibody-like therapeutics are inherently difficult to concentrate, likely due in part to the nature of their complementarity determining regions ("CDRs," further discussed below). And yet, for therapeutic applications, antibody compositions at concentrations above 100 mg/ml or even 200 mg/ml are desirable. Similarly, high concentrations of other proteins commonly used to treat individuals is also desirable, for instance, for those individuals administered proteins either intravenously or subcutaneously.

Developing acceptable protein formulations is particularly challenging at high concentrations, such as those required for injection. Presently, a variety of proteins cannot be stably formulated at high concentrations in solution. Even for those that have been formulated in solution at relatively high concentrations, the solutions are not stable, suffering from aggregation or precipitation, and are too viscous for injection. Consequently, there are many proteins that suffer from suboptimal formulations or cannot be formulated advantageously for injection at all.

There is, therefore, a need for methods to make improved protein formulations, and for the formulations themselves. In one aspect, there is a need for protein formulations that are stable and have low viscosity. In another aspect, there is a need for protein formulations that are stable and have low viscosity for a protein therapeutic formulation at a high protein concentration for administration. In a further aspect, there is a need for formulations that are stable and have low viscosity for a liquid protein therapeutic formulation at a high protein concentration for administration by injection. Also, there is a need for better systematic methods to develop such formulations.

SUMMARY

It has now been discovered that inclusion of one, two, or more, different amino acids in a protein formulation improves the stability of the protein, even at high concentrations at which the protein is typically not stable in conventional formulations. While not wanting to be bound by any theory, it is believed that the amino acids limit deleterious viscoelastic effects and enhance the stability of the protein.

Again, while not wanting to be bound by any theory, it is contemplated that, when two more amino acids are included in a protein formulation, the amino acid combination may reversibly antagonize or block protein regions that are involved in protein-protein interactions, thereby competitively inhibiting such protein-protein contact and improving protein stability as well as reducing viscosity in the formulation.

The experimental examples below demonstrate that the use of amino acids in protein formulations permits retaining viscoelastic properties found in dilute solution, without resorting to modifying the protein structure itself. Therefore, protein formulations prepared with the present technology are stable even when the protein concentration is greater than about 130 mg/ml, 200 mg/ml or even higher, without deleterious viscoelastic effect or compromised stability.

Also described herein are processes for screening for suitable amino acid and amino acid combinations that improve the stability of protein formulations, using high throughput screening protocol based on relevant physical or biochemical markers.

Thus, one embodiment provides a stable pharmaceutical formulation comprising a protein and an amino acid. In some aspects, the amino acid is not H, R or M.

Another embodiment provides a stable pharmaceutical formation comprising a protein and two different amino acids. In one aspect, the two different amino acids are not H or R.

In one aspect, at least one of the two different amino acids contains a positively charged side chain. In another aspect, at least one of the two different amino acids contains a negatively charged side chain. In another aspect, at least one of the two different amino acids contains a hydrophobic side chain. In yet another aspect, at least one of the two different amino acids contains a polar uncharged side chain. In other aspects, these types of amino acids are used in any possible permutation and combination.

In one aspect, one of the two different amino acids contains a polar uncharged side chain and the other contains a hydrophobic side chain. In another aspect, one of the two different amino acids contains a polar uncharged side chain and the other is selected from the group consisting of G and P.

Likewise, stable protein formulations that comprise one or more proteins and two or more different amino acids are also provided. In certain aspects, the formulation contains three, four, five, six, seven, eight, nine, ten or even more different amino acids.

In any of the above embodiments, the concentration of each of the amino acids may be at least, for instance, about 0.1 mg/ml. In any aspects, the one or more proteins each may be present at a concentration of at least about 100 mg/mL.

Proteins formulated in the formulations described herein can be selected from the group consisting of an enzyme, a cytokine, a neurotropic factor, an antibody, a peptide, a hormone, a DNA-binding protein, an aptamer, erythropoietin (EPO), human insulin, interferon-α (Intron A), granulocyte-colony stimulating factor (G-CSF), human growth hormone, interferon-R, recombinant hepatitis B vaccine, glucocerobrosidase, agalsidase, imiglucerase, α-galactosidase A, and tissue plasminogen activator (tPA).

In one aspect, the protein is an antibody, such as but limited to, ranibizumab, bevacizumab, cetuximab, infliximab, palivizumab, abciximab, alemtuzumab, altumomab pentetate, atlizumab, basiliximab, daclizumab, eculizumab, muromonab-CD3, natalizumab, ofatumumab, panitumumab, rituximab, tocilizumab, and trastuzumab.

Further, methods of preparing and using the stable protein formulations are also provided.

SUMMARY OF THE INVENTION

Aspects of the present invention disclose a stable pharmaceutical formation comprising one or more amino acids to stabilize a protein in the pharmaceutical formulation and one or more amino acids to reduce the viscosity of the pharmaceutical formulation. Further aspects of the present invention disclose a formulation wherein a first amino acid stabilizes the protein and a second different amino acid reduces the viscosity of the protein solution or, wherein the same amino acid stabilizes the protein and reduces the viscosity of the protein solution.

Aspects of the present invention disclose a stable pharmaceutical formulation, wherein the pharmaceutical formulation comprises two or more different amino acids to stabilize protein. Further aspects of the present invention disclose a stable pharmaceutical formulation, wherein the pharmaceutical formulation comprises two or more amino different acids to reduce the viscosity of the pharmaceutical formulation. Additional aspects of the present invention disclose a pharmaceutical formulation that comprises two or more different amino acids to stabilize a protein in the pharmaceutical formulation and two or more different amino acids to reduce the viscosity of the pharmaceutical formulation, wherein the two or more different amino acids to stabilize a protein in the pharmaceutical formulation are the same as the two or more different amino acids to reduce the viscosity of the pharmaceutical formulation or, wherein the pharmaceutical formulation comprises two or more different amino acids to stabilize a protein in the pharmaceutical formulation and two or more different amino acids to reduce the viscosity of the pharmaceutical formulation, wherein the two or more different amino acids to stabilize a protein in the pharmaceutical formulation are not the same as the two or more different amino acids Aspects of the present invention disclose a pharmaceutical formulation, wherein, the amino acid to stabilize the protein is selected from G, S, T, A, R, M, K, P and N and the amino acid to reduce the viscosity of the formulation is Proline or Glycine. Further aspects of the present invention disclose a pharmaceutical formulation, wherein at least one of the amino acids: (i) contains a positively charged side chain, (ii) contains a negatively charged side chain, (iii) contains a hydrophobic side chain, or (iv) contains a polar uncharged side chain. Additional aspects of the present invention disclose a pharmaceutical formulation, wherein one of the two different amino acids: (i) contains a polar uncharged side chain and the one of the two different amino acids contains a hydrophobic side chain, (ii) contains a polar uncharged side chain and the other is selected from the group consisting of G and P. Further aspects of the present invention disclose a pharmaceutical formulation, wherein the one or more amino acids is selected from: (i) the group consisting of I, M, P, S, R, K, E, and N, and wherein each is present at a concentration of greater than about 0.1 mg/mL or (ii) the group consisting of S, T, N, G, A, K, F, V, L, H, I, and P, and wherein each is present at a concentration of greater than about 0.1 mg/mL.

Aspects of the present invention disclose a pharmaceutical formulation, wherein the protein is selected from the group consisting of an enzyme, a cytokine, a neurotropic factor, an antibody, a peptide, a hormone, a DNA-binding protein, vaccine, toxin or an aptamer.

Aspects of the present invention disclose a pharmaceutical formulation, wherein the antibody is selected from the group consisting of infliximab, bevacizumab, and ranibizumab, and at least one of the two different amino acids is selected from the group consisting of S, T, N, G, P, Q, V, P and A; wherein the antibody is cetuximab and at least one of the two different amino acids is selected from the group consisting of I, M, P, S, R, K, E, P and N; wherein the antibody is rituximab and at least one of the two different amino acids is selected from the group consisting of H, R, M, K, P and F; wherein the antibody is trastuzumab and at least one of the two different amino acids is selected from the group consisting of K, M, G, H, R, P and N.

Aspects of the present invention disclose a pharmaceutical formulation, wherein stability of a protein is determined by visual inspection, SDS-PAGE, IEF, size exclusion liquid chromatography (SEC-HPLC), reversed phase liquid chromatography (RP-HPLC), ion-exchange HPLC, capillary electrophoresis, light scattering, particle counting, turbidity, RFFIT, bioassays, and kappa/lambda ELISA.

Aspects of the present invention disclose a pharmaceutical formulation, wherein a protein is considered stable when the protein in formulation: (a) retains its physical stability; (b) retains its chemical stability; and/or (c) retains its biological activity. Further aspects of the present invention disclose a pharmaceutical formulation, wherein a protein retains its physical stability in a formulation when the protein in formulation: (a) does not aggregate; (b) does not precipitate; and, (c) does not denature. Additional aspects of the present invention disclose a pharmaceutical formulation, wherein the physical stability of a protein in a formulation is determined by: (a) visual examination of color and/or clarity; (b) UV light scattering; (c) size exclusion chromatography; and/or, (d) electrophoresis. Further aspects of the present invention disclose a pharmaceutical formulation, wherein the chemical stability of a protein in a formulation is determined by: (a) size exclusion chromatography; (b) SDS-PAGE; and/or, (c) matrix assisted laser desorption ionization/time of flight mass spectrometry.

Aspects of the present invention disclose a pharmaceutical formulation, wherein an amino acid contains a polar uncharged side chain and the other is selected from G and P; wherein the two different amino acids are selected from S, T, N, G, P and A. Further aspects of the present invention disclose a pharmaceutical formulation, further comprising a third different amino acid; further comprising a fourth different amino acid; wherein an amino acid contains a positively charged side chain and is selected from R, H and K; wherein an amino acid contains a positively charged side chain and is selected from R, H and K; wherein an amino acid contains a negatively charged side chain and is selected from D and E; wherein an amino acid contains a hydrophobic side chain and is selected from A, F, I, L, M, V, W and Y; wherein an amino acid contains a polar uncharged side chain and is selected from S, T, N and Q.

Aspects of the present invention disclose a pharmaceutical formulation, wherein an amino acid is selected from A, N, D, Q, E, I, L, K, F, S, T, W, Y and V; wherein the first amino acid is selected A and the second amino acid is selected from S, G, N, M, S, or T; wherein the first amino acid is F and the second amino acid is selected from S, G and T; wherein the first amino acid is G and the second amino acid is selected from A, F, M, N, Q, S and T; wherein the first amino acid is I and the second amino acid is selected from R and K; wherein the first amino acid is K and the second amino acid is selected from R, I, M and P; wherein the first amino acid is L and the second amino acid is S; wherein the first amino acid is M and the second amino acid is selected from A, G, K, N, R, S and T; wherein the first amino acid is N and the second amino acid is selected from A, G, M, Q, S, and T; wherein the first amino acid is P and the second amino acid is selected from K and R; wherein the first amino acid is Q and the second amino acid is selected from A, N, G, S, T and W; wherein the first amino acid is S and the second amino acid is selected from A, F, G, L, M, N, P, Q, R, T and V; wherein the first amino acid is T and the second amino acid is selected from A, F, G, M, N, QV, W and S; wherein the first amino acid is V and the second amino acid is selected from S, and T; wherein the first amino acid is W and the second amino acid is selected from H, Q and R; wherein the first amino acid is A and the second and the third amino acid are selected from F, G, L, M, N, Q, S, T and V; wherein the first amino acid is F and the second and the third amino acid are selected from A, G, S and T; wherein the first amino acid is G and the second and the third amino acid are selected from A, M, N, Q, S and T; wherein the first amino acid is I and the second and the third amino acid are selected from R and K; wherein the first amino acid is K and the second and the third amino acid are selected from R, I, M and P; wherein the first amino acid is A and the second and the third amino acid are selected from A, G, S and T; wherein the first amino acid is M and the second and the third amino acid are selected from A, G, K, N, R, S and T; wherein the first amino acid is N and the second and the third amino acid are selected from A, G, M, Q, S and T; wherein the first amino acid is P and the second and the third amino acid are selected from G, S, T, A, V, R, M, K, and N; wherein the first amino acid is Q and the second and the third amino acid are selected from A, N, G, S and T; wherein the first amino acid is R and the second and the third amino acid are selected from I, K, M, P, S and W; wherein the first amino acid is S and the second and the third amino acid are selected from A, F, G, L, N, P, Q, R, T, V and M; wherein the first amino acid is T and the second and the third amino acid are selected from A, F, G, M, N, Q, S and V; wherein the first amino acid is V and the second and the third amino acid are selected from A, S and T; wherein the first amino acid is W and the second and the third amino acid are selected from H, Q and R; wherein the pharmaceutical formulation comprises four amino acids; wherein the pharmaceutical formulation comprises five amino acids; wherein the pharmaceutical formulation comprises six amino acids; wherein the pharmaceutical formulation comprises one, two, three, four, five or six different amino acids and one or more bioactive agents.

Aspects of the present invention disclose a pharmaceutical formulation, wherein the pharmaceutical formulation comprises two or more different proteins. Further aspects of the present invention disclose a pharmaceutical formulation, wherein the two or more different proteins have a concentration of at least about 100 mg/ml, or is at least about 130 mg/ml, 150 mg/ml, 200 mg/ml, 250 mg/ml, 300 mg/mL or at least 400 mg/ml and is still stable as assessed by one or more of the methods discussed above.

Aspects of the present invention disclose a pharmaceutical formulation, wherein the one or more proteins are extended half-life or long acting forms of the protein; and further aspects, wherein the one or more proteins are linked to a water soluble polymer; and further aspects wherein the linkage is a releasable or stable linkage; and further aspects wherein the water soluble polymer is selected from a carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polyethylene glycol (PEG), branched PEG, POLYPEG®, polysialic acid (PSA), starch, hydroxyalkyl starch (HAS), hydroxylethyl starch (HES), polycarboxylate, polyvinylpyrrolidone, polyphosphazene, polyoxazoline, polyethylene-co-maleic acid anhydride, polystyrene-co-maleic acid anhydride, poly (1-hydroxymethylethylene hydroxymethylformal) (PHF), 2-methacryloyloxy-2'-ethyltrimethylammoniumphosphate (MPC).

Aspects of the present invention disclose a pharmaceutical formulation, wherein the concentration of a protein can be increased in the pharmaceutical formulation Further aspects, wherein the formulation comprises one or more excipients; and further wherein the one or more excipients are selected from buffers, tonicity modifiers, bulking agents, metal ions, chelating agents, surfactants, stabilizers, polymer, viscosity reducing agents, salts and carbohydrates.

Aspects of the present invention disclose a pharmaceutical formulation, wherein the formulation is administered to a patient orally, rectally, vaginally, parenterally, intrapulmonary, sublingually, pulmonarily and or intranasal. Aspects of the present invention disclose a pharmaceutical formulation, wherein the formulation is in the form of a sold or liquid; and further aspects, wherein the formulation is in the form of a tablet, a capsule, a gel tab, a lozenge, an orally dissolved strip, syrup, an oral suspension, an emulsion, a granule, a sprinkle and a pellet; and further asepcts wherein the formulation is a pharmaceutical composition comprising a bioactive agent formulated in a pharmaceutical formulation.

A kit comprising a bioactive agent formulated in a pharmaceutical formulation; and further aspects, wherein the kit comprises a package containing the pharmaceutical composition and instructions; and further asepcts, wherein the kit comprises a package containing the pharmaceutical composition and a device to administer the composition to a human or animal; and further aspects, wherein the device is an injectable device; and further aspects, wherein the injectable device is selected from a pen injector, auto injector and needle free injectors; and further aspects, wherein the needle free injector is a syringe; and further aspects, wherein the syringe is pre-filled with a liquid; and further aspects, wherein the syringe has a single chamber; and further aspects, wherein the syringe has dual chambers; and further aspects, wherein composition is lyophilized.

Aspects of the present invention disclose a pharmaceutical formulation, wherein the protein is Coagulation Factor IX and at least one of the two different amino acids is selected from the group consisting of G, P, A, S, T, V and N; and further aspects, wherein the protein is C1 Esterase Inhibitor and at least one of the two different amino acids is selected from the group consisting of K, R, G, A, E, S, T, D, P, V and N; and further aspects, wherein the antibody is basiliximab and at least one of the two different amino acids is selected from the group consisting of N, M, G, I, D, E, V, S, K, P and Q; and further aspects, wherein the antibody is panitumumab and at least one of the two different amino acids is selected from the group consisting of G, A, Y, V, P, D and M; and further aspects, wherein the protein is α-galactosidase A and at least one of the two different amino acids is selected from the group consisting of A, G, P, S, T and V; and further aspects, wherein the protein is β-glucocerebrosidase and at least one of the two different amino acids is selected from the group consisting of G, A, P, S, T, V, W, R, N, D, Q, E, I, L, K, M and F; and further aspects, wherein the antibody is cetuximab and at least one of the two different amino acids is selected from the group consisting of K, T, V, R, G, M, A, N, D, Q<E, H, I, L, F, P, S, W and Y; and further aspects, wherein the antibody is rituximab and at least one of the two different amino acids is selected from the group consisting of S, G, R, T, A, K, P, V, Q, N, I, M, L, D, E, W and Y; and further aspects, wherein the viscosity of a formulation containing rituximab is reduced by the addition of an amino acid selected from P, H, M, T and V.

Aspects of the present invention disclose a stable pharmaceutical formulation comprising a protein and one or more amino acids capable of stabilizing the protein in the formulation, wherein the protein is present at a concentration that is greater than the dose of that protein in a commercially available therapeutic containing the protein. Aspects of the present invention disclose a method of preparing a pharmaceutical formulation comprising one or more amino acids to stabilize a protein in the pharmaceutical formulation and one or more amino acids to reduce the viscosity of the pharmaceutical formulation, wherein the one or more amino acids to stabilize a protein and the one or more amino acids to reduce the viscosity of the pharmaceutical formulation are identified through the following method: (a) preformulation characterization; (b) high throughput screening; and, (c) long-term stability confirmation; wherein, the amino acids identified are included in the pharmaceutical formulation to provide stability and reduce viscosity of the pharmaceutical formulation.

Aspects of the present invention disclose a method of treating a human or animal suffering from a condition, the method comprising administration of a bioactive agent for treating the condition formulated in a pharmaceutical formulation comprising one or more amino acids to stabilize a protein in the pharmaceutical formulation and one or more amino acids to reduce the viscosity of the pharmaceutical formulation.

| Amino Acids | Concentration (mg/mL) | Amino Acids | Concentration (mg/mL) |
| --- | --- | --- | --- |
| S | 12.5 | R | 12.5 |
| T | 12.5 | K | 12.5 |
| A | 12.5 | Y | 0.13 |
| L | 5.0 | Q | 5.0 |
| G | 12.5 | E | 2.3 |
| F | 6.25 | D | 2.0 |
| M | 7.5 | N | 7.5 |
| V | 12.5 | H | 10 |
| P | 12.5 | W | 2.5 |
| I | 10 | | |

Figure 3:
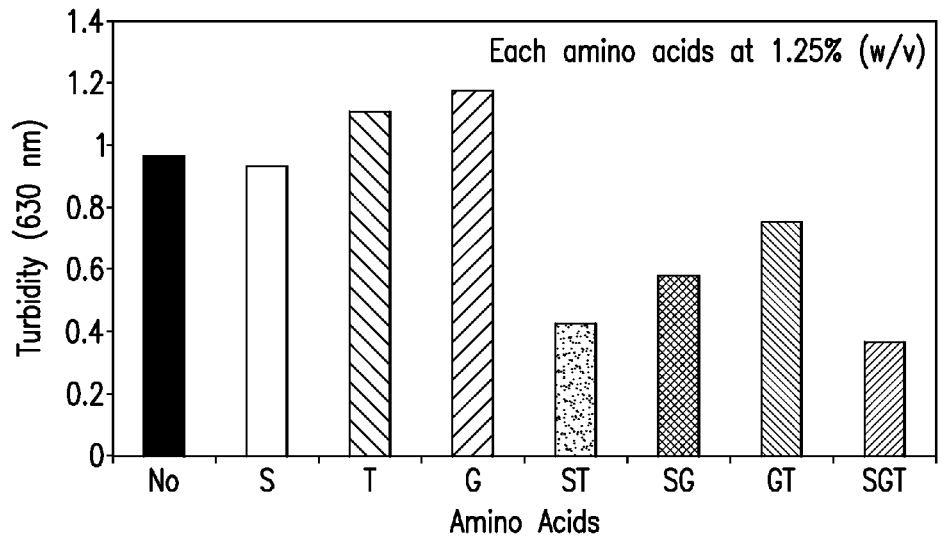

FIG. 3 presents the effects of amino acids on precipitation of Infliximab after 30 hours incubation at 50° C. The concentration of each amino acid was 1.25% (w/v). All tested samples contained 10 mg/mL of Infliximab, 5% sucrose, 0.005% polysorbate 80, and 5 mM sodium phosphate buffer at pH 7.2.

Figure 4:
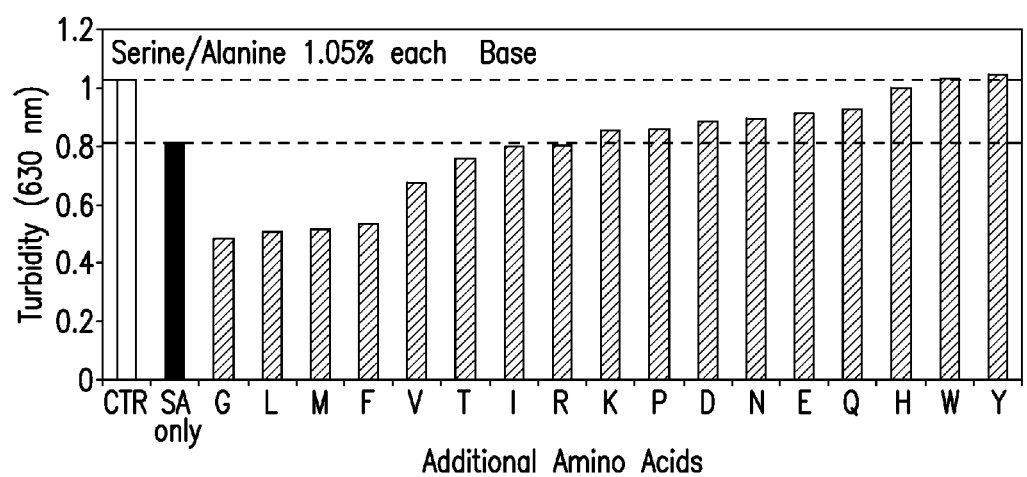

FIG. 4 presents the effects of amino acids on precipitation of Infliximab after 31 hours incubation at 50° C. The concentration of each base amino acid (serine and alanine) was 1.05% (w/v). All tested samples contained 10 mg/mL of Infliximab, 5% sucrose, 0.005% polysorbate 80, and 5 mM sodium phosphate buffer at pH 7.2. The concentrations of the third amino acids are shown in the table below.

| Amino Acids | Concentration (mg/mL) | Amino Acids | Concentration (mg/mL) |
| --- | --- | --- | --- |
| CTR | N/A | K | 10.50 |
| SA only | N/A | P | 10.50 |
| G | 10.50 | D | 1.68 |
| L | 4.20 | N | 6.30 |
| M | 6.30 | E | 1.89 |
| F | 5.25 | Q | 4.20 |
| V | 10.50 | H | 8.40 |
| T | 10.50 | W | 2.10 |
| I | 8.40 | Y | 0.11 |
| R | 10.50 | | |

Figure 5:
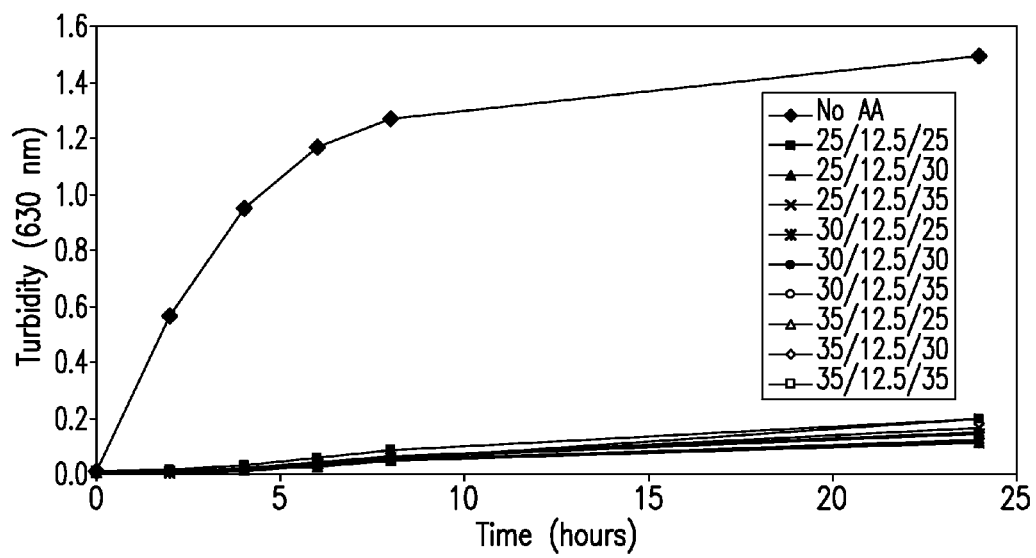

FIG. 5 shows the effects of the third amino acids on precipitation of Infliximab up to 24 hours incubation at 50° C. Different ratios of serine, alanine, and glycine were tested (concentration of each amino acid (%) labeled [serine]/[alanine]/[glycine]). All tested samples contained 10 mg/mL of Infliximab, 5% sucrose, 0.005% polysorbate 80, 5 mM sodium phosphate buffer at pH 7.2.

Figure 6:
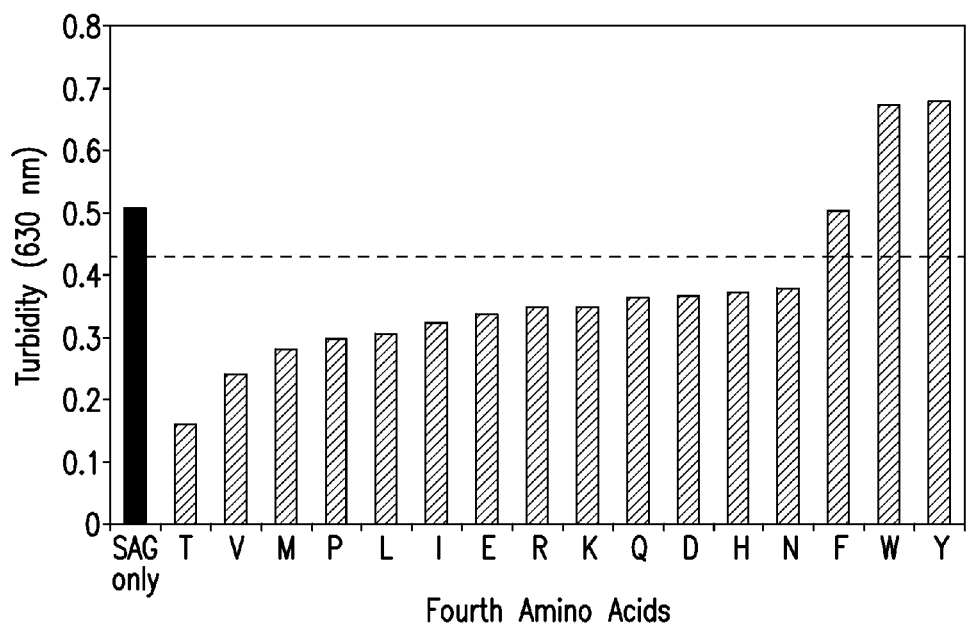

FIG. 6 shows the effects of the fourth amino acids on precipitation of Infliximab after 89 hours incubation at 50° C. All samples contained 3.5% serine, 1.25% alanine, and 3% glycine, 10 mg/mL of Infliximab, 5% sucrose, 0.005% polysorbate 80, 5 mM sodium phosphate buffer at pH 7.2. Concentration of each amino acid is identical as FIG. 4, except as specified.

Figure 7:
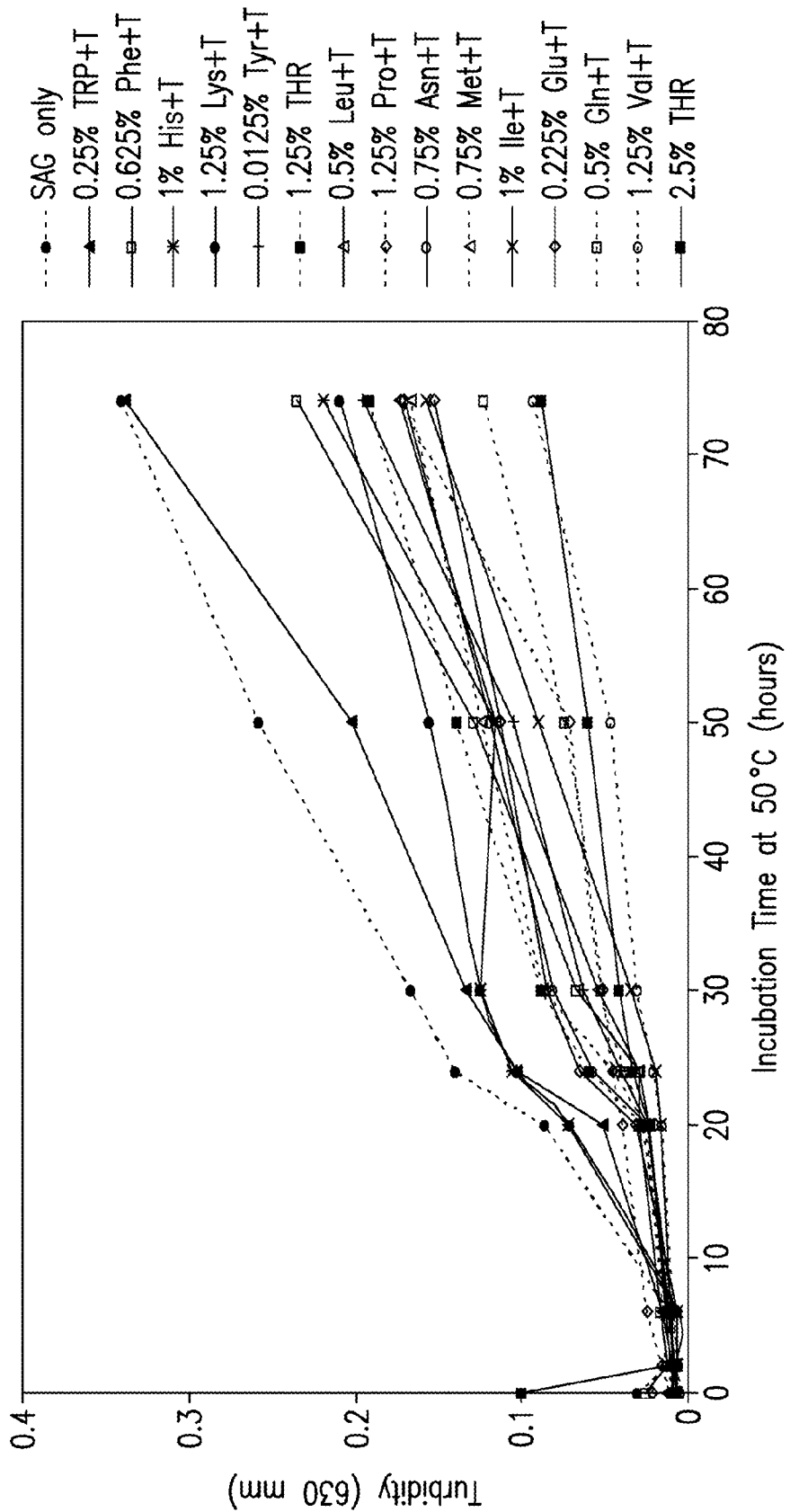

FIG. 7 shows the effects of the fourth and fifth amino acids on precipitation of Infliximab during 74 hours incubation at 50° C. All samples contained 3.5% serine, 1.25% alanine, 3% glycine, 1.25% threonine, 10 mg/mL of Infliximab, 5% sucrose, 0.005% polysorbate 80, 5 mM sodium phosphate buffer at pH 7.2.

Figure 8:
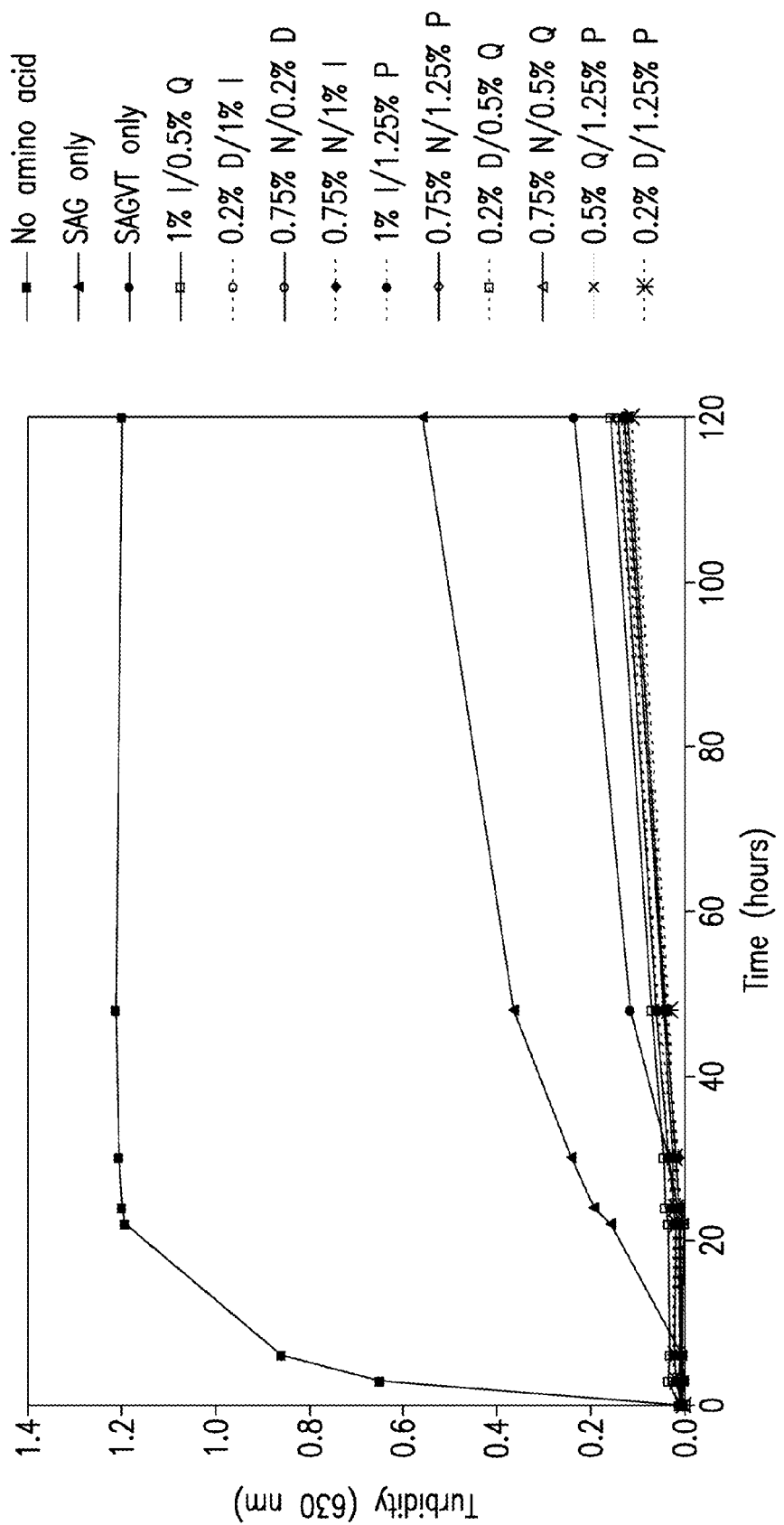

FIG. 8 shows the effects of the sixth and seventh amino acids on precipitation of Infliximab during 120 hours incubation at 50° C. All samples contained 3.5% serine, 1.25% alanine, and 3% glycine, 1.25% valine, and 1.25% threonine, except otherwise specified, 10 mg/mL of Infliximab, 5% sucrose, 0.005% polysorbate 80, 5 mM sodium phosphate buffer at pH 7.2. Unless specified, the amino acid concentrations shown in the following Table were used for the rest of the Figures below.

| Amino acids | Abbreviations | Final Concentration (% w/v) | | |
|---|---|---|---|---|
| | | Single AA | Double AA | Triple AA |
| L-Alanine | A | 2.50% | 1.25% | 0.63% |
| L-Arginine | R | 2.50% | 1.25% | 0.63% |
| L-Asparagine | N | 1.50% | 0.75% | 0.38% |
| L-Aspartic acid | D | 0.40% | 0.20% | 0.10% |
| L-Glutamine | Q | 1.00% | 0.50% | 0.25% |
| L-Glutamic acid | E | 0.45% | 0.23% | 0.11% |
| L-Glycine | G | 2.50% | 1.25% | 0.63% |
| L-Histidine | H | 2.00% | 1.00% | 0.50% |
| L-Isoleucine | I | 0.30% | 0.15% | 0.08% |
| L-Leucine | L | 0.20% | 0.10% | 0.05% |
| L-Lysine | K | 2.50% | 1.25% | 0.63% |
| L-Methonine | M | 1.50% | 0.75% | 0.38% |
| L-Phenylalanine | F | 0.25% | 0.13% | 0.06% |
| L-Proline | P | 2.50% | 1.25% | 0.63% |
| L-Serine | S | 2.50% | 1.25% | 0.63% |
| L-Threonine | T | 2.50% | 1.25% | 0.63% |
| L-Tryptophan | W | 0.10% | 0.05% | 0.03% |
| L-Tyrosine | Y | 0.01% | 0.00% | 0.00% |
| L-Valine | V | 2.50% | 1.25% | 0.63% |

Figure 9:
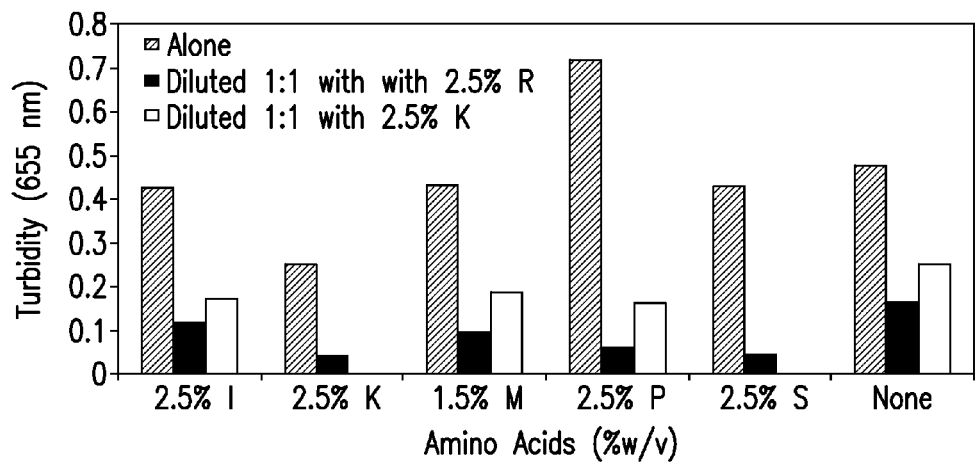

FIG. 9 shows the effects of the amino acids on precipitation of the antibody Cetuximab during incubation for 48 hours at 58° C. All samples contained 2 mg/mL Cetuximab and 0.85% sodium chloride in 10 mM sodium phosphate buffer at pH 7.2.

Figure 10:
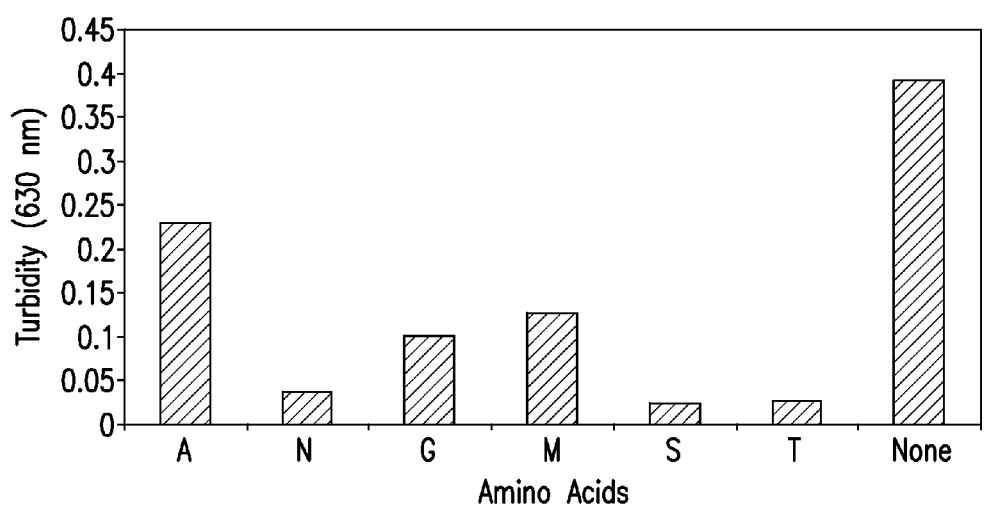

FIG. 10 shows the effects of the amino acids on precipitation of the antibody Bevacizumab during incubation for 6 hours at 60° C. All samples contained 12.5 mg/mL of the antibody, 30 mg/mL α,α-trehalose dihydrate, 2.9 mg/mL sodium phosphate (monobasic, monohydrate), 0.6 mg/mL sodium phosphate (dibasic, anhydrous), 0.2 mg/mL polysorbate 20 at pH 6.2

Figure 11:
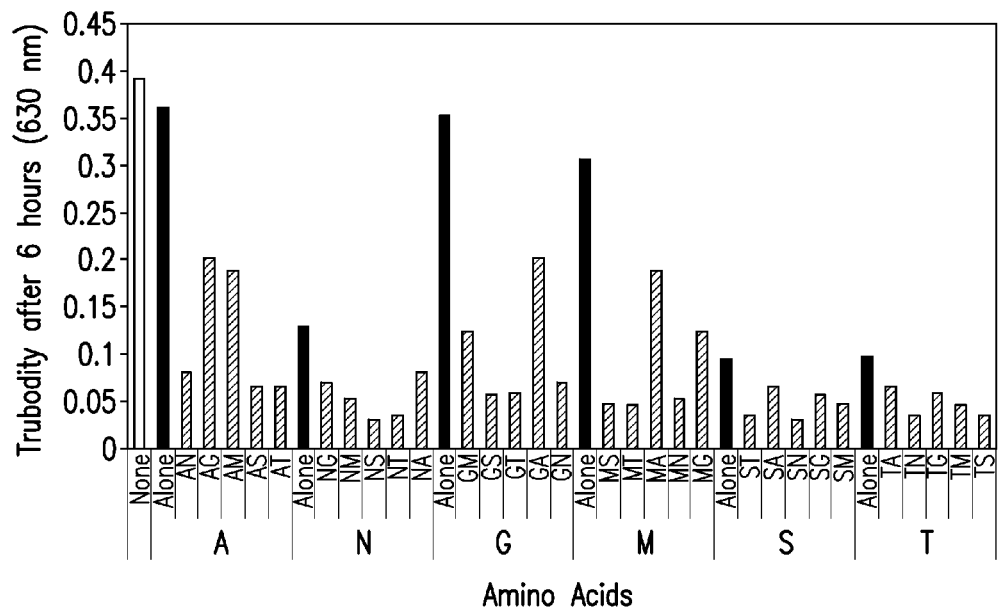

FIG. 11 shows the effects of the amino acids on precipitation of Bevacizumab during incubation for 6 hours at 60° C. All samples contained 12.5 mg/mL of the antibody, 30 mg/mL α,α-trehalose dihydrate, 2.9 mg/mL sodium phosphate (monobasic, monohydrate), 0.6 mg/mL sodium phosphate (dibasic, anhydrous), 0.2 mg/mL polysorbate 20 at pH 6.2

Figure 12:
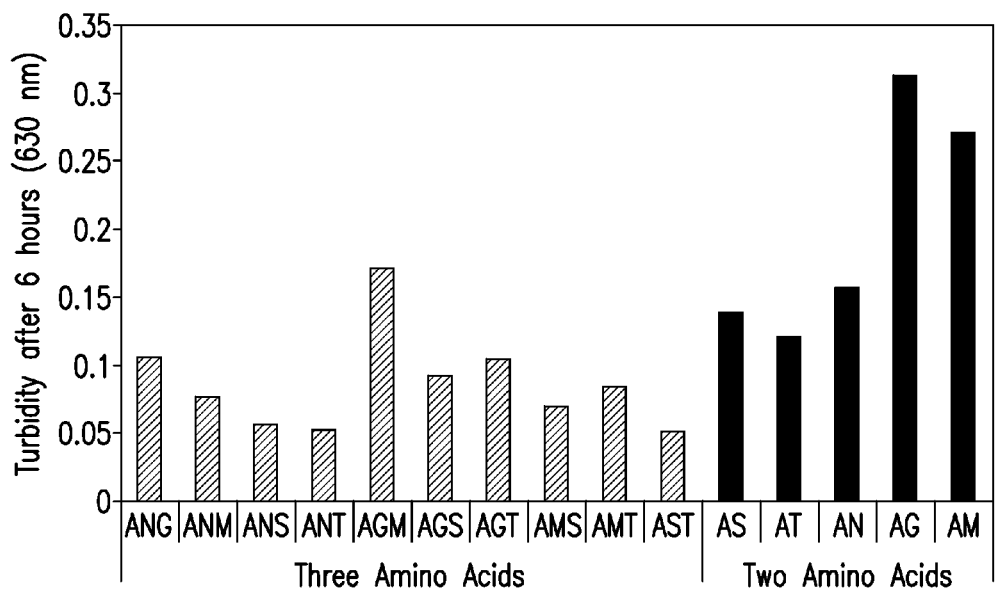

FIG. 12 shows the effects of L-alanine in combination with other amino acids on precipitation of Bevacizumab during incubation for 6 hours at 60° C. All samples contained 12.5 mg/mL of the antibody, 2.5% L-alanine, 30 mg/mL α,α-trehalose dihydrate, 2.9 mg/mL sodium phosphate (monobasic, monohydrate), 0.6 mg/mL sodium phosphate (dibasic, anhydrous), 0.2 mg/mL polysorbate 20 at pH 6.2

Figure 13:
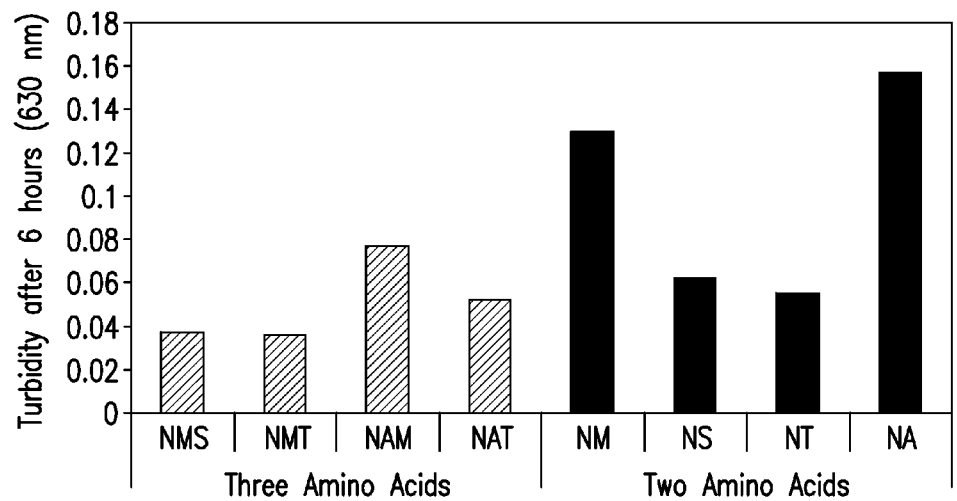

FIG. 13 shows the effects of L-asparagine in combination with other amino acids on precipitation of Bevacizumab during incubation for 6 hours at 60° C. All samples contained 12.5 mg/mL of the antibody, 30 mg/mL α,α-trehalose dihydrate, 2.9 mg/mL sodium phosphate (monobasic, monohydrate), 0.6 mg/mL sodium phosphate (dibasic, anhydrous), 0.2 mg/mL polysorbate 20 at pH 6.2

Figure 14:
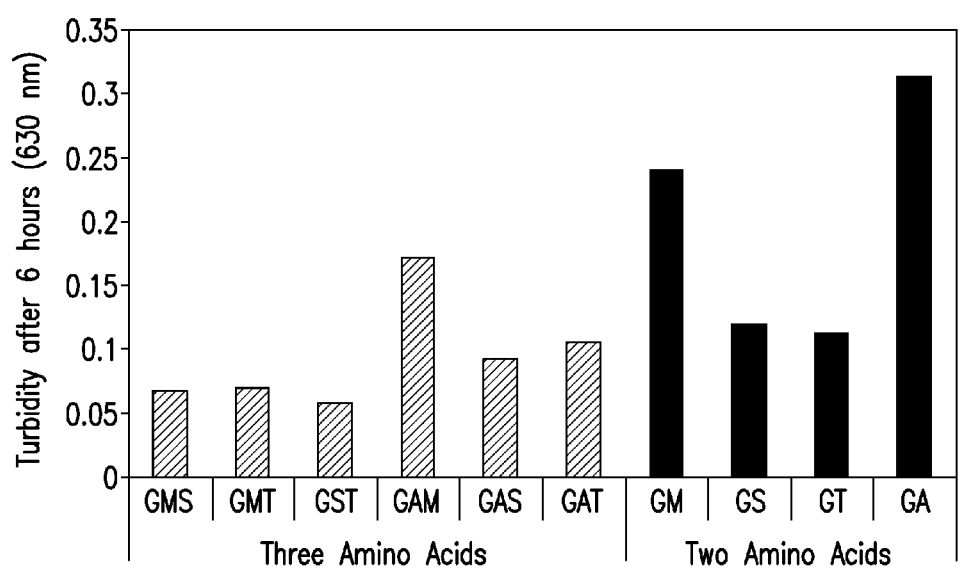

FIG. 14 shows the effects of L-glycine in combination with other amino acids on precipitation of Bevacizumab during incubation for 6 hours at 60° C. All samples contained 12.5 mg/mL of the antibody, 30 mg/mL α,α-trehalose dihydrate, 2.9 mg/mL sodium phosphate (monobasic, monohydrate), 0.6 mg/mL sodium phosphate (dibasic, anhydrous), 0.2 mg/mL polysorbate 20 at pH 6.2

Figure 15:
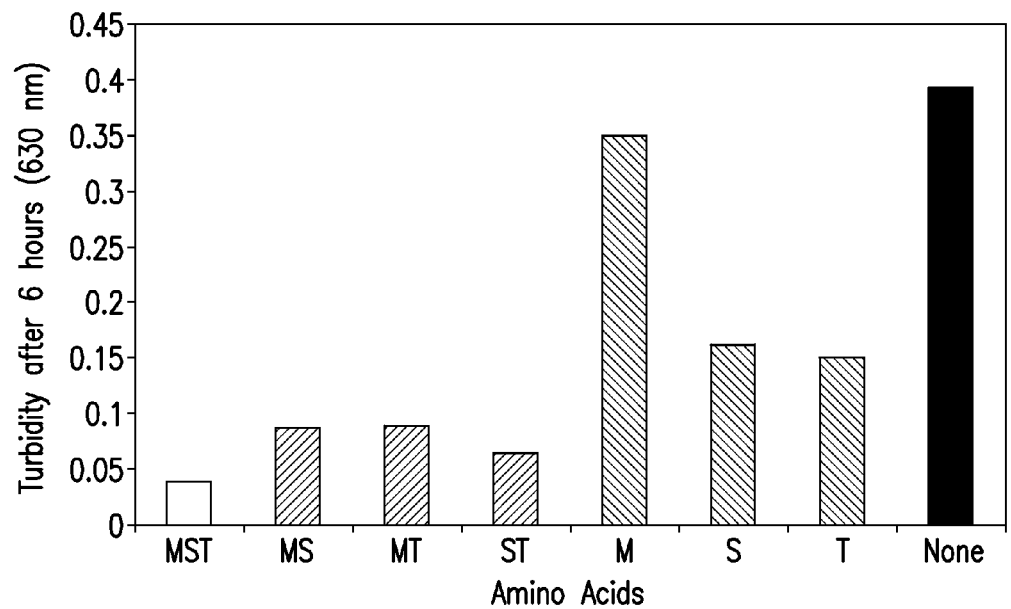

FIG. 15 shows the effects of combinations of amino acids on precipitation of Bevacizumab during incubation for 6 hours at 60° C. All samples contained 12.5 mg/mL of the antibody, 30 mg/mL α,α-trehalose dihydrate, 2.9 mg/mL sodium phosphate (monobasic, monohydrate), 0.6 mg/mL sodium phosphate (dibasic, anhydrous), 0.2 mg/mL polysorbate 20 at pH 6.2. Amino acid concentration followed triple AA.

Figure 16:
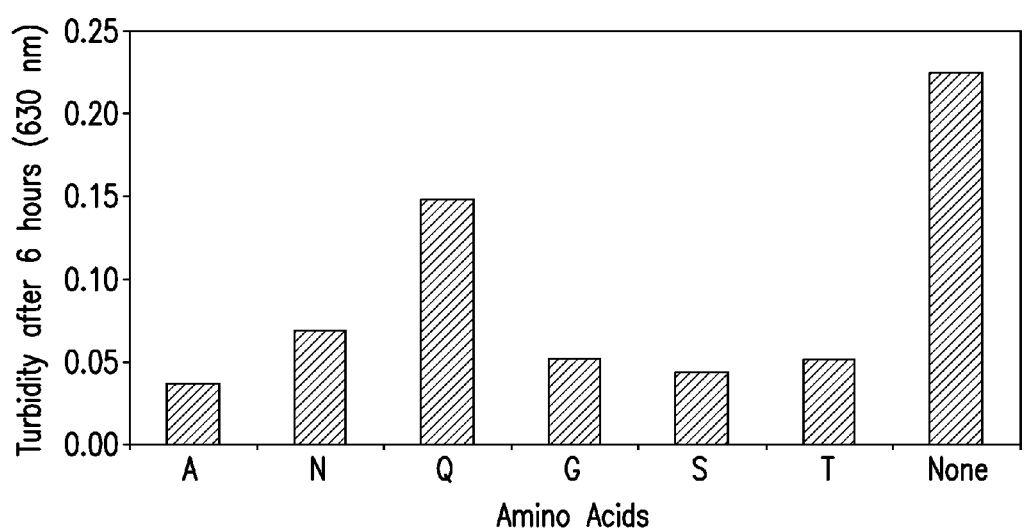

FIG. 16 shows the effects of amino acids on precipitation of Ranibizumab during incubation for 6 hours at 60° C. All samples contained 5 mg/mL Ranibizumab, 5 mM L-histidine HCl, 50 mg/mL α,α-trehalose dihydrate, and 0.05 mg/ml of polysorbate 20, at pH 5.5.

Figure 17:
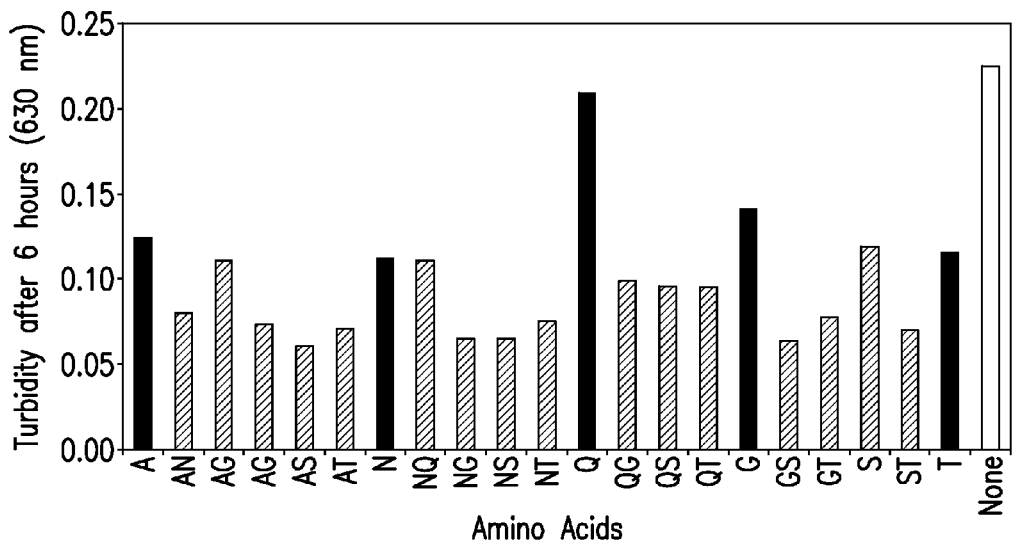

FIG. 17 shows the effects of amino acids on precipitation of Ranibizumab during incabation for 6 hours at 60° C. All samples contained 5 mg/mL Ranibizumab, 5 mM L-histidine HCl, 50 mg/mL α,α-trehalose dihydrate, and 0.05 mg/ml of polysorbate 20, at pH 5.5. Amino acid concentration followed double AA.

Figure 18:
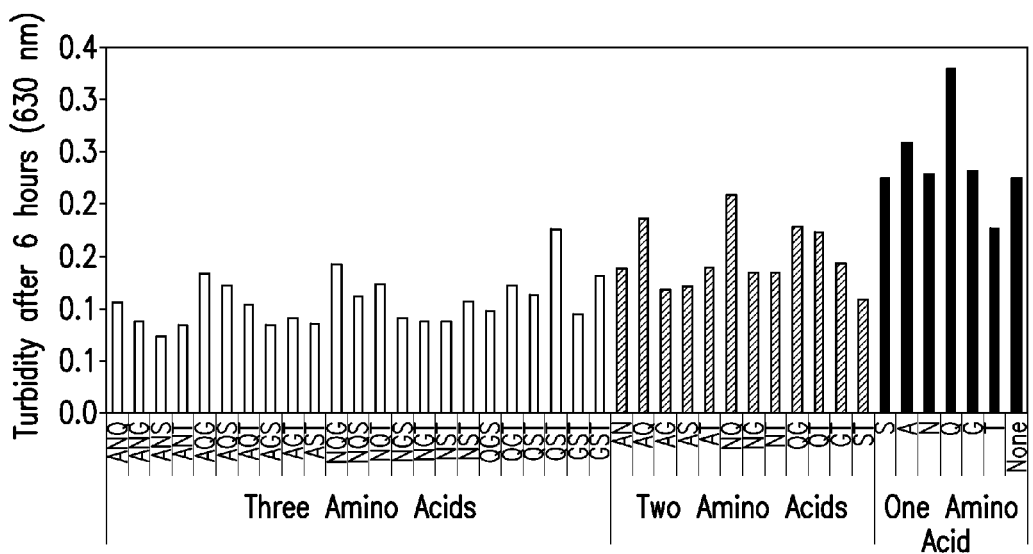

FIG. 18 shows the effects of amino acids on precipitation of Ranibizumab during incubation for 6 hours at 60° C. All samples contained 5 mg/mL Ranibizumab, 5 mM L-histidine HCl, 50 mg/mL α,α-trehalose dihydrate, and 0.05 mg/ml of polysorbate 20, at pH 5.5. Amino acid concentration followed triple AA.

Figure 19:
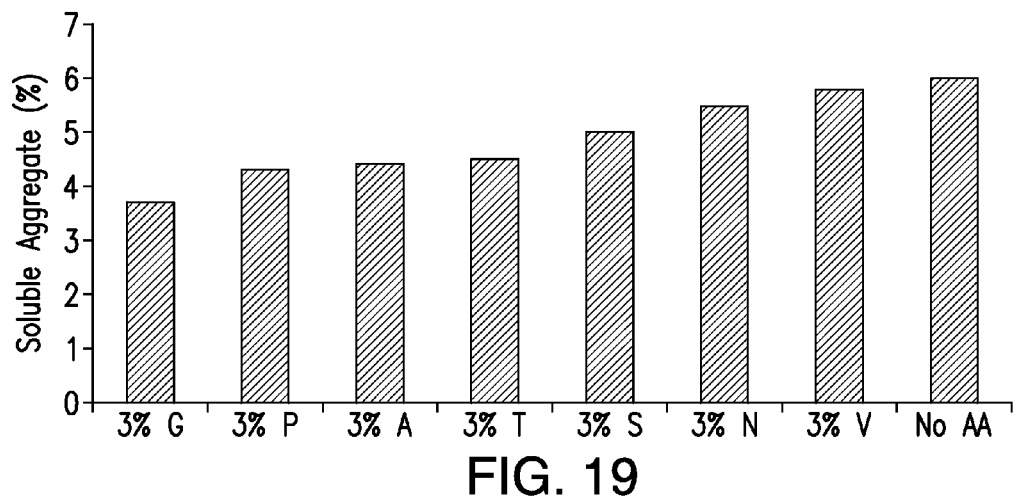

FIG. 19 shows the effects of amino acids on aggregation of Coagulation Factor IX during incubation for 24 hours at 50° C. All samples contained 37.5 mg Coagulation Factor IX, 0.234% sodium chloride, 8 mM L-histidine, 0.8% sucrose, 208 mM L-glycine, 0.004% polysorbate 80 in 5 ml of solution.

Figure 20:
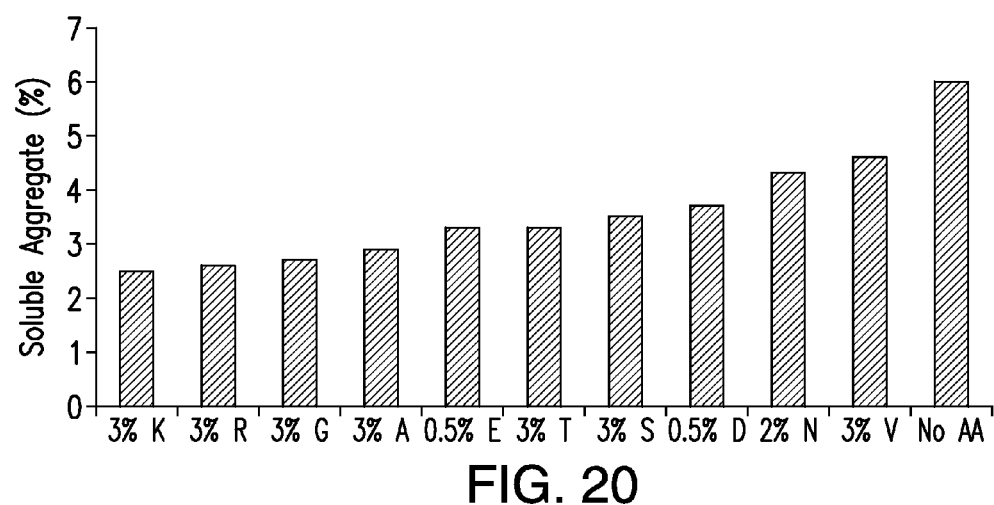

FIG. 20 shows the effects of amino acids on aggregation of C1 Esterase Inhibitor during incubation for 48 hours at 45° C. All samples contained 100 mg C1 Esterase Inhibitor, 85-115 mg L-glycine, 70-100 mg sodium chloride, 25-35 mg sodium acetate in 10 ml solution.

Figure 21:
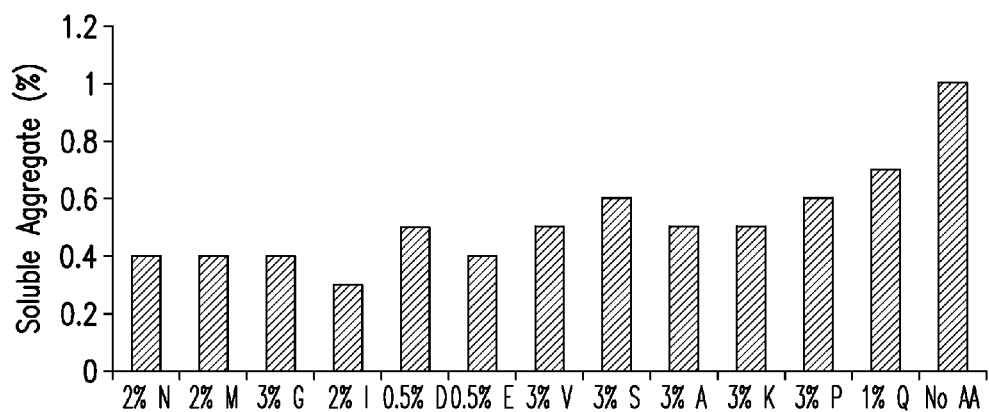

FIG. 21 shows the effects of amino acids on aggregation of Basiliximab during incubation for 48 hours at 55° C. All samples contained 10 mg Basiliximab, 0.99 mg disodium hydrogen phosphate, 1.61 mg NaCl, 7.21 mg potassium phosphate, 20 mg sucrose, 40 mg L-glycine and 80 mg mannitol in 5 ml solution.

Figure 22:
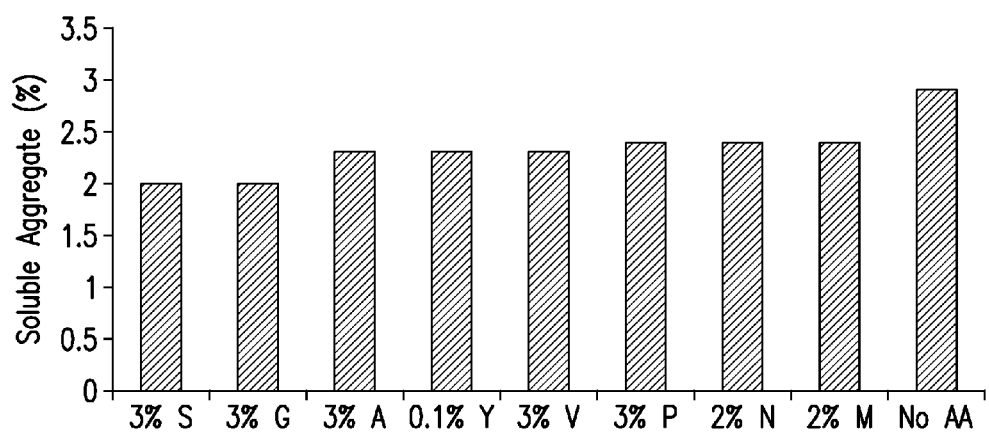

FIG. 22 shows the effects of amino acids on aggregation of Panitumumab during incubation for 48 hours at 55° C. All samples contained 200 mg Panitumumab, 117 mg NaCl, 136 mg. sodium acetate, pH 5.8 in 20 ml solution.

Figure 23:
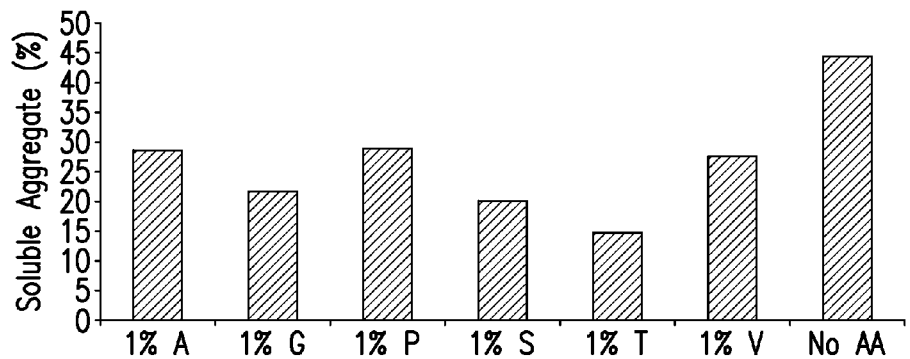

FIG. 23 shows the effects of amino acids on aggregation of α-galactosidase A during incubation for 16 hours at 45° C. All samples contained 5.5 mg of agalsidase beta, 33.0 mg mannitol, 3.0 mg sodium phosphate monobasic monohydrate, and 8.8 mg sodium phosphate dibasic heptahydrate in 1 ml solution.

Figure 24:
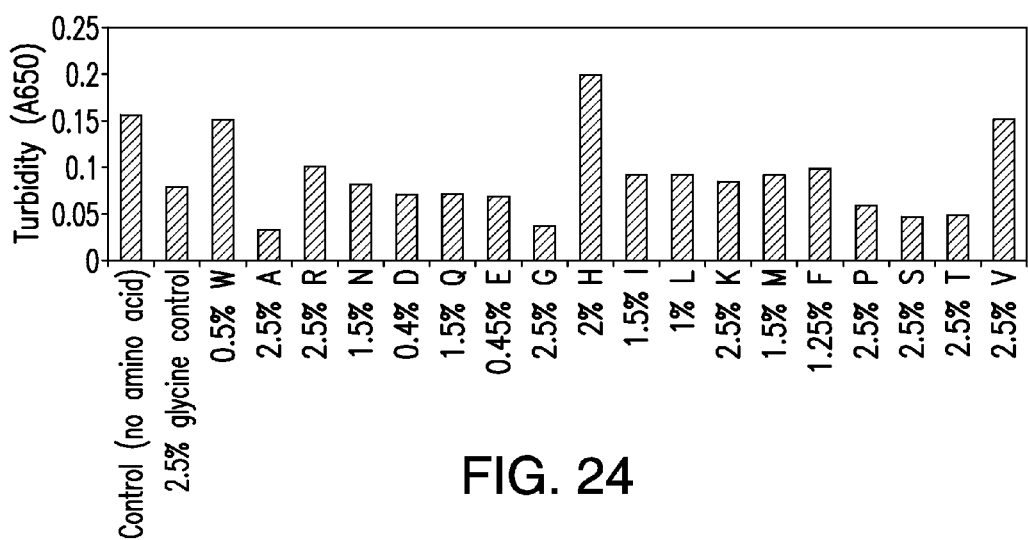

FIG. 24 shows the effects of amino acids on precipitation of β-glucocerebrosidase during incubation for 4 days at 40° C. All samples contained 100 U/ml β-glucocerebrosidase, 170 mg mannitol, 70 mg sodium citrates, 0.53 mg polysorbate 80 in 5 ml solution.

Figure 25:
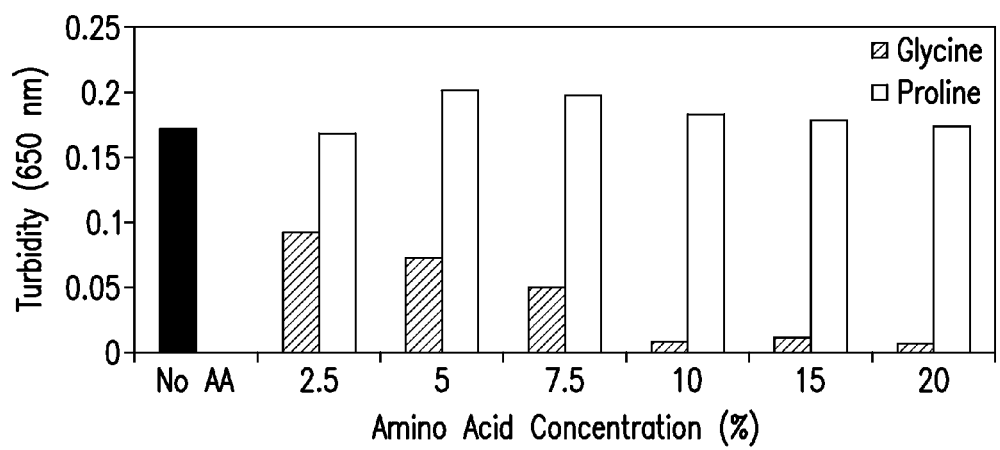

FIG. 25 shows the effects of amino acids on precipitation of Infliximab during incubation for 3 days at 50° C. All samples contained 150 mg/mL Infliximab, 50 mg/mL sucrose, 0.05 mg/mL polysorbate 80, 0.22 mg/mL monobasic sodium phosphate monohydrate and 0.61 mg/mL dibasic sodium phosphate dehydrate at a pH of 7.2. All samples diluted 10 times with a PBS before analysis.

Figure 26:
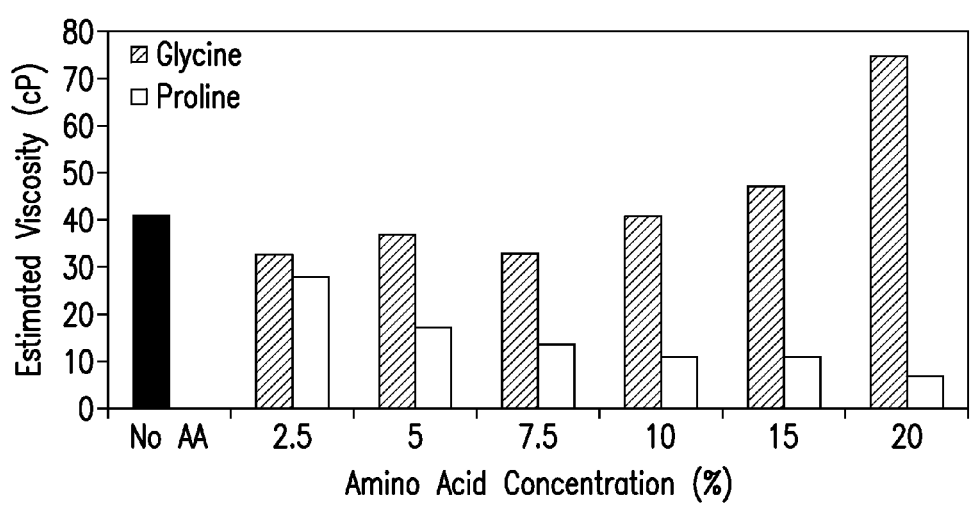

FIG. 26 shows the effects of amino acids on viscosity of Infliximab. All samples contained Infliximab at a concentration of 150 mg/ml. Identical formulation as FIG. 25.

Figure 27:
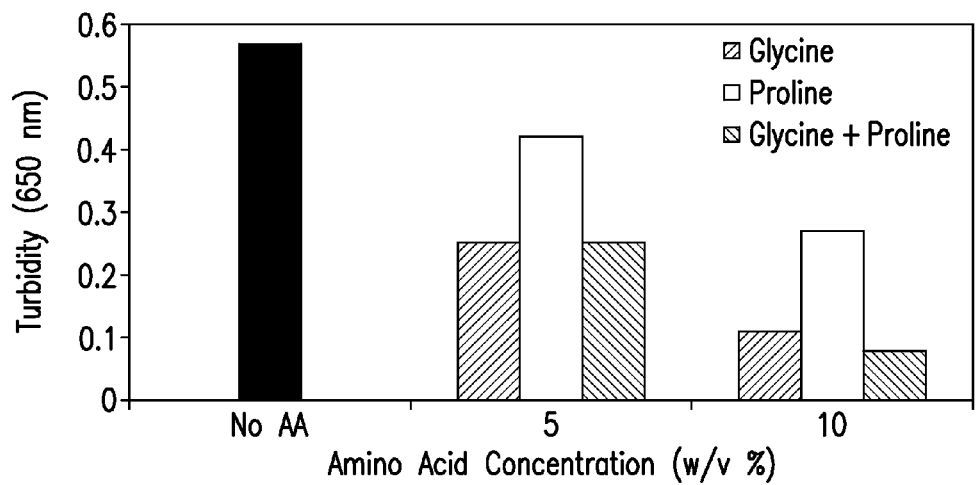

FIG. 27 shows the effects of Glycine and Proline on precipitates of Infliximab during incubation for 3 days at 45° C. Same formulation as FIG. 25.

Figure 28:
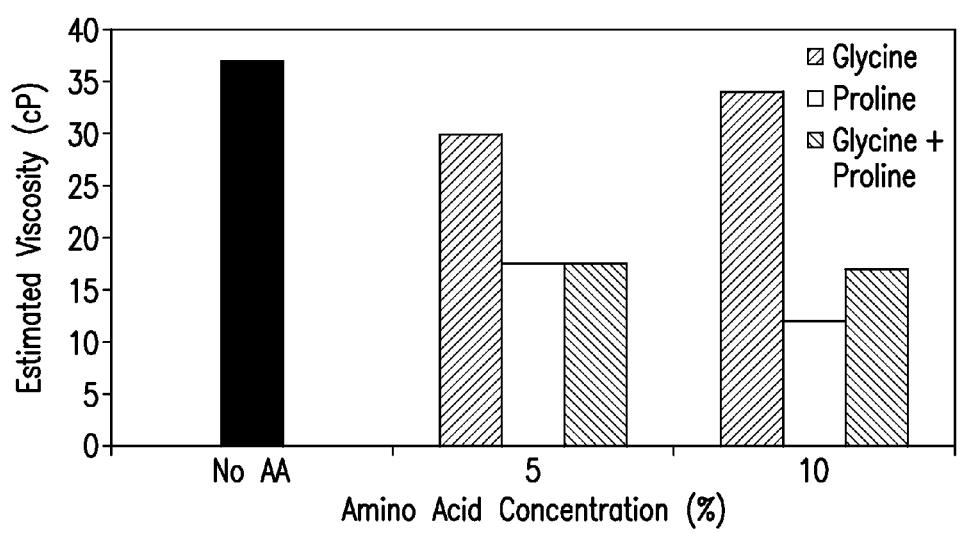

FIG. 28 shows the effects of Glycine and Proline on viscosity of Infliximab. All samples contained Infliximab at a concentration of 150 mg/ml.

Figure 29:
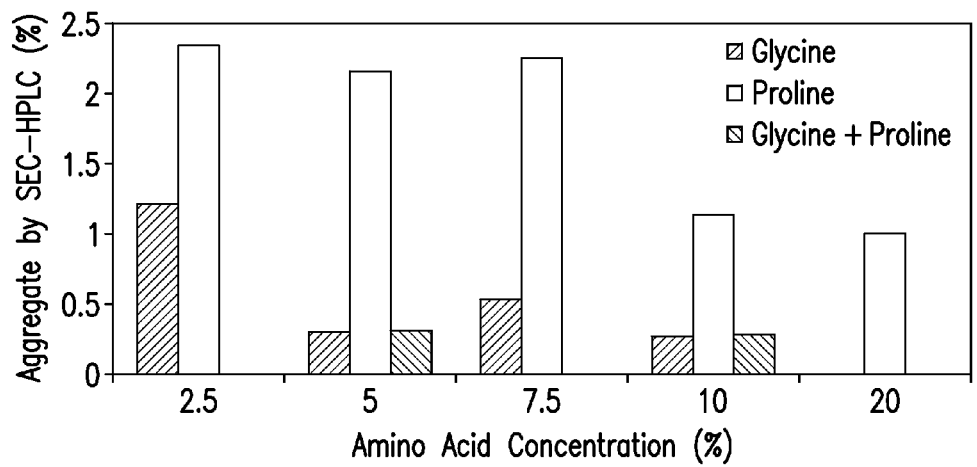

FIG. 29 shows the effects of Glycine and Proline on aggregation of Tratsuzumab during incubation after 20 hours at 55° C. All samples contained 200 mg/mL Tratsuzumab, 20 mg/ml trehalose, 0.5 mg L-histidine HCl, 0.32 mg/ml L-histidine and 0.09 mg/ml polysorbate 20 at a pH of 6.0. The sample incubated without amino acid turned into a gel.

Figure 30:
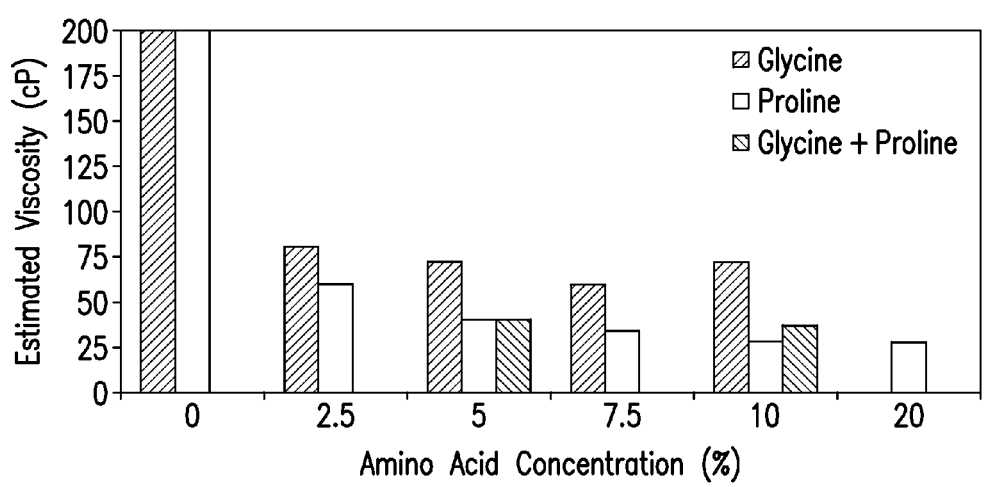

FIG. 30 shows the effects of Glycine and Proline on viscosity of Tratsuzumab. All samples contained Tratsuzumab at a concentration of 200 mg/ml.

Figure 31:
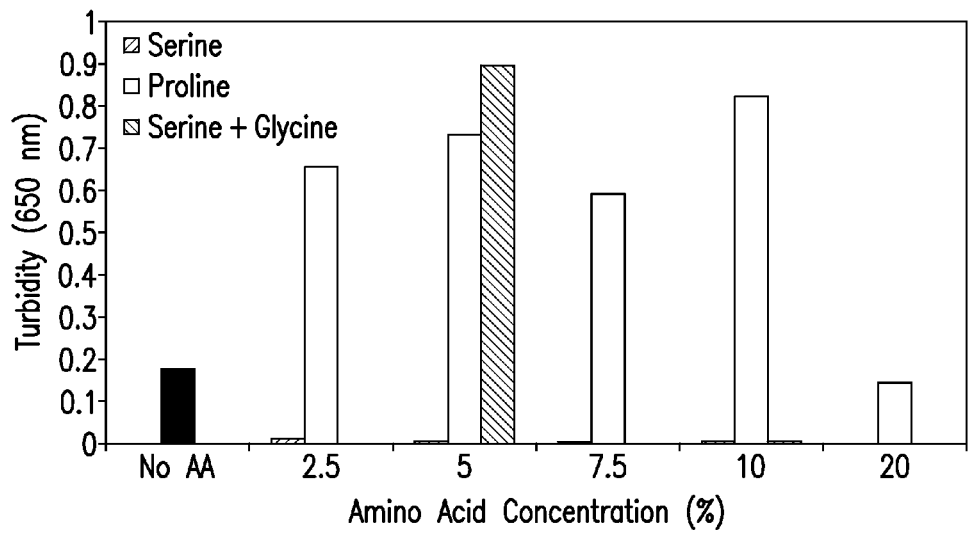

FIG. 31 shows the effects of Serine and Proline on precipitates of Rituximab during incubation after 20 hours at 55° C. All samples contained 200 mg/mL Rituximab, 10 mM sodium citrate buffer, 0.153 M sodium chloride and 0.07% polysorbate 80 at a pH of 6.5. The sample incubated without amino acid turned into a gel. All samples diluted 100 times with a PBS before measuring turbidity.

Figure 32:
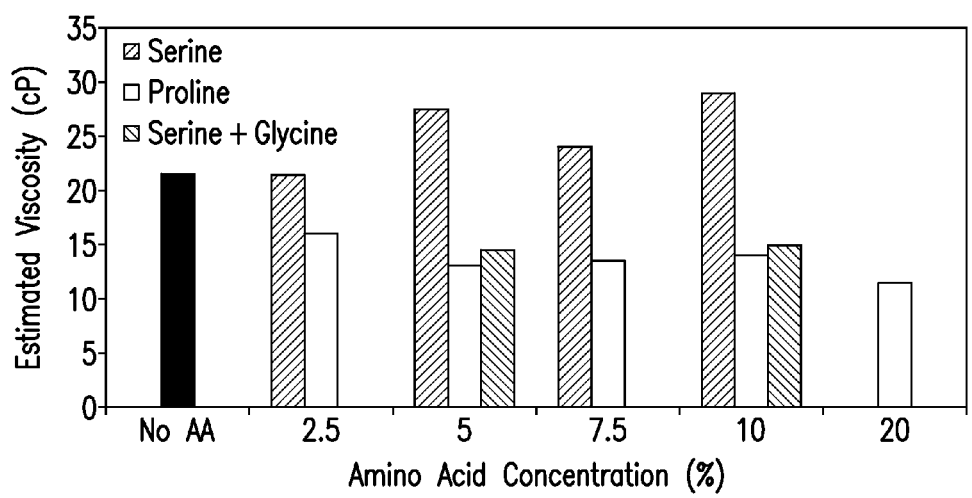

FIG. 32 shows the effects of Glycine and Proline on viscosity of Rituximab. All samples contained Rituximab at a concentration of 200 mg/ml.

Figure 33:
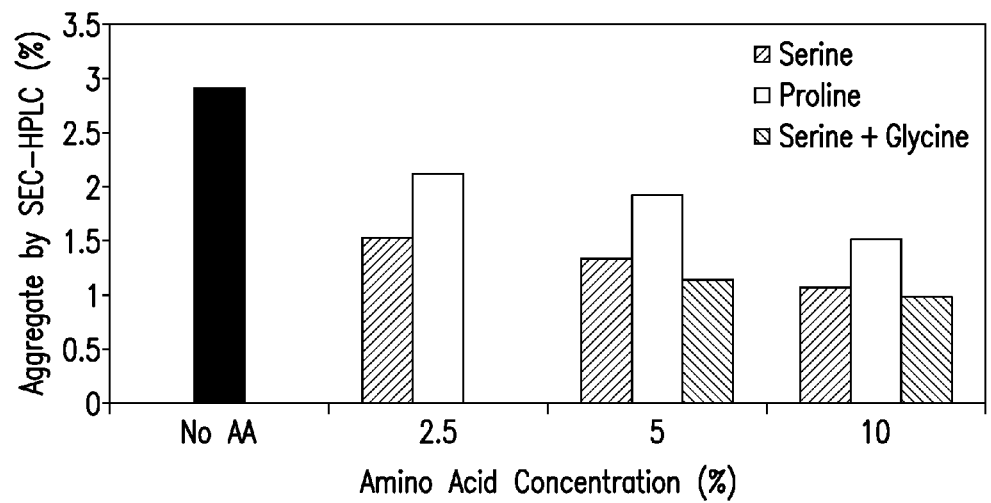

FIG. 33 shows the effects of Serine and Proline on aggregation of Palivizumab after incubation for 3 days at 45° C. All samples contained 250 mg/mL Palivizumab, 0.5 mg/ml sodium chloride, 0.1 mg/ml glycine and 3.9 mg/ml histidine.

Figure 34:
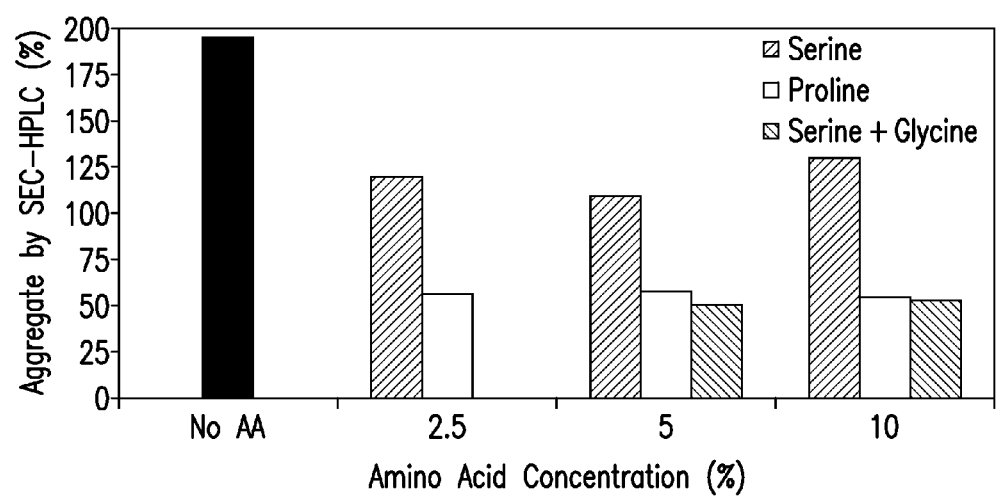

FIG. 34 shows the effects of Glycine and Proline on viscosity of Palivizumab. All samples contained Palivizumab at a concentration of 250 mg/ml.

Figure 35:
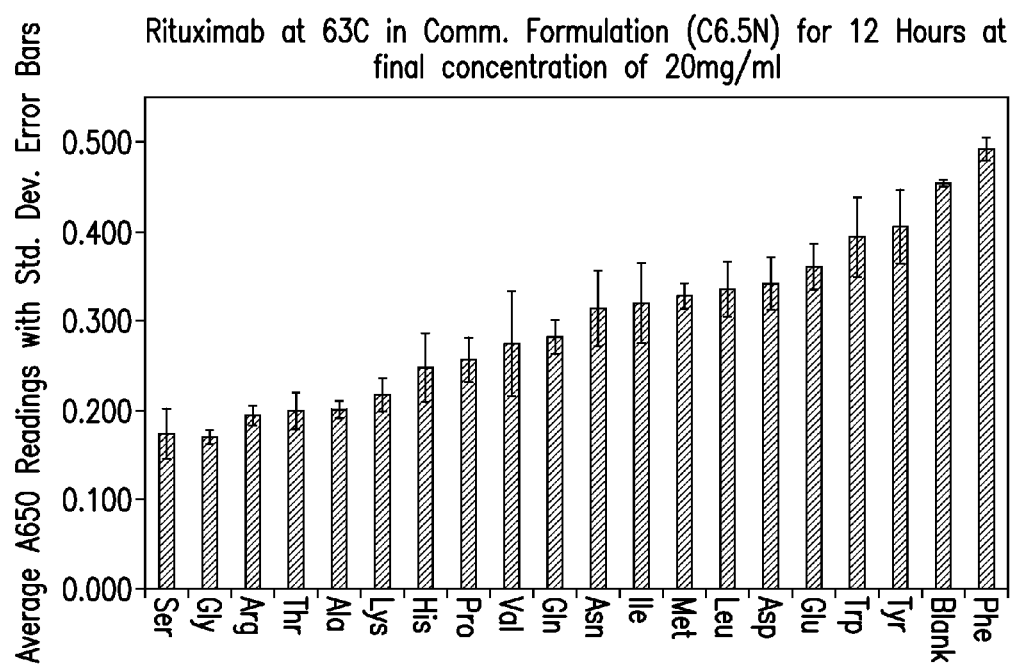

FIG. 35 shows the effects of amino acids of precipitates of Rituximab during incubation for 12 hours at 63° C. All samples contained 5 mg/mL Ritixumab, 10 mM sodium citrate buffer, 10 mM sodium citrate buffer at pH 6.5, 0.153 M NaCl, 0.07% polysorbate 80.

DETAILED DESCRIPTION

In an embodiment, the present invention discloses the formulation of proteins. In a further embodiment, the present invention discloses the formulation of a therapeutic protein in a stable formulation with low viscosity. In an additional embodiment, the present invention discloses the formulation of a therapeutic protein at high concentration in a stable formulation with low viscosity. In an embodiment, the present invention discloses the use of one or more amino acids in a formulation to improve the stability of a protein. In a further embodiment, the present invention discloses the use of one or more amino acids in a formulation to lower the viscosity of a protein. In another embodiment, the present invention discloses a formulation that is a liquid formulation for injection into a human or animal. In an embodiment, the present invention discloses a formulation that is a solid formulation, including, without limitation, a lyophilized formulation that is reconstitutable in a liquid prior to injection. In another embodiment, the present invention discloses the use of a pharmaceutical composition for therapeutic treatment.

The practices described herein employ, unless otherwise indicated, conventional techniques of tissue culture, immunology, molecular biology, microbiology, cell biology and recombinant DNA, which are within the skill of the art. See, e.g., Harlow and Lane eds. (1999) Antibodies, A Laboratory Manual and Herzenberg et al. eds (1996) Weir's Handbook of Experimental Immunology.

All numerical designations, e.g., pH, temperature, time, concentration, and molecular weight, including ranges, are to be understood as approximations in accordance with common practice in the art. When used herein, the term "about" may connote variation (+) or (−) 1%, 5% or 10% of the stated amount, as appropriate given the context. It is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a pharmaceutically acceptable carrier" includes a plurality of pharmaceutically acceptable carriers, including mixtures thereof. On the other hand "one" designates the singular.

As used herein, the term "comprising" is intended to mean that the compositions and methods include the listed elements, but do not exclude other unlisted elements. "Consisting essentially of" when used to define compositions and methods, excludes other elements that alters the basic nature of the composition and/or method, but does not exclude other unlisted elements. Thus, a composition consisting essentially of the elements as defined herein would not exclude trace amounts of elements, such as contaminants from any isolation and purification methods or pharmaceutically acceptable carriers, such as phosphate buffered saline, preservatives, and the like, but would exclude additional unspecified amino acids. "Consisting of" excludes more than trace elements of other ingredients and substantial method steps for administering the compositions described herein. Embodiments defined by each of these transition terms are within the scope of this disclosure and the inventions embodied therein.

As used herein, the term "formulation(s)" means a combination of at least one active ingredient with one or more other ingredient, also commonly referred to as excipients, which may be independently active or inactive. The term "formulation", may or may not refer to a pharmaceutically acceptable composition for administration to humans or animals, and may include compositions that are useful intermediates for storage or research purposes. In an embodiment, administration to humans or animals may include, without limitation, topical, sublingual, rectal, vaginal, trancutaneous, oral, inhaled, intranasal, pulmonary, subcutaneous, pulmonary, intravenous, enteral or parenteral.

As used herein, a protein can be a plasma derived protein or a recombinant protein. Production of a plasma derived protein can be through methods known in the art, including those related to the fractionation of blood plasma, colostrum or milk. Production of a recombinant therapeutic protein includes any method known in the art for (i) the production of recombinant DNA by genetic engineering, (ii) introducing recombinant DNA into prokaryotic or eukaryotic cells by, for example and without limitation, transfection, electroporation or microinjection, (iii) cultivating said transformed cells, (iv) expressing therapeutic protein, e.g. constitutively or upon induction, and (v) isolating said recombinant protein, e.g. from the culture medium or by harvesting the transformed cells, in order to obtain purified therapeutic protein. In other aspects, the therapeutic protein is produced by expression in a suitable prokaryotic or eukaryotic host system characterized by producing a pharmacologically acceptable blood coagulation protein molecule. Examples, without limitation, of eukaryotic cells are mammalian cells, such as CHO, COS, HEK 293, BHK, SK-Hep, and HepG2. A wide variety of vectors are used for the preparation of the therapeutic protein and are selected from eukaryotic and prokaryotic expression vectors. Examples, without limitation, of vectors for prokaryotic expression include plasmids such as, and without limitation, pRSET, pET, and pBAD, wherein the promoters used in prokaryotic expression vectors include one or more of, and without limitation, lac, trc, trp, recA, or araBAD. Examples, without limitation, of vectors for eukaryotic expression include: (i) for example, without limitation, for expression in yeast, vectors such as, and without limitation, pAO, pPIC, pYES, or pMET, using promoters such as, and without limitation, AOX1, GAP, GAL1, or AUG1; (ii) for example, without limitation, for expression in insect cells, vectors such as and without limitation, pMT, pAc5, pIB, pMIB, or pBAC, using promoters such as and without limitation PH, p10, MT, Ac5, OplE2, gp64, or polh, and (iii) for example, without limitation, for expression in mammalian cells, vectors such as and without limitation pSVL, pCMV, pRc/RSV, pcDNA3, or pBPV, and vectors derived from, in one aspect, viral systems such as and without limitation vaccinia virus, adeno-associated viruses, herpes viruses, or retroviruses, using promoters such as and without limitation CMV, SV40, EF-1, UbC, RSV, ADV, BPV, and .beta.-actin.

The abbreviations of amino acids used in the brief description of the drawings and the remainder of the present disclosure are shown in the table below.

| Amino Acid | 3-Letter | 1-Letter |
|---|---|---|
| Alanine | Ala | A |
| Arginine | Arg | R |
| Asparagine | Asn | N |
| Aspartic acid | Asp | D |
| Cysteine | Cys | C |
| Glutamic acid | Glu | E |
| Glutamine | Gln | Q |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

As used herein, the term "amino acid" refers to either natural and/or unnatural or synthetic amino acids, including glycine and both the D and L optical isomers, amino acid analogs and peptidomimetics. In some aspects, the term amino acid refers to monomeric amino acids.

In some aspects, the compositions and methods described herein address the problem of providing high concentration protein compositions, while maintaining administration practicability and stability. It has now been found that amino acids and their combinations, when included in a protein formulation as described herein, permit the preparation of highly concentrated protein formulations that maintain fluid-mechanical ability. Such formulations achieve reduced undue viscosity and gelation, and permit reconstitution of lyophilized materials. Thus, one embodiment provides a stable pharmaceutical formulation comprising a protein and one or more amino acids. In one aspect, each amino acid is present at a concentration of at least about 0.1% (w/v), or alternatively at least about 0.01%, 0.02%, 0.05%, 0.075%, 0.2%, 0.3%, 0.4%, 0.5%, 0.6%, 0.7%, 0.8%, 0.9%, 1%, 1.5%, 1.75%, 2%, 2.25%, 2.5%, 2.75%, 3%, 3.25%, 3.5%, 3.75%, 4%, 4.25%, 4.5%, 4.75%, 5%, 5.25%, 5.5%, 5.75%, 6%, 6.25%, 6.5%, 6.75%, 7%, 7.25%, 7.5%, 7.75%, 8%, 8.25%, 8.5%, 8.75%, 9%, 9.25%, 9.5%, 9.75%, 10%, 10.25%, 10.5%, 10.75%, 11%, 11.25%, 11.5%, 11.75%, 12%, 12.25%, 12.5%, 12.75%, 13%, 13.25%, 13.5%, 13.75%, 14%, 14.25%, 14.5%, 14.75%, 15%, 15.25%, 15.5%, 15.75%, 16%, 16.25%, 16.5%, 16.75%, 17%, 17.25%, 17.5%, 17.75%, 18%, 18.25%, 18.5%, 18.75%, 19%, 19.25%, 19.5%, 19.75%, 20%, 20.25%, 20.5%, 20.75%, 21%, 21.25%, 21.5%, 21.75%, 22%, 22.25%, 22.5%, 22.75%, 23%, 23.25%, 23.5%, 23.75%, 24%, 24.25%, 24.5%, 24.75%, 25%, 26%, 27%, 28%, 29%, 30%, 31%, 32%, 33%, 34%, 35%, 40%, or more (w/v).

In a further aspect, each amino acid is present at a concentration of about 0.1% (w/v) to about 40%, or alternatively at about 0.01% to about 25%, 0.02% to about 25%, 0.05% to about 25%, 0.075% to about 25%, 0.2% to about 25%, 0.3% to about 25%, 0.4% to about 25%, 0.5% to about 25%, 0.6% to about 25%, 0.7% to about 25%, 0.8% to about 25%, 0.9% to about 25%, 1% to about 25%, 1.5% to about 25%, 1.75% to about 25%, 2% to about 25%, 2.25% to about 25%, 2.5% to about 25%, 2.75% to about 25%, 3% to about 25%, 3.25% to about 25%, 3.5% to about 25%, 3.75% to about 25%, 4% to about 25%, 4.25% to about 25%, 4.5% to about 25%, 4.75% to about 25%, 5% to about 25%, 5.25% to about 25%, 5.5% to about 25%, 5.75% to about 25%, 6% to about 25%, 6.25% to about 25%, 6.5% to about 25%, 6.75% to about 25%, 7% to about 25%, 7.25% to about 25%, 7.5% to about 25%, 7.75% to about 25%, 8% to about 25%, 8.25% to about 25%, 8.5% to about 25%, 8.75% to about 25%, 9% to about 25%, 9.25% to about 25%, 9.5% to about 25%, 9.75% to about 25%, 10% to about 25%, 10.25% to about 25%, 10.5% to about 25%, 10.75% to about 25%, 11% to about 25%, 11.25% to about 25%, 11.5% to about 25%, 11.75% to about 25%, 12% to about 25%, 12.25% to about 25%, 12.5% to about 25%, 12.75% to about 25%, 13% to about 25%, 13.25% to about 25%, 13.5% to about 25%, 13.75% to about 25%, 14% to about 25%, 14.25% to about 25%, 14.5% to about 25%, 14.75% to about 25%, 15% to about 25%, 15.25% to about 25%, 15.5% to about 25%, 15.75% to about 25%, 16% to about 25%, 16.25% to about 25%, 16.5% to about 25%, 16.75% to about 25%, 17% to about 25%, 17.25% to about 25%, 17.5% to about 25%, 17.75% to about 25%, 18% to about 25%, 18.25% to about 25%, 18.5% to about 25%, 18.75% to about 25%, 19% to about 25%, 19.25% to about 25%, 19.5% to about 25%, 19.75% to about 25%, 20% to about 25%, 20.25% to about 25%, 20.5% to about 25%, 20.75% to about 25%, 5% to about 20%, 6% to about 20%, 7% to about 20%, 8% to about 20%, 9% to about 20%, 10% to about 20%, 11% to about 20%, 12% to about 20%, 13%, to about 20%, 14% to about 20%, 15% to about 20%, 5% to about 15%, 6% to about 15%, 7% to about 15%, 8% to about 15%, 9% to about 15%, 10% to about 15%, 11% to about 15%, 12% to about 15%, 13%, to about 15%, 14% to about 15% (w/v).

The term "protein" is used in its broadest sense to refer to a compound of two or more subunit amino acids, amino acid analogs or peptidomimetics. The subunits may be linked by peptide bonds. In another embodiment, the subunit may be linked by other bonds, e.g., ester, ether, etc. A protein or peptide must contain at least two amino acids and no limitation is placed on the maximum number of amino acids which may comprise a protein's or peptide's sequence. A peptide of three or more amino acids is commonly called an oligopeptide if the peptide chain is short. If the peptide chain is long, the peptide is commonly called a polypeptide or a protein.

Non-limiting examples of proteins, without limitation, that can be formulated in the stable formulations described herein include, without limitation, an enzyme, a cytokine, a neurotropic factor, an antibody, a peptide, a hormone, a DNA-binding protein, an aptamer, vaccines, toxins, Interleukin-1α (IL-1α), IL-1β, IL-2, IL-3, IL-4, IL-5, IL-6, IL-11, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-31, IL-32α, IL-33, colony stimulating factor-1 (CSF-1), macrophage colony stimulating factor, glucocerobrosidase, thyrotropin, stem cell factor, granulocyte macrophage colony stimulating factor, granulocyte colony stimulating factor (G-CSF), EPO, interferon-α (IFN-α), consensus interferon-β (IFN-β), interferon-γ (IFN-γ), interferon-Ω (IFN-Ω), thrombopoietin (TPO), Angiopoietin-1 (Ang-1), Ang-2, Ang-4, Ang-Y, angiopoietin-like polypeptide 1 (ANGPTL1), angiopoietin-like polypeptide 2 (ANGPTL2), angiopoietin-like polypeptide 3 (ANGPTL3), angiopoietin-like polypeptide 4 (ANGPTL4), angiopoietin-like polypeptide 5 (ANGPTL5), angiopoietin-like polypeptide 6 (ANGPTL6), angiopoietin-like polypeptide 7 (ANGPTL7), vitronectin, vascular endothelial growth factor (VEGF), angiogenin, activin A, activin B, activin C, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, bone morphogenic protein receptor II, brain derived neurotrophic factor, cardiotrophin-1, ciliary neutrophic factor, ciliary neutrophic factor receptor, cripto, cryptic, cytokine-induced neutrophil chemotactic factor 1, cytokine-induced neutrophil, chemotactic factor 2α, hepatitis B vaccine, hepatitis C vaccine, drotrecogin α, cytokine-induced neutrophil chemotactic factor 2β, endothelial cell growth factor, endothelin 1, epidermal growth factor (EGF), epigen, epiregulin, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor 11, fibroblast growth factor 12, fibroblast growth factor 13, fibroblast growth factor 16, fibroblast growth factor 17, fibroblast growth factor 19, fibroblast growth factor 20, fibroblast growth factor 21, fibroblast growth factor acidic, fibroblast growth factor basic, glial cell line-derived neutrophic factor receptor α1, glial cell line-derived neutrophic factor receptor α2, growth related protein, growth related protein α, IgG, IgE, IgM, IgA, and IgD, α-galactosidase, β-galactosidase, DNAse, fetuin, leutinizing hormone, alteplase, estrogen, insulin, albumin, lipoproteins, fetoprotein, transferrin, thrombopoietin, urokinase, integrin, thrombin, Factor IX (FIX), Factor VIII (FVIII), Factor VIIa (FVIIa), Von Willebrand Factor (VWF), Factor FV (FV), Factor X (FX), Factor XI (FXI), Factor XII (FXII), Factor XIII (FXIII), thrombin (FII), protein C, protein S, tPA, PAI-1, tissue factor (TF), ADAMTS 13 protease, growth related protein β, growth related protein γ, heparin binding epidermal growth factor, hepatocyte growth factor, hepatocyte growth factor receptor, hepatoma-derived growth factor, insulin-like growth factor I, insulin-like growth factor receptor, insulin-like growth factor II, insulin-like growth factor binding protein, keratinocyte growth factor, leukemia inhibitory factor, somatropin, antihemophiliac factor, pegaspargase, orthoclone OKT 3, adenosine deaminase, alglucerase, imiglucerase, leukemia inhibitory factor receptor α, nerve growth factor nerve growth factor receptor, neuropoietin,neurotrophin-3, neurotrophin-4, oncostatin M (OSM), placenta growth factor, placenta growth factor 2, platelet-derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor (SCF), stem cell factor receptor, TNF, TNF0, TNF1, TNF2, transforming growth factor α, hymic stromal lymphopoietin (TSLP), tumor necrosis factor receptor type I, tumor necrosis factor receptor type II, urokinase-type plasminogen activator receptor, phospholipase-activating protein (PUP), insulin, lectin ricin, prolactin, chorionic gonadotropin, follicle-stimulating hormone, thyroid-stimulating hormone, tissue plasminogen activator (tPA), leptin, Enbrel (etanercept).

In some embodiments, the protein is an antibody. As used herein, an "antibody" includes, without limitation, whole antibodies and any antigen binding fragment or a single chain thereof. Thus the term "antibody" includes, without limitation, any protein or peptide containing molecule that comprises at least a portion of an immunoglobulin molecule having biological activity of binding to the antigen. Examples of such may comprise a complementarity determining region (CDR) of a heavy or light chain or a ligand binding portion thereof, a heavy chain or light chain variable region, a heavy chain or light chain constant region, a framework (FR) region, or any portion thereof, or at least one portion of a binding protein. "Antibody" also includes both monoclonal antibodies and polyclonal antibodies.

Examples of antibodies include, without limitation, Infliximab, Bevacizumab, Ranibizumab, Cetuximab, Ranibizumab, Palivizumab, Abagovomab, Abciximab, Actoxumab, Adalimumab, Afelimomab, Afutuzumab, Alacizumab, Alacizumab pegol, ALD518, Alemtuzumab, Alirocumab, Alemtuzumab, Altumomab, Amatuximab, Anatumomab mafenatox, Anrukinzumab, Apolizumab, Arcitumomab, Aselizumab, Altinumab, Atlizumab, Atorolimiumab, tocilizumab, Bapineuzumab, Basiliximab, Bavituximab, Bectumomab, Belimumab, Benralizumab, Bertilimumab, Besilesomab, Bevacizumab, Bezlotoxumab, Biciromab, Bivatuzumab, Bivatuzumab mertansine, Blinatumomab, Blosozumab, Brentuximab vedotin, Briakinumab, Brodalumab, Canakinumab, Cantuzumab mertansine, Cantuzumab mertansine, Caplacizumab, Capromab pendetide, Carlumab, Catumaxomab, CC49, Cedelizumab, Certolizumab pegol, Cetuximab, Citatuzumab bogatox, Cixutumumab, Clazakizumab, Clenoliximab, Clivatuzumab tetraxetan, Conatumumab, Crenezumab, CR6261, Dacetuzumab, Daclizumab, Dalotuzumab, Daratumumab, Demcizumab, Denosumab, Detumomab, Dorlimomab aritox, Drozitumab, Duligotumab, Dupilumab, Ecromeximab, Eculizumab, Edobacomab, Edrecolomab, Efalizumab, Efungumab, Elotuzumab, Elsilimomab, Enavatuzumab, Enlimomab pegol, Enokizumab, Enokizumab, Enoticumab, Enoticumab, Ensituximab, Epitumomab cituxetan, Epratuzumab, Erlizumab, Ertumaxomab, Etaracizumab, Etrolizumab, Exbivirumab, Exbivirumab, Fanolesomab, Faralimomab, Farletuzumab, Fasinumab, FBTA05, Felvizumab, Fezakinumab, Ficlatuzumab, Figitumumab, Flanvotumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, GS6624, Ibalizumab, Ibritumomab tiuxetan, Icrucumab, Igovomab, Imciromab, Imgatuzumab, Inclacumab, Indatuximab ravtansine, Infliximab, Intetumumab, Inolimomab, Inotuzumab ozogamicin, Ipilimumab, Iratumumab, Itolizumab, Ixekizumab, Keliximab, Labetuzumab, Lebrikizumab, Lemalesomab, Lerdelimumab, Lexatumumab, Libivirumab, Ligelizumab, Lintuzumab, Lirilumab, Lorvotuzumab mertansine, Lucatumumab, Lumiliximab, Mapatumumab, Maslimomab, Mavrilimumab, Matuzumab, Mepolizumab, Metelimumab, Milatuzumab, Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Narnatumab, Natalizumab, Nebacumab, Necitumumab, Nerelimomab, Nesvacumab, Nimotuzumab, Nivolumab, Nofetumomab merpentan, Ocaratuzumab, Ocrelizumab, Odulimomab, Ofatumumab, Olaratumab, Olokizumab, Omalizumab, Onartuzumab, Oportuzumab monatox, Oregovomab, Orticumab, Otelixizumab, Oxelumab, Ozanezumab, Ozoralizumab, Pagibaximab, Palivizumab, Panitumumab, Panobacumab, Parsatuzumab, Pascolizumab, Pateclizumab, Patritumab, Pemtumomab, Perakizumab, Pertuzumab, Pexelizumab, Pidilizumab, Pintumomab, Placulumab, Ponezumab, Priliximab, Pritumumab, PRO 140, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Sevirumab, Sibrotuzumab, Sifalimumab, Siltuximab, Simtuzumab, Siplizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Tefibazumab, Telimomab aritox, Tenatumomab, Teneliximab, Teplizumab, Teprotumumab, TGN1412, tremelimumab, Ticilimumab, Tildrakizumab, Tigatuzumab, TNX-650, Tocilizumab, Toralizumab, Tositumomab, Tralokinumab, Trastuzumab, TRBS07, Tregalizumab, Tremelimumab, Tucotuzumab celmoleukin, Tuvirumab, Ublituximab, Urelumab, Urtoxazumab, Ustekinumab, Vapaliximab, Vatelizumab, Vedolizumab, Veltuzumab, Vepalimomab, Vesencumab, Visilizumab, Volociximab, Vorsetuzumab mafodotin, Votumumab, Zalutumumab, Zanolimumab, Zatuximab, Ziralimumab and Zolimomab aritox.

The term "stable formulation" such as "stable pharmaceutical formulation" as used herein in connection with the formulations described herein denotes, without limitation, a formulation, which preserves its physical stability/identity/integrity and/or chemical stability/identity/integrity and/or biological activity/identity/integrity during manufacturing, storage and application. Various analytical techniques for evaluating protein stability are available in the art and reviewed in Reubsaet, J. L., J. H. Beijnen, et al. (1998) "Analytical techniques used to study the degradation of proteins and peptides: chemical instability," *J Pharm Biomed Anal* 17(6-7): 955-78 and Wang, W. (1999) "Instability, stabilization, and formulation of liquid protein pharmaceuticals," *Int J Pharm* 185(2): 129-88. Stability can be evaluated by, for example, without limitation, storage at selected climate conditions for a selected time period, by applying mechanical stress such as shaking at a selected shaking frequency for a selected time period, by irradiation with a selected light intensity for a selected period of time, or by repetitive freezing and thawing at selected temperatures. The stability may be determined by, for example, without limitation, at least one of the methods selected from the group consisting of visual inspection, SDS-PAGE, IEF, size exclusion liquid chromatography (SEC-HPLC), reversed phase liquid chromatography (RP-HPLC), ion-exchange HPLC, capillary electrophoresis, light scattering, particle counting, turbidity, RFFIT, and kappa/lambda ELISA, without limitation. For example, in the data presented in the figures, stability is assessed with reference to turbidity and aggregate formation.

In an embodiment, a formulation is considered stable when the protein in the formulation (1) retains its physical stability, (2) retains its chemical stability and/or (3) retains it biological activity.

In an embodiment, a protein may be said to "retain its physical stability" in a formulation if, for example, without limitation, it shows no signs of aggregation, precipitation and/or denaturation upon visual examination of color and/or clarity, or as measured by UV light scattering or by size exclusion chromatography (SEC) or electrophoresis, such as with reference to turbidity or aggregate formation.

In an embodiment, a protein may be said to "retain its chemical stability" in a formulation, if, for example, without limitation, the chemical stability at a given time is such that there is no significant modification of the protein by bond formation or cleavage resulting in a new chemical entity. In a further embodiment, chemical stability can be assessed by detecting and quantifying chemically altered forms of the protein. Chemical alteration may involve, example, without limitation, size modification (e.g. clipping) which can be evaluated using size exclusion chromatography, SDS-PAGE and/or matrix-assisted laser desorption ionization/time-of-flight mass spectrometry (MALDI/TOF MS). Other types of chemical alteration include, for example, without limitation, charge alteration (e.g. occurring as a result of deamidation), which can be evaluated by ion-exchange chromatography, for example. Oxidation is another commonly seen chemical modification.

In an embodiment, a protein may be said to "retain its biological activity" relative to native unmodified protein in a pharmaceutical formulation, if, for example, without limitation, the biological activity of the protein, such as an antibody, at a given time is between about 50% and about 200%, or alternatively between about 60% and about 170%, or alternatively between about 70% and about 150%, or alternatively between about 80% and about 125%, or alternatively between about 90% and about 110%, of the biological activity exhibited at the time the formulation was prepared as determined, e.g., in an antigen binding assay or virus neutralization assay. In a further embodiment, a protein may be said to "retain its biological activity" in a pharmaceutical formulation, if, for example, without limitation, the biological activity of the protein, such as an antibody, at a given time is at least 1%, 5%, 10%, 15%, 20%, 25%, 30%, 35%, 40%, 45%, 50%, 55%, 60%, 65%, 70%, 75%, 80%, 85%, 90%, 95% or 100%.

In one embodiment, a stable protein formulation contains a protein and at least one amino acid selected based on the amino acid's ability to increase the stability of the protein and/or reduce solution viscosity. In one embodiment, the amino acid contains a positively charged side chain, such as R, H, and K. In another aspect, the amino acid contains a negatively charged side chain, such as D and E. In another embodiment, the amino acid contains a hydrophobic side chain, such as A, F, I, L, M, V, W, and Y. In another embodiment, the amino acid contains a polar uncharged side chain, such as S, T, N, and Q. In yet another embodiment, the amino acid does not have a side chain, i.e., G.

In an embodiment, the amino acid is not H or R. In another embodiment, the amino acid is not M. In another aspect, the amino acid is not D, E, K, R, G, H, M or A. In one embodiment, the amino acid is any one of A, N, D, Q, E, I, L, K, F, P, S, T, W, Y, or V.

In one embodiment, the protein is a monoclonal antibody selected from infliximab, bevacizumab or ranibizumab and the amino acid is selected from the group consisting of S, T, N, P, A, Q, V and G. In another embodiment, the protein is a monoclonal antibody selected from trastuzumab or rituximab and the amino acid is selected from the group consisting of H, R, N, M and K.

In yet another embodiment, the protein is cetuximab, rituximab, bevacizumab, ranibizumab, or C-1 esterase inhibitor, and the amino acid is selected from the group consisting of K, R, M, P, S and I. In still another embodiment, the protein is α-galactosidase A, β-glucocerebrosidase, infliximab, rituximab, cetuximab, ranibizumab, coagulation factor IX, bevacizumab, or vectibix, and the amino acid is selected from the group consisting of S, T, A, P and G.

Still further, Tables 7 and 8 below provide amino acids, useful either alone or in combination, for preparing stable protein formulations.

As noted above, while not wanting to be bound by any theory, it is contemplated that, without limitation, based on the discoveries described herein, the amino acids in a protein formulation may reversibly antagonize or block the regions on a protein molecule in the solution that interact with other protein molecules to destabilize a high concentration formulation.

In general, the forces causing protein degradation may be thought of in terms of chemical and physical instability. Water may destabilize protein directly, or act as a solvent transferring destabilizing agents, and therefore, reducing or eliminating water may promote stabilization. Freeze- or spray-drying is based on this rational. Aqueous environments, however, may be necessary for native protein tertiary (or quaternary) structure as, for example, forces of hydrogen bonding determine protein folding.

Within a protein, nonpolar amino acids are typically localized to the internal core to avoid exposure to water solvent, and residues with polar side chains are typically exposed on the surface. When considering the protein as a whole, the hydrogen bonds/polarity have a cumulative effect; hydrogen bonds with the surface-accessibility of polar amino acids can be stabilizing forces and dehydration can be destabilizing in this regard. Lyophilization, therefore, can promote degradation and appropriate excipients may act as a stabilizing force.

In this respect, therefore, it is contemplated (but not a binding theory) that a combination of polar/non-polar or hydrophilic/hydrophobic amino acid monomers serves to neutralize protein-protein interaction based on amphiphilic profile. Thus, the use of a combination of one-or-more-polar with one-or-more non-polar amino acid monomers may reduce the potential for deleterious protein-protein actions by reversibly impeding access to regions on the underlying subject biomolecule by other biomolecules in the solution.

As such, some embodiments use at least one amino acid as stabilizers permitting increased protein concentration while substantially limiting the deleterious effects of concomitant protein-protein interaction. Thus, one embodiment provides a stable pharmaceutical formation comprising a protein and one amino acid. In one aspect, the amino acids is not H or R. As such, some embodiments use at least two different amino acids as stabilizers permitting increased protein concentration while substantially limiting the deleterious effects of concomitant protein-protein interaction. Thus, one embodiment provides a stable pharmaceutical formation comprising a protein and two different amino acids. In one embodiment, the two different amino acids are not H or R. In one embodiment, an amino acid contains a positively charged side chain. In another aspect, an amino acid contains a negatively charged side chain. In another embodiment, an amino acid contains a hydrophobic side chain. In another aspect, an amino acid contains a polar uncharged side chain. Still in another embodiment, an amino acid contains a polar uncharged side chain and the other is selected from the group consisting of G and P. In one embodiment, at least one of the two different amino acids contains a positively charged side chain. In another as embodiment aspect, at least one of the two different amino acids contains a negatively charged side chain. In another embodiment, at least one of the two different amino acids contains a hydrophobic side chain. In another embodiment, at least one of the two different amino acids contains a polar uncharged side chain. In yet another asp embodiment ect, one of the two different amino acids contains a polar uncharged side chain and the other contains a hydrophobic side chain. Still in another embodiment, one of the two different amino acids contains a polar uncharged side chain and the other is selected from the group consisting of G and P. In one embodiment, one of the two different amino acids is selected, without limitation, from the group consisting of I, M, P, S, R, K, E, and N. In another aspect, each of the two different amino acids is selected from the group consisting of S, T, N, G, A, K, F, V, L, E, H, I, and P. In yet another embodiment, each of the two different amino acids is selected, without limitation, from the group consisting of S, T, N, G, P, and A.

Examples of proteins are provided above. In one embodiment, the protein is an antibody. In one embodiment, the antibody is selected, without limitation, from the group consisting of infliximab, bevacizumab, and ranibizumab, and at least one of the two different amino acids is selected, without limitation, from the group consisting of S, T, N, G, P, Q, V and A. In another embodiment, the antibody is cetuximab and at least one of the two different amino acids is selected, without limitation, from the group consisting of I, M, P, S, R, K, E, and N. In another embodiment, the antibody is rituximab and at least one of the two different amino acids is selected, without limitation, from the group consisting of H, R, P, M, K, and F. In yet another embodiment, the antibody is trastuzumab and at least one of the two different amino acids is selected, without limitation, from the group consisting of K, M, G, H, P, R, and N.

Another embodiment provides a stable protein formulation that contains, without limitation, at least three different amino acids. Yet another embodiment provides a stable protein formulation that contains, without limitation, at least four different amino acids. Still another embodiment provides a stable protein formulation that contains, without limitation, at least five, or six, or seven, or eight, or nine or ten different amino acids.

Additional examples of two amino acid combinations are provided below. In one embodiment, each of the amino acids is any of A with S, G, N, M, S, P or T. In one embodiment, the first amino acid is F and the second amino acid is any of S, G, P or T, or the first amino acid is G and the second amino acid is any of A, F, M, N, Q, S, P or T, or the first amino acid is I and the second amino acid is any of R or K, or the first amino acid is K and the second amino acid is any of R, I, M, or P, or the first amino acid is L and the second amino acid is S, or the first amino acid is M and the second amino acid is any of A, G, K, N, R, S, P or T, or the first amino acid is N and the second amino acid is any of A, G, M, Q, S, P or T, or the first amino acid is P and the second amino acid is any of K or R, or the first amino acid is Q and the second amino acid is any of A, N, G, S, T, P or W, or the first amino acid is R and the second amino acid is any of I, K, M, P, S, or W, or the first amino acid is S and the second amino acid is any of A, F, G, L, M, N, P, Q, R, T, V, or the first amino acid is T and the second amino acid is any of A, F, G, M, N, P, Q, S, V, or W, or the first amino acid is V and the second amino acid is any of S or T, or the first amino acid is W and the second amino acid is any of H, P, Q, or R. Additional examples of three amino acid combinations are provided below. In one embodiment, the three amino acids are any of the first amino acid is A and the second and the third amino acid are any combinations of F, G, L, M, N, P, Q, S, T, or V, or the first amino acid is F and the second and the third amino acid are any combinations of A, G, P, S, or T, or the first amino acid is G and the second and the third amino acid are any combinations of A, M, N, P, Q, S, or T, or the first amino acid is I and the second and the third amino acid are any combinations of R or K, or the first amino acid is K and the second and the third amino acid are any combinations of R, I, M, or P, or the first amino acid is L and the second and the third amino acid are any combinations of A, G, P, S, or T, or the first amino acid is M and the second and the third amino acid are any combinations of A, G, K, N, P, R, S, or T, or the first amino acid is N and the second and the third amino acid are any combinations of A, G, M, P, Q, S, or T, or the first amino acid is P and the second and the third amino acid are K and R, or the first amino acid is Q and the second and the third amino acid are any combinations of A, N, P, G, S, or T, or the first amino acid is R and the second and the third amino acid are any combinations of I, K, M, P, S, or W, or the first amino acid is S and the second and the third amino acid are any combinations of A, F, G, L, M, N, P, Q, R, T, V, or the first amino acid is T and the second and the third amino acid are any combinations of A, F, G, M, N, P, Q, S, V, or W, or the first amino acid is V and the second and the third amino acid are any combinations of A, P, S or T, or the first amino acid is W and the second and the third amino acid are any combinations of H, P, Q, or R. Also disclosed are compositions comprising a protein and a plurality of 4 amino acids. Further disclosed are compositions comprising a protein and a plurality of 5 amino acids.

In an embodiment each of the amino acids are selected from the 20 natural amino acids. In an embodiment the amino acids include natural amino acids. In an embodiment the amino acids are or include other amino acids that do not occur naturally. In embodiments the amino acids are or include synthetic amino acids that do not occur naturally.

In various embodiments a formulation is provided containing 1, 2, 3, 4, 5 or 6 or more different amino acids, as well as, for one or more bioactive agents combined with one or more excipients. In an embodiment, the one or more different amino acids are selected based on their ability to stabilize a protein in a formulation. In another embodiment, the one or more different amino acids are selected based on their ability to reduce the viscosity of a solution containing a protein in a formulation. In a further embodiment, the formulation is comprised of one or more amino acids capable of stabilizing a protein in a formulation and one or more different amino acids capable of reducing the viscosity of a solution containing a protein. In an embodiment the one or more amino acids capable of stabilizing a protein in a formulation is the same one or more amino acids capable of reducing the viscosity of a solution containing a protein. In a further embodiment, the one or more amino acids capable of stabilizing a protein in a formulation is different than the one or more amino acids capable of reducing the viscosity of a solution containing a protein. In an embodiment, the amino acid capable of stabilizing a protein in a formulation is the same as the amino acid capable of reducing the viscosity of a solution. In a further embodiment, the amino acid capable of stabilizing a protein in a formulation is different from the amino acid capable of reducing the viscosity of a solution.

In an embodiment, the amino acid capable of stabilizing a protein in solution includes, without limitation, G, S, T, A, R, M, K, P, N or any combination thereof. In a further embodiment, the amino acid capable of reducing the viscosity of a solution containing a protein includes, without limitation, P. In an embodiment, a formulation capable of stabilizing a protein and reducing the viscosity of a solution comprises, without limitation, a combination of G, S, T, A, R, M, K, P and/or N and P.

Still further and within the scope of the compositions and methods described herein, Tables 7 and 8 below provide amino acids combinations that are suitable for preparing stable protein formulations.

In any of the above embodiments of the formulations, whether containing one single amino acid or combinations of different amino acids, the formulations may have a pH that is from about 4 to about 6 or from about 5 to about 7.5. Alternatively, in a further embodiment, without limitation, the pH is from about 5 to about 6, from about 6 to about 7, or from about 6.5 to about 7.5. In an embodiment, the pH is at least about 2, 2.25, 2.5, 2.75, 3, 3.25, 3.5, 3.75, 4, 4.25, 4.5, 4.75, 5, 5.25, 5.5, 5.75, 6, 6.25, 6.5, 6.75, 7, 7.25, 7.5, 7.75, 8, 8.25, 8.5, 8.75, 9, 9.25, 9.5, 9.75, 10, 10.25, 10.5, 10.75, 11, 11.25, 11.5, 11.75, 12. In a further embodiment, the pH of the formulation is in the range of about 2 to about 12, about 3 to about 11, about 4 to about 10, about 5 to about 9, about 6 to about 8, about 6 to about 7, about 6 to about 9, about 6 to about 10, about 5 to about 6, about 5 to about 7, about 5 to about 8, about 4 to about 9, about 4 to about 8, about 4 to about 7, about 4 to about 6, about 4 to about 5, about 3 to about 10, about 3 to about 9, about 3 to about 8, about 3 to about 7, about 3 to about 6, about 3 to about 5, about 3 to about 4, about 2 to about 11, about 2 to about 10, about 2 to about 9, about 2 to about 8, about 2 to about 7, about 2 to about 6, about 2 to about 5, about 2 to about 4, about 2 to about 3, about 7 to about 8, about 7 to about 9, about 7 to about 10, about 7 to about 11, about 7 to about 12, about 8 to about 9, about 8 to about 10, about 8 to about 11, about 8 to about 12, about 9 to about 10, about 9 to about 11, about 9 to about 12, about 10 to about 11, about 10 to about 12 or about 11 to about 12.

By virtue of the stabilizing effect of the amino acids, the compositions and methods described herein permit the preparation of stable protein formulations that contain a protein at a higher concentration, such as at least 1% (w/v), 2% (w/v), 3% (w/v), 4% (w/v), 5% (w/v), 6% (w/v), 7% (w/v), 8% (w/v), 9% (w/v), 10% (w/v), 11% (w/v), 12% (w/v), 13% (w/v), 14% (w/v), 15% (w/v), 16% (w/v), 17% (w/v), 18% (w/v), 19% (w/v), 20% (w/v), 21% (w/v), 22% (w/v), 23% (w/v), 24% (w/v), 25% (w/v), 26% (w/v), 27% (w/v), 28% (w/v), 29% (w/v), 30% (w/v), 31% (w/v), 32% (w/v), 33% (w/v), 34% (w/v), 35% (w/v), 36% (w/v), 37% (w/v), 38% (w/v), 39% (w/v), 40% (w/v), 45% (w/v), 50% (w/v) or more.

In an embodiment a stable pharmaceutical formulation comprising a protein and one or more amino acids capable of stabilizing the protein in the formulation, wherein the protein is present at a concentration that is greater than the dose of that protein in a commercially available therapeutic containing the protein. In an embodiment, one or more amino acids is added to a pharmaceutical formulation to stabilize a protein in said formulation. In a further embodiment, the one or more amino acids are able to stabilize a protein at a concentration greater than the dose of that protein in a commercially available therapeutic that does not include the one or more amino acids for the purpose of stabilizing the protein. By virtue of the stabilizing effect of the one or more amino acids, the concentration of a protein can be increased in the pharmaceutical formulation by 1%, 2%, 3%, 4%, 5%, 6%, 7%, 8%, 9%, 10%, 11%, 12%, 13%, 14%, 15%, 20%, 25%, 30%, 35%, 40%, 45%, 50%, 55%, 60%, 65%, 70%, 75%, 80%, 85%, 90%, 95%, 100%, 105110%, 115%, 120%, 125%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490%, 500%, 525%, 550%, 575%, 600%, 625%, 650%, 675%, 700%, 800%, 900%, 1000% or more than the dose of that protein in a commercially available therapeutic that does not include the one or more amino acids for the purpose of stabilizing the protein.

By virtue of the stabilizing effect of the amino acids, the compositions and methods described herein permit the preparation of stable protein formulations that contain a protein at a higher concentration, such as at least about 80 mg/ml. In other aspects, the protein concentration is at least about 0.001 mg/ml, 0.005 mg/ml, 0.01 mg/ml, 0.05 mg/ml, 0.1 mg/ml, 0.5 mg/ml, 1 mg/ml, 1.5 mg/ml, 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9 mg/ml, 9.5 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 30 mg/ml, 35 mg/ml, 35 mg/ml, 40 mg/ml, 45 mg/ml, 50 mg/ml, 55 mg/ml, 60 mg/ml, 65 mg/ml, 65 mg/ml, 70 mg/ml, 75 mg/ml, 80 mg/ml, 85 mg/ml, 90 mg/ml, 95 mg/ml, 100 mg/mL, 105 mg/ml, 110 mg/ml, 115 mg/ml, 120 mg/ml, 125 mg/ml, 130 mg/ml, 135 mg/ml, 140 mg/ml, 145 mg/ml, 150 mg/ml, 155 mg/ml, 160 mg/ml, 165 mg/ml, 170 mg/ml, 175 mg/ml, 180 mg/ml, 185 mg/ml, 190 mg/ml, 195 mg/ml, 200 mg/ml, 205 mg/ml, 210 mg/ml, 215 mg/ml, 220 mg/ml, 225 mg/ml, 230 mg/ml, 235 mg/ml, 240 mg/ml, 245 mg/ml, 250 mg/ml, 250 mg/ml, 255 mg/ml, 260 mg/ml, 265 mg/ml, 270 mg/ml, 275 mg/ml, 280 mg/ml, 285 mg/ml, 290 mg/ml, 295 mg/ml, 300 mg/mL 305 mg/ml, 310 mg/ml, 315 mg/ml, 320 mg/ml, 325 mg/ml, 330 mg/ml, 335 mg/ml, 340 mg/ml, 345 mg/ml, 350 mg/ml, 355 mg/ml, 360 mg/ml, 365 mg/ml, 370 mg/ml, 375 mg/ml, 380 mg/ml, 385 mg/ml, 390 mg/ml, 395 mg/ml, 400 mg/ml, or more. In a further embodiment, the protein concentration is in the range of from about 50 mg/ml to about 400 mg/ml, 55 mg/ml to about 400 mg/ml, 60 mg/ml to about 400 mg/ml, 65 mg/ml to about 400 mg/ml, 65 mg/ml to about 400 mg/ml, 70 mg/ml to about 400 mg/ml, 75 mg/ml to about 400 mg/ml, 80 mg/ml to about 400 mg/ml, 85 mg/ml to about 400 mg/ml, 90 mg/ml to about 400 mg/ml, 95 mg/ml to about 400 mg/ml, 100 mg/mL to about 400 mg/ml, 105 mg/ml to about 400 mg/ml, 110 mg/ml to about 400 mg/ml, 115 mg/ml to about 400 mg/ml, 120 mg/ml to about 400 mg/ml, 125 mg/ml to about 400 mg/ml, 130 mg/ml to about 400 mg/ml, 135 mg/ml to about 400 mg/ml, 140 mg/ml to about 400 mg/ml, 145 mg/ml to about 400 mg/ml, 150 mg/ml to about 400 mg/ml, 155 mg/ml to about 400 mg/ml, 160 mg/ml to about 400 mg/ml, 165 mg/ml to about 400 mg/ml, 170 mg/ml to about 400 mg/ml, 175 mg/ml to about 400 mg/ml, 180 mg/ml to about 400 mg/ml, 185 mg/ml to about 400 mg/ml, 190 mg/ml to about 400 mg/ml, 195 mg/ml to about 400 mg/ml, 200 mg/ml to about 400 mg/ml, 205 mg/ml to about 400 mg/ml, 210 mg/ml to about 400 mg/ml, 215 mg/ml to about 400 mg/ml, 220 mg/ml to about 400 mg/ml, 225 mg/ml to about 400 mg/ml, 230 mg/ml to about 400 mg/ml, 235 mg/ml to about 400 mg/ml, 240 mg/ml to about 400 mg/ml, 245 mg/ml to about 400 mg/ml, 250 mg/ml to about 400 mg/ml, 250 mg/ml to about 400 mg/ml, 255 mg/ml to about 400 mg/ml, 260 mg/m to about 400 mg/m I, 265 mg/ml to about 400 mg/ml, 270 mg/ml to about 400 mg/ml, 275 mg/ml to about 400 mg/ml, 280 mg/ml to about 400 mg/ml, 285 mg/ml to about 400 mg/ml, 290 mg/ml to about 400 mg/ml, 295 mg/ml to about 400 mg/ml, 300 mg/mL to about 400 mg/ml, 305 mg/ml to about 400 mg/ml, 310 mg/ml to about 400 mg/ml, 315 mg/ml to about 400 mg/ml, 320 mg/ml to about 400 mg/ml, 325 mg/ml to about 400 mg/ml, 330 mg/ml to about 400 mg/ml, 335 mg/ml to about 400 mg/ml, 340 mg/ml to about 400 mg/ml, 345 mg/ml to about 400 mg/ml, 350 mg/ml to about 400 mg/ml, 355 mg/ml to about 400 mg/ml, 360 mg/ml to about 400 mg/ml to about 400 mg/ml, 365 mg/ml to about 400 mg/ml, 370 mg/ml to about 400 mg/ml, 375 mg/ml, 380 mg/ml to about 400 mg/ml, 385 mg/ml to about 400 mg/ml, 390 mg/ml to about 400 mg/ml, 395 mg/ml to about 400 mg/ml, 400 mg/ml. In a further embodiment, the protein concentration is at least 100 mg/ml to about 300 mg/ml, 150 mg/ml to about 300 mg/ml, 200 mg/ml to about 300 mg/ml, 250 mg/ml to about 300 mg/ml, 150 mg/ml to about 300 mg/mL, 150 mg/ml to about 250 mg/ml, 150 mg/ml to about 200 mg/ml or 200 mg/ml to about 300 mg/ml.

In still certain embodiments, the formulation includes two, or three, or four or more proteins (each of which may be selected from any of the examples set forth above or may be another protein). In one embodiment, the concentration of each of the proteins is at least about 100 mg/ml, or is at least about 130 mg/ml, 150 mg/ml, 200 mg/ml, 250 mg/ml, 300 mg/mL or at least 400 mg/ml and is still stable as assessed by one or more of the methods discussed above. In specific embodiments, the concentration of each protein is at least about 0.001 mg/ml, 0.005 mg/ml, 0.01 mg/ml, 0.05 mg/ml, 0.1 mg/ml, 0.5 mg/ml, 1 mg/ml, 1.5 mg/ml, 2 mg/ml, 2.5 mg/ml, 3 mg/ml, 3.5 mg/ml, 4 mg/ml, 4.5 mg/ml, 5 mg/ml, 5.5 mg/ml, 6 mg/ml, 6.5 mg/ml, 7 mg/ml, 7.5 mg/ml, 8 mg/ml, 8.5 mg/ml, 9 mg/ml, 9.5 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 30 mg/ml, 35 mg/ml, 35 mg/ml, 40 mg/ml, 45 mg/ml, 50 mg/ml, 55 mg/ml, 60 mg/ml, 65 mg/ml, 65 mg/ml, 70 mg/ml, 75 mg/ml, 80 mg/ml, 85 mg/ml, 90 mg/ml, 95 mg/ml, 100 mg/mL, 105 mg/ml, 110 mg/ml, 115 mg/ml, 120 mg/ml, 125 mg/ml, 130 mg/ml, 135 mg/ml, 140 mg/ml, 145 mg/ml, 150 mg/ml, 155 mg/ml, 160 mg/ml, 165 mg/ml, 170 mg/ml, 175 mg/ml, 180 mg/ml, 185 mg/ml, 190 mg/ml, 195 mg/ml, 200 mg/ml, 205 mg/ml, 210 mg/ml, 215 mg/ml, 220 mg/ml, 225 mg/ml, 230 mg/ml, 235 mg/ml, 240 mg/ml, 245 mg/ml, 250 mg/ml, 250 mg/ml, 255 mg/ml, 260 mg/ml, 265 mg/ml, 270 mg/ml, 275 mg/ml, 280 mg/ml, 285 mg/ml, 290 mg/ml, 295 mg/ml, 300 mg/mL 305 mg/ml, 310 mg/ml, 315 mg/ml, 320 mg/ml, 325 mg/ml, 330 mg/ml, 335 mg/ml, 340 mg/ml, 345 mg/ml, 350 mg/ml, 355 mg/ml, 360 mg/ml, 365 mg/ml, 370 mg/ml, 375 mg/ml, 380 mg/ml, 385 mg/ml, 390 mg/ml, 395 mg/ml, 400 mg/ml, or more. In a further embodiment, the protein concentration is in the range of from about 50 mg/ml to about 400 mg/ml, 55 mg/ml to about 400 mg/ml, 60 mg/ml to about 400 mg/ml, 65 mg/ml to about 400 mg/ml, 65 mg/ml to about 400 mg/ml, 70 mg/ml to about 400 mg/ml, 75 mg/ml to about 400 mg/ml, 80 mg/ml to about 400 mg/ml, 85 mg/ml to about 400 mg/ml, 90 mg/ml to about 400 mg/ml, 95 mg/ml to about 400 mg/ml, 100 mg/mL to about 400 mg/ml, 105 mg/ml to about 400 mg/ml, 110 mg/ml to about 400 mg/ml, 115 mg/ml to about 400 mg/ml, 120 mg/ml to about 400 mg/ml, 125 mg/ml to about 400 mg/ml, 130 mg/ml to about 400 mg/ml, 135 mg/ml to about 400 mg/ml, 140 mg/ml to about 400 mg/ml, 145 mg/ml to about 400 mg/ml, 150 mg/ml to about 400 mg/ml, 155 mg/ml to about 400 mg/ml, 160 mg/ml to about 400 mg/ml, 165 mg/ml to about 400 mg/ml, 170 mg/ml to about 400 mg/ml, 175 mg/ml to about 400 mg/ml, 180 mg/ml to about 400 mg/ml, 185 mg/ml to about 400 mg/ml, 190 mg/ml to about 400 mg/ml, 195 mg/ml to about 400 mg/ml, 200 mg/ml to about 400 mg/ml, 205 mg/ml to about 400 mg/ml, 210 mg/ml to about 400 mg/ml, 215 mg/ml to about 400 mg/ml, 220 mg/ml to about 400 mg/ml, 225 mg/ml to about 400 mg/ml, 230 mg/ml to about 400 mg/ml, 235 mg/ml to about 400 mg/ml, 240 mg/ml to about 400 mg/ml, 245 mg/ml to about 400 mg/ml, 250 mg/ml to about 400 mg/ml, 250 mg/ml to about 400 mg/ml to about 400 mg/ml, 255 mg/ml to about 400 mg/ml, 260 mg/m to about 400 mg/ml I, 265 mg/ml to about 400 mg/ml, 270 mg/ml to about 400 mg/ml, 275 mg/ml to about 400 mg/ml, 280 mg/ml to about 400 mg/ml, 285 mg/ml to about 400 mg/ml, 290 mg/ml to about 400 mg/ml, 295 mg/ml to about 400 mg/ml, 300 mg/mL to about 400 mg/ml, 305 mg/ml to about 400 mg/ml, 310 mg/ml to about 400 mg/ml, 315 mg/ml to about 400 mg/ml, 320 mg/ml to about 400 mg/ml, 325 mg/ml to about 400 mg/ml, 330 mg/ml to about 400 mg/ml, 335 mg/ml to about 400 mg/ml, 340 mg/ml to about 400 mg/ml, 345 mg/ml to about 400 mg/ml, 350 mg/ml to about 400 mg/ml, 355 mg/ml to about 400 mg/ml, 360 mg/ml to about 400 mg/ml to about 400 mg/ml, 365 mg/ml to about 400 mg/ml, 370 mg/ml to about 400 mg/ml, 375 mg/ml, 380 mg/ml to about 400 mg/ml, 385 mg/ml to about 400 mg/ml, 390 mg/ml to about 400 mg/ml, 395 mg/ml to about 400 mg/ml, 400 mg/ml. In a further embodiment, the protein concentration is at least 100 mg/ml to about 300 mg/ml, 150 mg/ml to about 300 mg/ml, 200 mg/ml to about 300 mg/ml, 250 mg/ml to about 300 mg/ml, 150 mg/ml to about 300 mg/mL, 150 mg/ml to about 250 mg/ml, 150 mg/ml to about 200 mg/ml or 200 mg/ml to about 300 mg/ml.

The amount, type, and proportion of amino acids can be determined empirically. In some embodiments, a suitable amino acid or amino acid combination may reversibly neutralize any deleterious hydrophobicity from hydrophobic residues found on the surface of the subject bioactive protein. In solution, a protein's tertiary conformation is dynamic, there may be at any given time particular amino acid residues exposed to the water solvent. Thus, polar amino acids, or their mimetics as described below, may be particularly useful as a type of competitive antagonist blocking such exposed hydrophobic regions from protein-protein interaction. Moreover, in embodiments that include some proportion of hydrophobic amino acid monomers, those monomers may act to interfere with non-hydrophilic regions to prevent protein-protein deleterious effects.

As provided above, in one embodiment, each amino acid may be present at a concentration of at least about 0.1% (w/v), or alternatively at least about at about 0.01% to about 25%, 0.02% to about 25%, 0.05% to about 25%, 0.075% to about 25%, 0.2% to about 25%, 0.3% to about 25%, 0.4% to about 25%, 0.5% to about 25%, 0.6% to about 25%, 0.7% to about 25%, 0.8% to about 25%, 0.9% to about 25%, 1% to about 25%, 1.5% to about 25%, 1.75% to about 25%, 2% to about 25%, 2.25% to about 25%, 2.5% to about 25%, 2.75% to about 25%, 3% to about 25%, 3.25% to about 25%, 3.5% to about 25%, 3.75% to about 25%, 4% to about 25%, 4.25% to about 25%, 4.5% to about 25%, 4.75% to about 25%, 5% to about 25%, 5.25% to about 25%, 5.5% to about 25%, 5.75% to about 25%, 6% to about 25%, 6.25% to about 25%, 6.5% to about 25%, 6.75% to about 25%, 7% to about 25%, 7.25% to about 25%, 7.5% to about 25%, 7.75% to about 25%, 8% to about 25%, 8.25% to about 25%, 8.5% to about 25%, 8.75% to about 25%, 9% to about 25%, 9.25% to about 25%, 9.5% to about 25%, 9.75% to about 25%, 10% to about 25%, 10.25% to about 25%, 10.5% to about 25%, 10.75% to about 25%, 11% to about 25%, 11.25% to about 25%, 11.5% to about 25%, 11.75% to about 25%, 12% to about 25%, 12.25% to about 25%, 12.5% to about 25%, 12.75% to about 25%, 13% to about 25%, 13.25% to about 25%, 13.5% to about 25%, 13.75% to about 25%, 14% to about 25%, 14.25% to about 25%, 14.5% to about 25%, 14.75% to about 25%, 15% to about 25%, 15.25% to about 25%, 15.5% to about 25%, 15.75% to about 25%, 16% to about 25%, 16.25% to about 25%, 16.5% to about 25%, 16.75% to about 25%, 17% to about 25%, 17.25% to about 25%, 17.5% to about 25%, 17.75% to about 25%, 18% to about 25%, 18.25% to about 25%, 18.5% to about 25%, 18.75% to about 25%, 19% to about 25%, 19.25% to about 25%, 19.5% to about 25%, 19.75% to about 25%, 20% to about 25%, 20.25% to about 25%, 20.5% to about 25%, 20.75% to about 25%, 5% to about 20%, 6% to about 20%, 7% to about 20%, 8% to about 20%, 9% to about 20%, 10% to about 20%, 11% to about 20%, 12% to about 20%, 13%, to about 20%, 14% to about 20%, 15% to about 20%, 5% to about 15%, 6% to about 15%, 7% to about 15%, 8% to about 15%, 9% to about 15%, 10% to about 15%, 11% to about 15%, 12% to about 15%, 13%, to about 15%, 14% to about 15% (w/v). Still further, in an additional embodiment, each amino acid may be present at a concentration of between about 1 mg/ml to about 100 mg/ml, or between about 1 mg/ml to about 20 mg/ml, or between about 1.5 mg/ml to about 10 mg/ml, or between about 2 mg/ml to about 10 mg/ml, or between about 3 mg/ml to about 8 mg/ml, such as between 1 mg/ml to about 100 mg/ml, or between 1 mg/ml to about 20 mg/ml, or between 1.5 mg/ml to about 10 mg/ml, or between 2 mg/ml to about 10 mg/ml, or between 3 mg/ml to about 8 mg/ml. In a particular embodiment, each amino acid is present in concentrations between about 0.13 to about 30 mg/ml, such as between 0.13 to about 30 mg/mi. In an embodiment, each amino acid may be present at a concentration of at least about 0.01 mg/ml, 0.1 mg/ml, 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 21 mg/ml, 22 mg/ml, 23 mg/ml, 24 mg/ml, 25 mg/ml, 26 mg/ml, 27 mg/ml, 28 mg/ml, 29 mg/ml, 30 mg/ml, 31 mg/ml, 32 mg/ml, 33 mg/ml, 34 mg/ml, 35 mg/ml, 36 mg/ml, 37 mg/ml, 38 mg/ml, 39 mg/ml, 40 mg/ml, 41 mg/ml, 42 mg/ml, 43 mg/ml, 44 mg/ml, 45 mg/ml, 46 mg/ml, 47 mg/ml, 48 mg/ml, 49 mg/ml, 50 mg/ml, 51 mg/ml, 52 mg/ml, 53 mg/ml, 54 mg/ml, 55 mg/ml, 56 mg/ml, 57 mg/ml, 58 mg/ml, 59 mg/ml, 60 mg/ml, 61 mg/ml, 62 mg/ml, 63 mg/ml, 64 mg/ml, 65 mg/ml, 66 mg/ml, 67 mg/ml, 68 mg/ml, 69 mg/ml, 70 mg/ml, 71 mg/ml, 72 mg/ml, 73 mg/ml, 74 mg/ml, 75 mg/ml, 76 mg/ml, 77 mg/ml, 78 mg/ml, 79 mg/ml, 80 mg/ml, 81 mg/ml, 82 mg/ml, 83 mg/ml, 84 mg/ml, 85 mg/ml, 86 mg/ml, 87 mg/ml, 88 mg/ml, 89 mg/ml, 90 mg/ml, 91 mg/ml, 92 mg/ml, 93 mg/ml, 94 mg/ml, 95 mg/ml, 96 mg/ml, 97 mg/ml, 98 mg/ml, 99 mg/ml, 100 mg/ml, 105 mg/ml, 110 mg/ml, 115 mg/ml, 120 mg/ml, 125 mg/ml, 130 mg/ml, 135 mg/ml, 140 mg/ml, 145 mg/ml, 150 mg/ml, 155 mg/ml, 160 mg/ml, 165 mg/ml, 170 mg/ml, 175 mg/ml, 180 mg/ml, 185 mg/ml, 190 mg/ml, 195 mg/ml, 200 mg/ml, 210 mg/ml, 220 mg/ml, 225 mg/ml, 230 mg/ml, 240 mg/ml, 250 mg/ml, 260 mg/ml, 270 mg/ml, 280 mg/ml, 290 mg/ml, 300 mg/ml, 325 mg/ml, 350 mg/ml, 375 mg/ml, 400 mg/ml, or any combination thereof.

In one embodiment, any formulation as described herein is in a liquid form. In another embodiment, any formulation as described herein is provided in a container closure system that is a prefilled syringe. In an embodiment, any formulation as described herein is in a solid form. In another embodiment, any formulation as described herein is provided in a container closer system as a solid. In an additional embodiment, a solid formulation is a lyophilized solid formulation that is formed using lyophilization techniques well known in the art.

In one embodiment, a protein has, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95% of its biological activity relative to native unmodified protein. In other aspects of this embodiment, a protein has, e.g., about 10% to about 100%, about 20% to about 100%, about 30% to about 100%, about 40% to about 100%, about 50% to about 100%, about 60% to about 100%, about 70% to about 100%, about 80% to about 100%, about 10% to about 90%, about 20% to about 90%, about 30% to about 90%, about 40% to about 90%, about 50% to about 90%, about 60% to about 90%, about 70% to about 90%, about 10% to about 80%, about 20% to about 80%, about 30% to about 80%, about 40% to about 80%, about 50% to about 80%, or about 60% to about 80%, about 10% to about 70%, about 20% to about 70%, about 30% to about 70%, about 40% to about 70%, or about 50% to about 70% of its biological activity relative to native unmodified protein.

In an embodiment, a protein is administered at a dose to a human or an animal to treat a disorder is in the range of at least 0.001 mg/kg/day, at least 0.01 mg/kg/day, at least 0.1 mg/kg/day, at least 1.0 mg/kg/day, at least 5.0 mg/kg/day, at least 10 mg/kg/day, at least 15 mg/kg/day, at least 20 mg/kg/day, at least 25 mg/kg/day, at least 30 mg/kg/day, at least 35 mg/kg/day, at least 40 mg/kg/day, at least 45 mg/kg/day, or at least 50 mg/kg/day or in the range of about 0.001 mg/kg/day to about 100 mg/kg/day or in the range of about 0.001 mg/kg/day to about 10 mg/kg/day, about 0.001 mg/kg/day to about 15 mg/kg/day, about 0.001 mg/kg/day to about 20 mg/kg/day, about 0.001 mg/kg/day to about 25 mg/kg/day, about 0.001 mg/kg/day to about 30 mg/kg/day, about 0.001 mg/kg/day to about 35 mg/kg/day, about 0.001 mg/kg/day to about 40 mg/kg/day, about 0.001 mg/kg/day to about 45 mg/kg/day, about 0.001 mg/kg/day to about 50 mg/kg/day, about 0.001 mg/kg/day to about 75 mg/kg/day, or about 0.001 mg/kg/day to about 100 mg/kg/day. In a further embodiment, a protein is administered at a dose to a human or animal to treat a disorder is at a concentration of at least 0.001 mg, 0.005 mg, 0.001 mg, 0.05 mg, 0.01 mg, 0.5 mg, 0.1 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 10 8 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, v92 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 329 mg, 240 mg, 241 mg, 242 mg, 243 mg, 244 mg, 245 mg, 246 mg, 250 mg, 251 mg, 252 mg, 253 mg, 254 mg, 255 mg, 256 mg, 257 mg, 258 mg, 259 mg, 260 mg, 261 mg, 262 mg, 263 mg, 264 mg, 265 mg, 266 mg, 267 mg, 268 mg, 269 mg, 270 mg, 271 mg, 272 mg, 273 mg, 274 mg, 275 mg, 276 mg, 277 mg, 278 mg, 279 mg, 280 mg, 281 mg, 282 mg, 283 mg, 284 mg, 285 mg, 286 mg, 287 mg, 288 mg, 289 mg, 290 mg, 291 mg, 292 mg, 293 mg, 294 mg, 295 mg, 296 mg, 297 mg, 298 mg, 299 mg, 300 mg, 310 mg, 320 mg, 330 mg, 340 mg, 350 mg, 360 mg, 370 mg, 380 mg, 390 mg, 400 mg, 410 mg, 420 mg, 430 mg, 440 mg, 450 mg, 460 mg, 470 mg, 480 mg, 490 mg, 500 mg, or more.

In an embodiment, the protein can be an extended half-life form. Extended half-life forms can be prepared by linking a water soluble polymer to a protein through either a stable or a releasable linkage. In an embodiment, an extended half-life form is a fusion protein, a truncated protein, a protein with a modified carbohydrate pattern, a protein wherein amino acids have been replaced or other nonnative protein. In an embodiment, the water soluble polymer is, without limitation selected from the group consisting of carbohydrate, polysaccharides, pullulane, chitosan, hyaluronic acid, chondroitin sulfate, dermatan sulfate, starch, dextran, carboxymethyl-dextran, polyalkylene oxide (PAO), polyalkylene glycol (PAG), polypropylene glycol (PPG), polyoxazoline, polyacryloylmorpholine, polyvinyl alcohol (PVA), polyethylene glycol (PEG), branched PEG, POLYPEG®, polysialic acid (PSA), starch, hydroxyalkyl starch (HAS), hydroxyethyl starch (HES), polycarboxylate, polyvinylpyrrolidone, polyphosphazene, polyoxazoline, polyethylene-co-maleic acid anhydride, polystyrene-co-maleic acid anhydride, poly(1-hydroxymethylethylene hydroxymethylformal) (PHF), 2-methacryloyloxy-2'-ethyltrimethylammoniumphosphate (MPC). In an embodiment the protein-water soluble polymer conjugate has a biological activity of at least 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, or 150 percent (%) biological activity relative to native unmodified protein. In a further embodiment, the water soluble polymer is from about 1,000 kD to about 150,000 kD, from about 2,000 kD to about 125,000 kD, from about 3,000 kD to about 100,000 kD, from about 4,000 kD to about 100,000 kD, from about 5,000 kD to about 100,000 kD, from about 10,000 kD to about 100,000 kD, from about 15,000 kD to about 100,000 kD, from about 20,000 kD to about 100,000 kD, from about 25,000 kD to about 100,000 kD, from about 30,000 kD to about 100,000 kD, from about 35,000 kD to about 100,000 kD, from about 40,000 kD to about 100,000 kD, from about 50,000 kD to about 1000,000 kD. In an embodiment the water soluble polymer is at least 250 kD, 500 kD, 750 kD, 1000 kD, 1,250 kD, 1500 kD, 1,750 kD, 2,000 kD, 2,500 kD, 3,000 kD, 3,500 kD, 4,000 kD, 4,500 kD, 5,000 kD 5,500 kD, 6,000 kD, 6,500 kD, 7,000 kD, 7,500 kD, 8,000 kD, 8,500 kD, 9,000 kD, 9500 kD, 10,000 kD, 11,000 kD, 12,000 kD, 13,000 kD, 14,000 kD, 15,000 kD, 16,000 kD, 17,000 kD, 18,000 kD, 19,000 kD, 20,000 kD, 25,000 kD, 30,000 kD, 35,000 kD, 40,000 kD, 45,000 kD, 50,000 kD, 60,000 kD, 70,000 kD, 80,000 kD, 90,000 kD, 100,00 kD, 110,000 kD, 120,000 kD, 130,000 kD, 140,000 kD, 150,000 kD or any combination thereof.

In an embodiment, viscosity is measured in centipoise (cP). In an embodiment, viscosity is measured in milli pascal seconds (mpas). In an embodiment, the viscosity of the solution in mpas is less than 250 mpas, 200 mpas, 150 mpas, 100 mpas, 90 mpas, 80 mpas, 70 mpas, 60 mpas, 50 mpas, 40 mpas, 30 mpas, 25 mpas, 24 mpas, 23 mpas, 22 mpas, 21 mpas, 20 mpas, 19 mpas, 18 mpas, 17 mpas, 16 mpas, 15 mpas, 14 mpas, 13 mpas, 12 mpas, 11 mpas, 10 mpas, 9 mpas, 8 mpas, 7 mpas, 6 mpas, 5 mpas, 4 mpas, 3 mpas, 2 mpas or 1 mpas. In an embodiment, the viscosity of the solution in cP is less than 250 cP, 200 cP, 150 cP, 100 cP, 90 cP, 80 cP, 70 cP, 60 cP, 50 cP, 40 cP, 30 cP, 25 cP, 24 cP, 23 cP, 22 cP, 21 cP, 20 cP, 19 cP, 18 cP, 17 cP, 16 cP, 15 m cP, 14 cP, 13 cP, 12 cP, 11 cP, 10 cP, 9 cP, 8 cP, 7 cP, 6 cP, 5 cP, 4 cP, 3 cP, 2 cP, or 1 cP.

In an embodiment, a pharmaceutical formulation is comprised of an active biological agent and a soluble formulation within which the active biological agent is dissolved. In some embodiments, the soluble formulation is a formulation as described herein to further include, without limitation, one or more excipients, such as buffers, tonicity modifiers, bulking agents, metal ions, chelating agents, surfactants, stabilizers, polymers, viscosity reducing agents, salts, sugars, etc. As used herein, the term "excipient" refers, without limitation, to an inert substance which is commonly used as a diluent, vehicle, preservative, binder, or stabilizing agent for drugs and includes, but is not limited to, proteins (e.g., serum albumin, etc.), fatty acids and phospholipids (e.g., alkyl sulfonates, caprylate, etc.), surfactants (e.g., polysorbate, poloxamer, nonionic surfactant, etc.), saccharides (e.g., sucrose, maltose, trehalose, etc.) and polyols (e.g., mannitol, sorbitol, etc.). Also see Remington's Pharmaceutical Sciences (by Joseph P. Remington, 18th ed., Mack Publishing Co., Easton, Pa.) and Handbook of Pharmaceutical Excipients (by Raymond C. Rowe, 5th ed., APhA Publications, Washington, D.C.) which are hereby incorporated in its entirety. The excipients may impart a beneficial physical property to the formulation, such as increased protein stability, increased protein solubility and decreased viscosity.

In an embodiment, a pharmaceutical composition of the invention, including, without limitation a therapeutic compound, may include one or more carbohydrates such as a sugar, a derivatized sugar such as an alditol, aldonic acid, an esterified sugar, and/or a sugar polymer. Specific carbohydrate excipients include, for example, without limitation: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

In an embodiment, pharmaceutical compositions of the invention, including, without limitation, a therapeutic compound, are potato and corn-based starches such as sodium starch glycolate and directly compressible modified starch. In an embodiment, syrups and elixirs may be formulated, without limitation, sweetening agents, for example glycerol, propylene glycol, sorbitol or sucrose. In an additional embodiment, such formulations may also contain, without limitation, a demulcent, a preservative, flavoring agents, and coloring agents.

In an embodiment, liquid suspensions may be formulated, without limitation, by suspending a therapeutic compound disclosed herein in admixture with excipients suitable for the manufacture of aqueous suspensions. In an embodiment, such excipients are suspending agents, for example, without limitation, sodium carboxymethylcellulose, methylcellulose, hydroxypropylmethylcellulose, sodium alginate, pectin, polyvinyl pyrrolidone, polyvinyl alcohol, natural gum, agar, gum tragacanth and gum acacia; dispersing or wetting agents may be a naturally occurring phosphatide, for example lecithin, or condensation products of an alkylene oxide with fatty acids, for example, without limitation, polyoxyethylene stearate, or condensation products of ethylene oxide with long-chain aliphatic alcohols, for example, without limitation, heptadecaethyleneoxycetanol, or condensation products of ethylene oxide with partial esters derived from fatty acids, for example, without limitation, polyoxyethylene sorbitan monooleate.

Particular excipients as approved for U.S. Food and Drug regulatory purposes can be found at the FDA Inactive Ingredient Database. Many useful excipients are well known in the art and can be found described in, for example, Banga, A. K., Therapeutic Peptides and Proteins, Formulation, Processing and Delivery Systems, (2d Ed 2006, CRC Press), Chapter 4, section 4.4, Pharmaceutical excipients in formulations (at pages 104-116). Any one or more of any other excipients or others may be included in any formulation as described herein. Similarly, in an embodiment, at least one excipient can confer more than one of the functions onto a formulation. Alternatively, in another embodiment, two or more excipients can be included in a formulation to perform more than one of the above or other functions. For example, an excipient can, without limitation, be included as a component in a formulation to change, adjust or optimize the osmolality of the formulation, thereby acting as a tonicity modifier.

Given the teachings and guidance provided herein, those skilled in the art will understand that a formulation described herein can be equally applicable to many types of biopharmaceuticals, including those exemplified, as well as others known in the art. Given the teachings and guidance provided herein, those skilled in the art also will understand that the selection of, for example, type(s) or and/or amount(s) of one or more excipients, surfactants and/or optional components can be made based on the chemical and functional compatibility with the biopharmaceutical to be formulated and/or the mode of administration as well as other chemical, functional, physiological and/or medical factors well known in the art. For example, non-reducing sugars exhibit favorable excipient properties when used with polypeptide biopharmaceuticals compared to reducing sugars. Accordingly, exemplary formulations are exemplified further herein with reference to polypeptide biopharmaceuticals. However, the range of applicability, chemical and physical properties, considerations and methodology applied to polypeptide biopharmaceutical can be similarly applicable to biopharmaceuticals other than polypeptide biopharmaceuticals.

In various embodiments, a formulation can include, without limitation, combinations of bioactive agents (such as proteins, antibodies and the like as described herein) in the formulation. For example, a formulation as described herein can include a single bioactive agent for treatment of one or more conditions, including without limitation, disease. A formulation as described herein also can include, in an embodiment, without limitation, two or more different bioactive agents for a single or multiple conditions. Use of multiple bioactive agents in a formulation can be directed to, for example, the same or different indications. Similarly, in another embodiment, multiple bioactive agents can be used in a formulation to treat, for example, both a pathological condition and one or more side effects caused by the primary treatment. In a further embodiment, multiple bioactive agents also can be included, without limitation, in a formulation as described herein to accomplish different medical purposes including, for example, simultaneous treatment and monitoring of the progression of the pathological condition. In an additional embodiment, multiple, concurrent therapies such as those exemplified herein as well as other combinations well known in the art are particularly useful for patient compliance because a single formulation can be sufficient for some or all suggested treatments and/or diagnosis. Those skilled in the art will know those bioactive agents that can be admixed for a wide range of combination therapies. Similarly, in various embodiments, a formulation can be used with a small molecule drug and combinations of one or more bioactive agents s together with one or more small molecule pharmaceuticals. Therefore, in various embodiments a formulation is provided containing 1, 2, 3, 4, 5 or 6 or more different bioactive agents, as well as, for one or more bioactive agents combined with one or more small molecule pharmaceuticals.

In various embodiments, a formulation can include, without limitation, one or more preservatives and/or additives known in the art. Similarly, a formulation can further be formulated, without limitation, into any of various known delivery formulations. For example, in an embodiment, a formulation can include, without limitation, surfactants, adjuvant, biodegradable polymers, hydrogels, etc. Such optional components, their chemical and functional characteristics are known in the art. Similarly known in the art are formulations that facilitate rapid, sustained or delayed release of the bioactive agents after administration. A formulation as described can be produced to include these or other formulation components known in the art.

Once a formulation is prepared as described herein, stability of the one or more bioactive agents contained within the formulation can be assessed using methods known in the art. Several methods are exemplified herein in the Examples and include size exclusion chromatography, particle counting and cation exchange chromatography. Other methods can comprise any of a variety of functional assays including, for example, binding activity, other biochemical activity and/or physiological activity can be assessed at two or more different time points to determine the stability of the bioactive agents in a formulation as described herein. A formulation can, in general, be prepared according to pharmaceutical standards and using pharmaceutical grade reagents. Similarly, a formulation can be prepared using sterile reagents in a sterile manufacturing environment or sterilized following preparation. Sterile injectable solutions can be prepared using known procedures in the art including, for example, by incorporating one or more bioactive agents s in the required amount in a glutamic acid buffer or excipient with one or a combination of formulation components described herein followed by sterilization microfiltration. In various embodiments, sterile powders for the preparation of sterile injectable solutions can include, for example, vacuum drying and freeze-drying (lyophilization). Such drying methods will yield a powder of the one or more bioactive agents s together with any additional desired components from a previously sterile-filtered solution thereof.

In an embodiment, further representative excipients include, without limitation, inorganic salt or buffers such as citric acid, sodium chloride, potassium chloride, sodium sulfate, potassium nitrate, sodium phosphate monobasic, sodium phosphate dibasic, and combinations thereof. In an embodiment, the safety and effectiveness of any formulation may be evaluated in an animal model system predictive of efficacy for the targeted condition in human. Alternatively, in another embodiment, the ability of a formulation to reduce or inhibit a symptom can be evaluated, for example, by examining an in vitro function or activity of the formulation indicative of in vivo therapeutic activity.

In an embodiment, formulations suitable for nasal administration, wherein the carrier is a solid, include, without limitation, a coarse powder having a particle size, for example, without limitation, in the range of about 20 to about 500 microns. In a further embodiment, particle size is, without limitation, at least, 10 microns, 20 microns, 30 microns, 40 microns, 50 microns, 60 microns, 70 microns, 80 microns, 90 microns, 100 microns, 110 microns, 120 microns, 130 microns, 140 microns, 150 microns, 160 microns, 170 microns, 180 microns, 190 microns, 200 microns, 210 microns, 220 microns, 230 microns, 240 microns, 250 microns, 260 microns, 270 microns, 280 microns, 290 microns, 300 microns, 310 microns, 320 microns, 330 microns, 340 microns, 350 microns, 360 microns, 370 microns, 380 microns, 390 microns, 400 microns, 410 microns, 420 microns, 430 microns, 440 microns, 450 microns, 460 microns, 470 microns, 480 microns, 490 microns, 500 microns, 600 microns, 700 microns, 800 microns, 900 microns, 1000 microns. In an additional embodiment, such a formulation is typically administered, without limitation, by rapid inhalation through the nasal passage, for example, without limitation, from a container of the powder held in proximity to the nose. In an additional embodiment, such a formulation is typically administered, without limitation, by rapid inhalation through the mouth, for example, without limitation, from a container of the powder held in proximity to the mouth. In an embodiment, a formulation for nasal delivery may be, without limitation, in the form of a liquid, e.g., a nasal spray or nasal drops.

In an embodiment, aerosolizable formulations for inhalation may be, without limitation, in dry powder form (e.g., suitable for administration by a dry powder inhaler), or, alternatively, may be in liquid form, e.g., for use in a nebulizer. In an embodiment, nebulizers for delivering an aerosolized solution include, without limitation, the AERX™ (Aradigm), the ULTRAVENT® (Mallinkrodt), and the ACORN II® (Marquest Medical Products). In an embodiment, a composition of the invention may also, without limitation, be delivered using a pressurized, metered dose inhaler (MDI), e.g., the VENTOLIN® metered dose inhaler, containing a solution or suspension of a combination of drugs as described herein in a pharmaceutically inert liquid propellant, for example, without limitation, a chlorofluorocarbon or fluorocarbon.

In an embodiment, formulations suitable for parenteral administration include, without limitation, aqueous and non-aqueous isotonic sterile solutions suitable for injection, as well as aqueous and non-aqueous sterile suspensions. In an embodiment, parenteral formulations of the invention are optionally contained, without limitation, in unit-dose or multi-dose sealed containers, for example, without limitation, ampoules and vials, and may be stored in a freeze-dried (lyophilized) condition requiring only the addition of the sterile liquid carrier, for example, water for injections, immediately prior to use. In an embodiment, extemporaneous injection solutions and suspensions may be prepared, without limitation, from sterile powders, granules, capsules, geltabs, caplets and tablets of the types previously described.

The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data. In various embodiments, the bioactive agents in formulations described herein can, without limitation, be administered to patients throughout an extended time period, such as chronic administration for a chronic condition. The composition can be, without limitation a solid, a semi-solid or an aerosol and a therapeutic compound is formulated as a tablet, geltab, lozenge, orally dissolved strip, capsule, syrup, oral suspension, emulsion, granule, sprinkle or pellet.

In an embodiment, a drug delivery platform includes both a sustained release drug delivery platform and an extended release drug delivery platform. In an embodiment, the term "sustained release" refers to the release of a therapeutic compound or compounds disclosed herein over a period of about seven days or more. In an embodiment, the term "extended release" refers to the release of a therapeutic compound or compounds disclosed herein over a period of time of less than about seven days. In an embodiment, a sustained release drug delivery platform releases a therapeutic compound or compounds disclosed herein with substantially zero order release kinetics over a period of, without limitation, about 3 days after administration, about 7 days after administration, about 10 days after administration, about 15 days after administration, about 20 days after administration, about 25 days after administration, about 30 days after administration, about 45 days after administration, about 60 days after administration, about 75 days after administration, or about 90 days after administration. In another embodiment, a sustained release drug delivery platform releases a therapeutic compound disclosed herein with substantially zero order release kinetics over a period, without limitation, at least 3 days after administration, at least 7 days after administration, at least 10 days after administration, at least 15 days after administration, at least 20 days after administration, at least 25 days after administration, at least 30 days after administration, at least 45 days after administration, at least 60 days after administration, at least 75 days after administration, or at least 90 days after administration.

In an embodiment, for oral, rectal, vaginal, parenteral, pulmonary, sublingual and/or intranasal delivery formulations, tablets can be made by compression or molding, optionally with one or more accessory ingredients or additives. In an embodiment, compressed tablets are prepared, for example, by compressing in a suitable tabletting machine, the active ingredients in a free-flowing form such as a powder or granules, optionally mixed with a binder (for example, without limitation, povidone, gelatin, hydroxypropylmethyl cellulose), lubricant, inert diluent, preservative, disintegrant (for example, without limitation, sodium starch glycolate, cross-linked povidone, cross-linked sodium carboxymethyl cellulose) and/or surface-active or dispersing agent.

In an embodiment, molded tablets are made, for example, without limitation, by molding in a suitable tabletting machine, a mixture of powdered compounds moistened with an inert liquid diluent. In an embodiment, the tablets may optionally be coated or scored, and may be formulated so as to provide slow or controlled release of the active ingredients, using, for example, without limitation, hydroxypropylmethyl cellulose in varying proportions to provide the desired release profile. In an embodiment, tablets may optionally be provided with a coating, without limitation, such as a thin film, sugar coating, or an enteric coating to provide release in parts of the gut other than the stomach. In an embodiment, processes, equipment, and toll manufacturers for tablet and capsule making are well-known in the art.

In an embodiment, capsule formulations may utilize, without limitation, either hard or soft capsules, including, without limitation, gelatin capsules or vegetarian capsules such as those made out of hydroxymethylpropylcellulose (HMPC). In an embodiment, a type of capsule is a gelatin capsule. In an embodiment, capsules may be filled using a capsule filling machine such as, without limitation, those available from commercial suppliers such as Miranda International or employing capsule manufacturing techniques well-known in the industry, as described in detail in Pharmaceutical Capules, 2.sup.nd Ed., F. Podczeck and B. Jones, 2004. In an embodiment, capsule formulations may be prepared, without limitation, using a toll manufacturing center such as the Chao Center for Industrial Pharmacy & Contract Manufacturing, located at Purdue Research Park.

The formulation described in this specification may also comprise more than one therapeutic protein as desired for the particular indication being treated, preferably those with complementary activities that do not adversely affect the other proteins. The formulations to be used for in vivo administration can be sterile. This can be accomplished, for instance, without limitation, by filtration through sterile filtration membranes, prior to, or following, preparation of the formulation or other methods known in the art, including without limitation, pasteurization.

Packaging and instruments for administration may be determined by a variety of considerations, such as, without limitation, the volume of material to be administered, the conditions for storage, whether skilled healthcare practitioners will administer or patient self-compliance, the dosage regime, the geopolitical environment (e.g., exposure to extreme conditions of temperature for developing nations), and other practical considerations.

Injection devices include pen injectors, auto injectors, safety syringes, injection pumps, infusion pumps, glass prefilled syringes, plastic prefilled syringes and needle free injectors syringes may be prefilled with liquid, or may be dual chambered, for example, for use with lyophilized material. An example of a syringe for such use is the LYO JECT™, a dual-chamber pre-filled lyosyringe available from Vetter GmbH, Ravensburg, Germany. Another example is the LYOTIP™ which is a prefilled syringe designed to conveniently deliver lyophilized formulations available from LyoTip, Inc., Camarillo, Calif., U.S.A. Administration by injection may be, without limitation intravenous, intramuscular, intraperitoneal, or subcutaneous, as appropriate. Administrations by non-injection route may be, without limitation, nasal, oral, cooular, dermal, or pulmonary, as appropriate.

In certain embodiments, kits can comprise, without limitation, one or more single or multi-chambered syringes (e.g., liquid syringes and lyosyringes) for administering one or more formulations described herein. In various embodiments, the kit can comprise formulation components for parenteral, subcutaneous, intramuscular or IV administration, sealed in a vial under partial vacuum in a form ready for loading into a syringe and administration to a subject. In this regard, the composition can be disposed therein under partial vacuum. In all of these embodiments and others, the kits can contain one or more vials in accordance with any of the foregoing, wherein each vial contains a single unit dose for administration to a subject.

The kits can comprise lyophilates, disposed as herein, that upon reconstitution provide compositions in accordance therewith. In various embodiment the kits can contain a lyophilate and a sterile diluent for reconstituting the lyophilate.

Imaging components can optionally be included and the packaging also can include written or web-accessible instructions for using the formulation. A container can include, for example, a vial, bottle, syringe, pre-filled syringe or any of a variety of formats well known in the art for multi-dispenser packaging.

Also described herein, are methods for treating a subject in need of therapy, comprising administering to the subject an effective amount of a formulation as described herein. The therapeutically effective amount or dose of a formulation will depend on the disease or condition of the subject and actual clinical setting.

In an embodiment, a "pharmaceutical composition" is intended to include, without limitation, the combination of an active agent with a carrier, inert or active, in a sterile composition suitable for diagnostic or therapeutic use in vitro, in vivo or ex vivo. In one aspect, the pharmaceutical composition is substantially free of endotoxins or is non-toxic to recipients at the dosage or concentration employed.

In an embodiment, "an effective amount" refers, without limitation, to the amount of the defined component sufficient to achieve the desired chemical composition or the desired biological and/or therapeutic result. In an embodiment, that result can be the desired pH or chemical or biological characteristic, e.g., stability of the formulation. In other embodiments, the desired result is the alleviation of the signs, symptoms, or causes of a disease, or any other desired alteration of a biological system. When the desired result is a therapeutic response, the effective amount will, without limitation, vary depending upon the specific disease or symptom to be treated or alleviated, the age, gender and weight of the subject to be treated, the dosing regimen of the formulation, the severity of the disease condition, the manner of administration and the like, all of which can be determined readily by one of skill in the art.

In an embodiment, a "subject" of diagnosis or treatment is, without limitation, a prokaryotic or a eukaryotic cell, a tissue culture, a tissue or an animal, e.g. a mammal, including a human. Non-human animals subject to diagnosis or treatment include, for example, without limitation, a simian, a murine, a canine, a leporid, such as a rabbit, livestock, sport animals, and pets.

In an embodiment, as used herein, the terms "treating," "treatment" and the like are used herein, without limitation, to mean obtaining a desired pharmacologic and/or physiologic effect. The effect may be prophylactic in terms of completely or partially preventing a disorder or sign or symptom thereof, and/or may be therapeutic in terms of amelioration of the symptoms of the disease or infection, or a partial or complete cure for a disorder and/or adverse effect attributable to the disorder. In one embodiment, the formulations containing an antibodies will, without limitation. prevent or alleviate or mitigate the symptoms of a disease or condition in a subject.

In an embodiment, a formulation as described herein can be administered by any suitable route, specifically by parental (including subcutaneous, intramuscular, intravenous and intradermal) administration. It will also be appreciated that the preferred route will vary with the condition and age of the recipient, and the disease being treated. Methods of determining the most effective means and dosage of administration are known to those of skill in the art and will vary, without limitation, with the composition used for therapy, the purpose of the therapy, and the subject being treated. Single or multiple administrations can be carried out, without limitation, the dose level and pattern being selected by the treating physician. Suitable dosage formulations and methods of administering the agents are known in the art.

The formulations as described herein can be used in the manufacture of medicaments and for the treatment of humans and other animals by administration in accordance with conventional procedures.

Also provided herein are combinatorial methods for developing suitable protein formulations using combinations of amino acids. These methods are effective for developing high concentration, low viscosity, stable liquid protein formulations, and particularly pharmaceutical protein formulations.

The general process for developing a formulation is discussed below. The process can be divided into three parts: Preformulation Characterization, High Throughput Screening and Long-Term Stability Confirmation.

Preformulation characterization studies generally are designed to understand pharmaceutically significant physicochemical properties of the formulant, such as stability when exposed to common stresses, developing assays for degradation products and other measures of stability, determining if a lyophilized or liquid formulation will be better for initial clinical studies, and developing a final research protocol. Preformulation characterization generally involves physiochemical characterization, stability assay development and stress studies to identify formulation and stability problems and facilitate optimization studies.

High throughput screening typically is used to test a large number of possible formulations to identify a limited number of candidates for development. Most degradation reactions of proteins to evaluate stablity, e.g., aggregation or precipitation, can be accelerated by increasing the temperature. Similarly, viscosity can be evaluated through several methods, without limitation, pushing the protein solution through a syringe, for example, without limitation, a 30 gauge needle, at relatively constant plunger pressure. It can be important, however, that the incubation temperature is kept below the respective protein's thermal denaturation temperature so that the aggregation of the protein with intact secondary structure is determined. A high throughput screening protocol can be developed based on critical issues observed at the preformulation characterization. Forced degradation may be used to expedite the relevant degradation pathway(s). Effective stabilizers or their combinations, e.g., amino acids, are identified by the high throughput screening.

A small number of promising formulations may be selected and tested for long term stability. For example, samples formulated with the selected stabilizer(s) can be prepared in appropriate container/closure system, incubated at appropriate storage conditions or expose other relevant stresses, and characterized at appropriate time points which can last few years. Various analytical methods are used to evaluate the integrity of the protein during storage and/or or other relevant stresses. The stabilizers effective under forced degradation studies should be effective in stabilizing the protein under real life handling, storage, and transportation conditions.

Methods herein described can be useful for carrying out any one or all three stages of the development process, but, are particularly useful for systematically screening the combinatorial amino acid space for those amino acid-containing formulations most likely to provide the desired formulation characteristics and long term stability.

An embodiment provides methods for developing protein formulations with desirable properties, such as high protein concentration, stability, enhanced solubility, improved recovery, less aggregate for reduced immunogenicity, minimum proteineous particulates, low viscosity, and high syringeability, etc.

In an embodiment in this regard, test compositions are formulated comprising a protein with individual amino acids and the solubility, stability and/or viscosity of the compositions is determined. One or more compositions with the most desirable properties are selected for further development.

Optionally, pair-wise combinations of the amino acids with the best performance with other amino acids are formulated with the protein and tested for solubility, stability and/or viscosity. One or more of the two-amino acid compositions with the most desirable properties are selected for further development.

Optionally, each of the selected pair wise compositions is formulated with the protein and a third amino acid to form for each pair a set of three amino acid-containing formulations. These formulations are tested solubility, stability and/or viscosity. One or more of the three amino acid-containing compositions with the most desirable properties are selected for further development.

Optionally, each of the selected three amino acid containing compositions is formulated with the protein and one or more fourth amino acids to form for each a set of four amino acid-containing formulations. These formulations are tested solubility, stability and/or viscosity. One or more of the four amino acid-containing compositions with the most desirable properties are selected for further development.

Optionally, each of the selected four amino acid containing compositions is formulated with the protein and one or more fifth amino acids to form for each a set of five amino acid-containing formulations. These formulations are tested solubility, stability and/or viscosity. One or more of the five amino acid-containing compositions with the most desirable properties are selected for further development.

Optionally, each of the selected five amino acid containing compositions is formulated with the protein and one or more sixth amino acids to form for each a set of six amino acid-containing formulations. These formulations are tested solubility, stability and/or viscosity. One or more of the six amino acid-containing compositions with the most desirable properties are selected for further development.

Optionally, each of the selected six amino acid containing compositions is formulated with the protein and one or more seventh amino acids to form for each a set of seven amino acid-containing formulations. These formulations are tested solubility, stability and/or viscosity. One or more of the seven amino acid-containing compositions with the most desirable properties are selected for further development.

Optionally, each of the selected seven amino acid containing compositions is formulated with the protein and one or more eighth amino acids to form for each a set of eight amino acid-containing formulations. These formulations are tested solubility, stability and/or viscosity. One or more of the eight amino acid-containing compositions with the most desirable properties are selected for further development.

Optionally, the procedure can be repeated with additional amino acids, amino acid derivative and other substances.

In an embodiment, viscosity can be measured by methods known to one of skill in the art, including the use of various types of viscometers and rheometers. In a further embodiment the viscometer is a U-tube viscometer, a falling piston viscometer, a rotational viscometer or a bubble viscometer. In an embodiment, the rheometer is a Rheotans, a CaBer, an Acoustic, a Falling Plate, a Capillary/Contraction Flow, a FiSER or a Sentmanat. In a further embodiment, viscosity is measured with a Zahn cup, in which the efflux time is determined or a Ford viscosity cup.

The process is illustrated in the examples below, for up to seven amino acids in Example 1.

Compositions in accordance with embodiments described herein have desirable properties, such as desirable solubility, viscosity, syringeabilty and stability. Lyophilates in accordance with embodiments described herein have desirable properties, as well, such as desirable stability and reconstitution.

Solubility, such as that of proteins, in compositions can be measured using any of a variety of well known methods. For example, a protein solution is concentrated to a desired concentration or above using ultrafiltration. The concentration in the clear supernatant is determined for solubility. Protein beyond solubility will either precipitate or form a gel.

Viscosity of compositions can be measured using any of a variety of well known methods, such as viscometry, Instron, and measurements of injectability and syringeability.

Stability of compositions—and of proteins therein—can be measured using any of a variety of well known methods, such as visual observation, turbidity measurement at 600-700 nm, light scattering, particle counting, electrophoresis, chromatographic methods like size-exclusion, ion-exchange, hydrophobic interaction, and/or reversed phase, structural analyses like CD, FTIR, fluorescence, DSC, and/or UV/VIS, and biological activity assays. Instability can be indicated by any of soluble aggregates, precipitates (insoluble aggregates), gelation, changes in pH, loss of activity. Aggregation can be measured by SEC-HPLC methods, dynamic light scattering, analytical ultracentrifuge, and by electrophoresis. Stresses relevant for the stability studies include storage at elevated temperature, agitation, freeze-thawing, light exposure, etc.

EXPERIMENTAL EXAMPLES

The compositions and methods described herein will be further understood by reference to the following examples, which are intended to be purely exemplary. The compositions and methods described herein are not limited in scope by the exemplified embodiments, which are intended as illustrations of single aspects only. Any methods that are functionally equivalent are within the scope of the invention. Various modifications of the compositions and methods described herein in addition to those expressly described herein will become apparent to those skilled in the art from the foregoing description and accompanying figures. Such modifications fall within the scope of the invention.

Example 1

Formulation of Infliximab

Infliximab is a chimeric monoclonal antibody specific for human tumor necrosis factor-alpha (TNFα). Infliximab includes human constant and murine variable regions.

Infliximab has been formulated in single use vials as a sterile, white, lyophilized powder for intravenous infusion. Each vial contained 100 mg of the protein, 500 mg sucrose, 0.5 mg polysorbate 80, 2.2 mg monobasic sodium phosphate, monohydrate, and 6.1 mg dibasic sodium phosphate dihydrate (no preservatives), to be reconstituted with 10 ml Sterile Water USP before use. The pH of the reconstituted solution is approximately 7.2. The final concentration of the antibody was only 10 mg/ml.

Attempts to constitute the protein at higher concentrations, e.g., 100 mg/ml did not produce satisfactory results. Stability of Infliximab at these higher concentration was poor and viscosity was high making it unsuitable for subcutaneous administration.

Stable, high concentration formulations have been developed that included one or more amino acids. The solubility and the stability of each formulation was determined by incubating the formulation for few days at 50° C. which is below the thermal unfolding temperature of the antibody.

Figure 1:
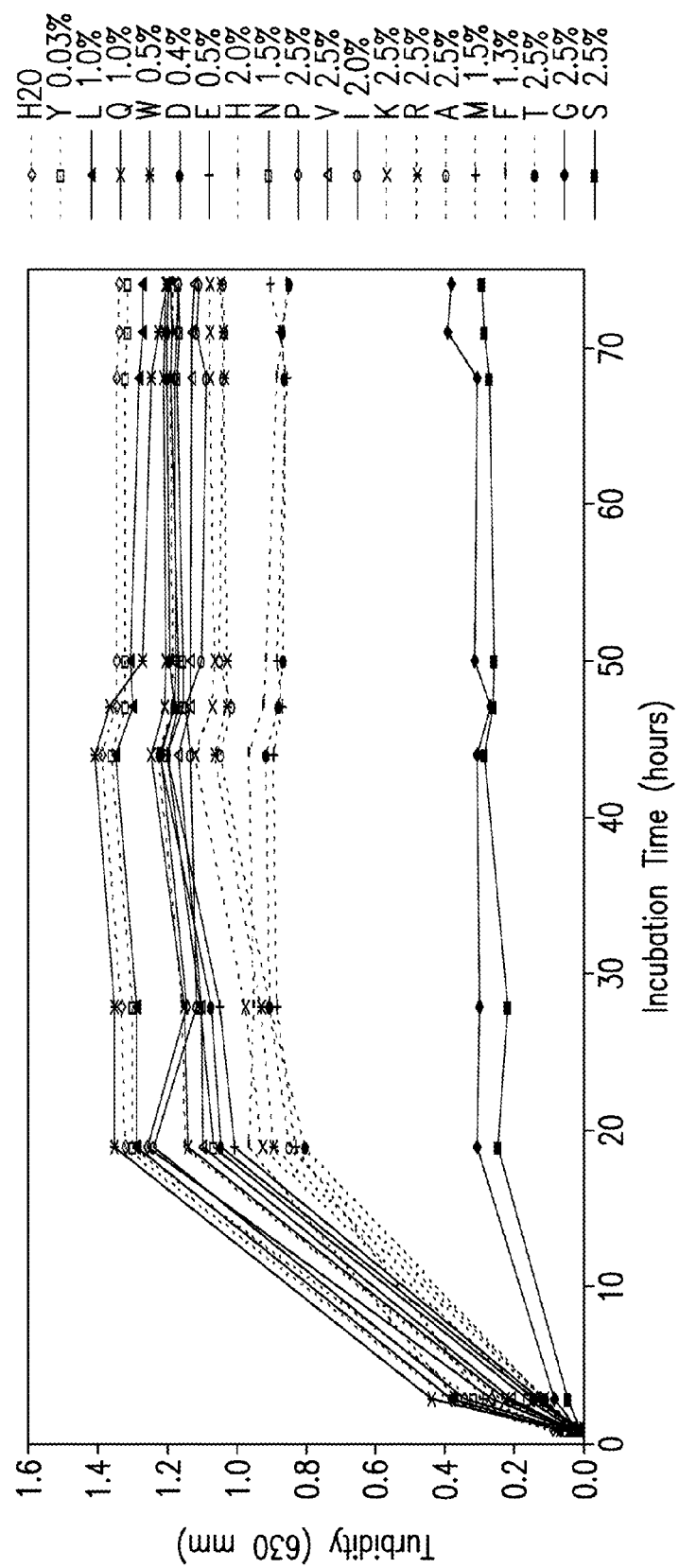
FIG. 1 compares the effects of single amino acids on the precipitation of the antibody Infliximab during incubation at 50° C. All tested samples contained 10 mg/mL of Infliximab, 5% sucrose, 0.005% polysorbate 80, 5 mM sodium phosphate buffer at pH 7.2. Concentration (w/v) of each amino acid is shown in the legend.

It was observed that L-serine and L-glycine, individually, at about 2.5% (w/v), stabilized Infliximab resulting in much less precipitation than the control that did not contain any amino acid and than with other amino acids (FIG. 1).

Formulations with more than one amino acid have also been tested. To this end, the stability of the protein was determined in formulations containing no amino acid, containing S, G or T alone (12.5 mg/mL), or containing S, G or T (12.5 mg/mL) in combination with other amino acids (e.g., A, L, F, M, V, P, I, R, K, Y, Q, E, D, N, H, or W). Each formulation was incubated at 50° C. and stability was measured by turbidity at 630 nm.

Figure 2:
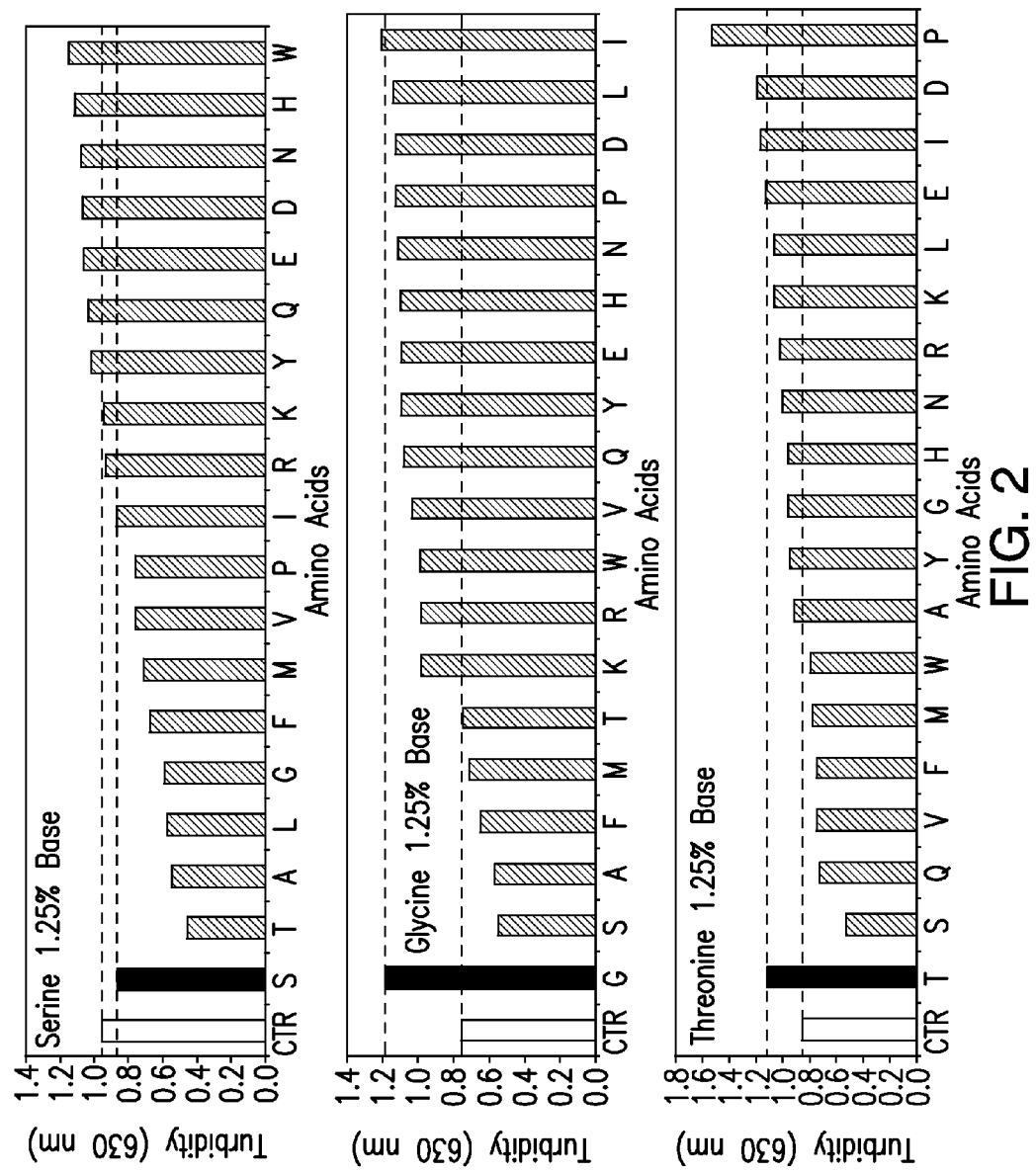
FIG. 2 includes charts showing the effect of amino acids on the precipitation of Infliximab after 33 hours incubation at 50° C. Base amino acids (e.g., serine, glycine or threonine) were included in all samples except the control (CTR) which did not contain an amino acid. All tested samples contained 10 mg/mL of Infliximab, 5% sucrose, 0.005% polysorbate 80, and 5 mM sodium phosphate buffer at pH 7.2. Concentrations of the second amino acids are shown in the table below.

Results from this study following 33 hours at 50° C. are shown in FIG. 2. At the concentrations of 12.5 mg/mL (w/v), little stabilization was observed for the individual amino acids S, G or T, compared to the no amino acid control. At the tested concentration of each amino acid, several combinations, including combinations with R, were destabilizing compared to the control; on the other hand, a variety of combinations stabilized the protein relative to the control.

Results for compositions containing S, T or G alone, S, T and G in all pair wise combinations and all three together (at 12.5 mg/mL in all cases) are shown in FIG. 3. Stability measured after 30 hours at 50° C. by turbidity at 630 nm was improved with all such combinations but not with each individual amino acid alone. The combination of all three amino acids provided the best results shown in the figure.

Results obtained with formulations containing S and A (10.5 mg/mL each) in combination with each of 17 other natural amino acids (all 20 except C) are shown in FIG. 4. Stability was determined by turbidity at 630 nm. The figure shows turbidity after 31 hours at 50° C. Best results in this experiment were obtained using S and A in combination with G, L, M or F. The concentration of infliximab used in the study was 50 mg/mL for screening purpose.

Results obtained with formulations containing S, A and G in different ratios are shown in FIG. 5. Stability over 23 hours incubation at 50° C. were determined by turbidity measured at 630 nm. All combinations were far superior to the control that did not contain any amino acid, or the combination of two amino acids as presented in FIG. 2-3.

The stability of formulations containing S, A and G (35, 12.5 and 30 mg/mL, respectively) in combination with all other natural amino acids were then determined. Stability was measured by turbidity at 630 nm after incubation at 50° C. Partial results obtained after 89 hours are shown in FIG. 6. All except three of the formulations with four amino acids were more stable than the control containing only S, A and G. The formulation containing all of S, A and G along with T was significantly more stable than the combination with S, A, and G only.

The stability of formulations containing S, A and G (35, 12.5 and 30 mg/mL, respectively) in combination with T by itself at 12.5 mg/mL and in combination with each of the other natural amino acids except R and C were then determined. Stability was measured by turbidity at 630 nm during incubation for 75 minutes at 50° C. The results are presented in FIG. 7. Generally the formulations containing four or five amino acids provided better results than the combination of S, A and G. The formulation containing five amino acids, S, A, and G with 12.5 mg/mL V and T, was substantially more stable and provided the best results in this group.

The stability of formulations containing S, A, G, V and T (35, 12.5, 30 mg/mL, 12.5 and 12.5 mg/mL, respectively) in combination with several pairs of other amino acids (7.5 mg/mL N+12.5 mg/mL P, 2 mg/mL D+12.5 mg/mL P, 5 mg/mL Q+12.5 mg/mL P, 10 mg/mL I+12.5 mg/mL P, 7.5 mg/mL N+5 mg/mL Q, 10 mg/mL I+5 mg/mL Q, 2 mg/mL D+5 mg/mL Q, 7.5 mg/mL N+10 mg/mL I, 2 mg/mL D+10 mg/mL I, or 7.5 mg/mL N+2 mg/mL D) were then determined. Stability was measured by turbidity at 630 nm during incubation for 120 minutes at 50° C. Results are shown in FIG. 8. Generally the formulations having seven amino acids provided better results than those having 0, 3 or 5 amino acids.

The stabilization by the combined amino acids was also effective while being concentrated and during subsequent storage (Table 1). The amount of aggregation increased to 1.9% during concentrating and to 3.6% in 3 weeks during storage at 25° C. for the formulations without the amino acids, while the aggregation level did not change significantly in the formulations with the amino acids.

TABLE 1

Stability of Infliximab during concentration (190 mg/mL) and subsequent storage at 25° C.

| Storage at 25° C. | Aggregation by SE-HPLC (%) | | |
|---|---|---|---|
| | No Amino Acid | SAGVT* | Reference** |
| Time 0 | 1.9 | 1.1 | 1.4 |
| 2 weeks | 2.7 | 1.7 | 1.6 |
| 3 weeks | 3.6 | 1.3 | 1.2 |

*3.5% S, 1.25% A, 3% G, 1.25% V, 1.25% T
**Stored at −70° C. at 40 mg/mL

The inclusion of amino acids as well as the proper adjustment of pH improved the injectability of Infliximab at elevated concentrations due to the decreasing viscosity (Tables 2-3). Surprisingly enough, amino acids that were effective for reducing aggregation were different from those required to reduce the viscosity. The addition of arginine to the combination of S, A, G, V and T (35, 12.5, 30 mg/mL, 12.5 and 12.5 mg/mL, respectively) at pH 7.2 reduced the time for injection (Table 2). Arginine increased the injection time at pH 5 while proline and glutamine reduced the injection time at the acidic pH.

TABLE 2

Amino acid effect on completion time of 160 mg/mL injection of Infliximab at pH 7.2

| Sample | Injection Time (sec)** |
|---|---|
| SAGVT* at pH 7.2 | 28.1 |
| SAGVT at pH 7.2 + 1% Arginine | 16.9 |
| SAGVT at pH 7.2 + 3% Arginine | 13.2 |

*Infliximab concentration was 160 mg/mL
**Injection of 1 mL with a 30 gauge needle under 4 lbs force
***3.5% S, 1.25% A, 3% G, 1.25% V, 1.25% T

TABLE 3

Amino acid effect on completion time of 200 mg/mL injection of Infliximab at pH 5.0

| Sample | Injection Time (sec)** |
|---|---|
| SAGVT*** at pH 7.2 | 29.9 |
| SAGVT at pH 5.0 | 11.7 |
| SAGVT + 1% Arginine at pH 5.0 | 17.1 |
| SAGVT + 0.4% Glutamine at pH 5.0 | 10.9 |
| SAGVT + 1% Proline at pH 5.0 | 9.4 |

*Infliximab concentration was 200 mg/mL
**Injection of 1 mL with a 27 gauge needle under 4 lbs force
***3.5% S, 1.25% A, 3% G, 1.25% V, 1.25% T These results demonstrate that combination of amino acids is suitable for improving the commercial feasibility of protein formulations with respect to both stability as well as injectability.

Example 2

Formulation of Trastuzumab

Trastuzumab is a monoclonal antibody that interferes with the HER2/neu receptor and is currently used for the treatment of metastatic breast cancer. It is currently introduced as a lyophilized formulation containing trehalose, L-histidine, and polysorbate 20 at pH 6 at the antibody concentration around 21 mg/mL.

When concentrated, the antibody exhibits poor stability due to faster aggregation as well as being difficulty to inject due to increased viscosity.

Amino acids, especially Arginine, Asparagine, Lysine, Valine, Threonine, Proline, Isoleucine, Glutamic acid, and Serine, were effective in enhancing the stability of Trastuzumab by reducing the tendency to aggregate (see Table 4). At higher concentration, L-glycine also showed good stabilization (FIG. 29).

TABLE 4

Stabilization of Concentrated Trastuzumab by amino acids

| | | Purity by SE-HPLC after 4 days at 60° C. | |
|---|---|---|---|
| Amino Acid | Concentration (%)** | % Main-Peak | Stabilization (%) |
| No* (4° C.) | 0 | 99.60 | — |
| No (60° C.) | 0 | 98.98 | 0.0 |
| Arginine | 2.5 | 99.59 | 98.6 |
| Asparagine | 1.5 | 99.29 | 50.4 |
| Lysine | 2.5 | 99.26 | 45.7 |
| Valine | 2.5 | 99.23 | 40.5 |
| Threonine | 2.5 | 99.20 | 35.1 |
| Proline | 2.5 | 99.19 | 33.5 |
| Isoleucine | 2 | 99.17 | 30.3 |
| Glutamic acid | 0.5 | 99.14 | 26.4 |
| Serine | 2.5 | 99.11 | 20.1 |

*Base formulation contains 5 mM Histidine (pH 6.0), 0.01% Polysorbate 20 and 5% Trehalose
**Trastuzumab concentration of 100 mg/mL A number of amino acids, including Histidine, Lysine, Methionine, Glycine, Phenylalanine, Glutamic acid, Threonine, Serine, Asparagine, or Isoleucine, were effective in reducing the viscosity of Trastuzumab for easier injection (Table 5).

TABLE 5

Improvement of injection for concentrated Trastuzumab by amino acids

| Amino acid | Concentration (%)* | Injection Time (sec)** |
|---|---|---|
| Control | 0.0 | 11.2 |
| Histidine | 0.8 | 5.0 |
| Lysine | 1.0 | 5.1 |
| Methionine | 0.6 | 5.7 |
| Glycine | 1.0 | 6.1 |
| Phenylalanine | 0.5 | 6.3 |
| Glutamic acid | 0.2 | 6.4 |
| Threonine | 1.0 | 6.5 |
| Serine | 1.0 | 6.8 |
| Asparagine | 0.6 | 7.1 |
| Isoleucine | 0.6 | 7.1 |

*Trastuzumab concentration of 240 mg/mL
**Injection volume of 0.4 mL with 27 gauge needle under 4 lbs Therefore, these amino acids are useful in overcoming both stability and viscosity issues at higher concentrations for Trastuzumab.

Example 3

Formulation of Rituximab

Rrituximab is a genetically engineered chimeric murine/human monoclonal IgG1 kappa antibody used for the treatment of multiple indications including Non-Hodgkin's Lymphoma, Chronic Lymphocytic Leukemia, and Rheumatoid Arthritis. The product is commercially presented as a liquid formulation containing polysorbate 80, sodium citrate dihydrate, sodium chloride in pH 6.5 with the antibody concentration of 10 mg/mL for intravenous delivery.

Several amino acids turned out to stabilize the antibody against precipitation during storage for 4 days at 55° C. (Table 6). Such amino acids included arginine, histidine, methionine, lysine, and phenylalanine (Table 6).

TABLE 6

Amino acids effect on stabilization of Rituximab after 4 day incubation at 55° C.

| Sample | Concentration | Optical Density at 630 nm |
|---|---|---|
| Ala | 1.0% | 0.81 |
| Asp | 0.16% | 0.85 |
| Asn | 0.6% | 0.83 |
| Gln | 0.4% | 0.78 |
| Glu | 0.18% | 0.73 |
| Thr | 1.0% | 0.66 |
| Gly | 1.0% | 0.65 |
| Ile | 0.6% | 0.59 |
| Trp | 0.2% | 0.56 |
| Tyr | 0.01% | 0.56 |
| Leu | 0.4% | 0.51 |
| Val | 1.0% | 0.50 |
| Pro | 1.0% | 0.49 |
| Ser | 1.0% | 0.43 |
| Phe | 0.5% | 0.32 |
| Lys | 1.0% | 0.23 |
| Met | 0.6% | 0.15 |
| Arg | 1.0% | 0.04 |
| His | 0.8% | 0.02 |
| Control | 0.0% | 0.43 |

All formulations contain 20 mg/mL Rituximab, 0.07% polysorbate 80, 0.9% sodium chloride in 25 mM sodium citrate buffer at pH 6.5.

Example 4

Formulation of Cetuximab

Cetuximab is a chimeric monoclonal antibody specific for the epidermal growth factor receptor (EGFR) inhibitor, administered by intravenous infusion for the treatment of metastatic colorectal cancer and head and neck cancer.

Cetuximab is formulated in single use vials as a sterile liquid formulation containing 2 mg of the antibody, 8.48 mg sodium chloride, 1.88 mg sodium phosphate dibasic heptahydrate, 0.41 mg sodium phosphate monobasic monohydrate, and water for Injection, USP in each mL of the formulation. The pH of the reconstituted solution was approximately 7.0-7.4. The product is unstable at higher concentration, such as the formation of visible, white, amorphous cetuximab particulates, so unsuitable for subcutaneous administration in the current formulation.

Formulations that do not produce insoluble particulates at higher concentration have been developed containing amino acids. Formulations were prepared with one or two amino acids. The solubility and the stability of each formulation was rapidly determined by exposing the formulation for few days at 58° C. which is below the thermal unfolding temperature of the antibody. The stability of the protein was determined in formulations containing no amino acid, containing I, K, M, P, S, or R alone (2.5% w/v) or in combination another within the list. Each formulation was incubated at 58° C. and stability was measured by turbidity at 655 nm.

Results following 48 hours at 58° C. are shown in FIG. 9. Little stabilization was observed for the formulations containing each of amino acids I, M, P or S, while K and R showed good stabilization compared to the control. At the tested concentration of each amino acid, all combinations containing R or K were stabilizing compared to individual amino acids or to the control.

Example 5

Formulation of Bevacizumab

Bevacizumab is a recombinant humanized monoclonal IgG1 antibody that binds to and inhibits the biologic activity of human vascular endothelial growth factor (VEGF). Bevacizumab is administered by intravenous infusion for the treatment of metastatic colorectal cancer and lung and breast cancer.

Bevacizumab is formulated in single use vials as a sterile liquid formulation containing 25 mg of the antibody, 60 mg α,α-trehalose dihydrate, 5.8 mg sodium phosphate (monobasic, monohydrate), 1.2 mg sodium phosphate (dibasic, anhydrous), 0.4 mg polysorbate 20, and water for Injection, USP in each mL of the formulation. The pH of the reconstituted solution is approximately 6.2. The product is unstable at higher concentration, so unsuitable for subcutaneous administration in the current formulation.

Formulations that do not produce insoluble particulates at higher concentration have been developed containing one or more amino acids. The solubility and the stability of each formulation was rapidly determined by exposing the formulation for a few hours at 60° C. which is below the thermal unfolding temperature of the antibody. The stability of the protein was determined in formulations containing no amino acid, each of A, G, M, N, S, or T alone (25 mg/mL, 25 mg/mL, 15 mg/mL, 15 mg/mL, 25 mg/mL, or 25 mg/mL, respectively), or each in combination with one or more amino acids in the list. Each formulation was incubated at 60° C. and stability was measured by turbidity at 630 nm.

Results following 6 hours at 60° C. are shown in FIG. 10-15. All individual amino acids A, N, G, M, S and T (25 mg/mL, 15 mg/mL, 25 mg/mL, 15 mg/mL, 25 mg/mL, or 25 mg/mL, respectively) led to good stabilization compared to the no amino acid control. At further reduced concentration of each amino acid, i.e., 12.5 mg/mL, 7.5 mg/mL, 12.5 mg/mL, 7.5 mg/mL, 12.5 mg/mL, or 12.5 mg/mL, respectively, only N, S, or T, achieved stabilization and A, G, or M failed to stabilize the antibody (FIG. 11). However, all formulations containing combinations of two amino acids provided better stabilization compared to those with one amino acid or to the control (FIG. 11). The comparison of two and three amino acid combinations are shown in FIG. 12-15. At the concentrations of 8.3 mg/mL, 5 mg/mL, 8.3 mg/mL, 5 mg/mL, 8.3 mg/mL, or 8.3 mg/mL, respectively for A, N, G, M, S, or T, any combinations of three amino acids provided better stabilization than the corresponding two amino acid combinations. For instance, AGM better than AG, GM, or AM (FIG. 12, 14); GMT better than GM, GT, or MT; (FIG. 14,15) or MST better than MS, MT, or ST, etc. (FIG. 15).

Example 6

Formulation of Ranibizumab

Ranibizumab binds to and inhibits the biological activity of human vascular endothelial growth factor A (VEGF-A) and is designed for intraocular use. Its current formulation contains 10 mg Ranibizumab, 10 mM histidine HCl, 100 mg α,α-trehalose dihydrate, and 0.1 mg of polysorbate 20, at pH 5.5 in each mL. The protein generates insoluble particulates during storage at elevated temperatures.

Formulations that do not produce insoluble particulates at higher concentration have been developed containing one or more amino acids. The solubility and the stability of each formulation was rapidly determined by exposing the formulation for hours at 60° C. which is below the thermal unfolding temperature of the protein.

The stability of the protein was determined in formulations containing no amino acid, A, G, N, Q, S, or T alone (12.5 mg/mL, 12.5 mg/mL, 7.5 mg/mL, 5 mg/mL, 12.5 mg/mL, or 12.5 mg/mL, respectively), or each of the amino acids in combination with one or more other amino acids from the list. Each formulation was incubated at 60° C. and stability was measured by turbidity at 630 nm.

Results for such a study following 6 hours at 60° C. are shown in FIG. 16-18. All individual amino acids A, G, N, Q, S or T at the tested concentrations provided good stabilization compared to the no amino acid control (FIG. 16). Moreover, all formulations containing combinations of two amino acids provided even better stabilization compared to individual amino acids or to the control (FIG. 17). The comparison of two and three amino acids combinations are shown in FIG. 18. At the concentrations of 8.3 mg/mL, 8.3 mg/mL, 5 mg/mL, 3.3 mg/mL, 8.3 mg/mL, or 8.3 mg/mL, respectively, any combinations of three amino acids provided better stabilization than the corresponding two amino acid combinations. For instance, ANQ better than AN, AQ, or NQ; or ANS better than AN, AS, or NS; or QST better than QS, QT, or ST, etc. (FIG. 18).

Some of the results above are summarized in Tables 7 and 8, which also include additional data not explicitly described above. The compositions and methods described herein will be understood to include formulations with any one or more of the "single effective" amino acids with any protein, and with any one of the listed proteins (antibodies) in particular. Additionally, the compositions and methods described herein will be understood to include formulations with any one or more of the "single effective" amino acids and any one or more of the "secondary" amino acids with any protein, and with any one of the listed proteins (antibodies) in particular. The name of a commercial antibody product comprising the listed antibody is given, but it must be understood that the commercial antibody product does not include the amino acids as described herein.

TABLE 7

Single amino acid or amino acid combinations that stabilize antibodies

| Antibody | Single Effective | Secondary | Commercial product |
|---|---|---|---|
| Infliximab | S, G, T, F, R, N, P | A, L, V | Remicade REMICADE ® |
| Bevacizumab | S, T, N | A, G, M | Avastin AVASTIN ® |

TABLE 7-continued

Single amino acid or amino acid combinations that stabilize antibodies

| Antibody | Single Effective | Secondary | Commercial product |
|---|---|---|---|
| Ranibizumab | S, T, N, A | G, Q | Lucentis LUCENTIS ® |
| Cetuximab | R, K | I, M, P, S | Erbitux ERBITUX ® |
| alpha-galactosidase A | S, T, G | V, P, A | Fabrazyme FABRAZYME ® |
| IgG4 | A, N, G, K, S, T | R, Q | |
| Rituximab | H, R, M, K, F | | Rituxan RITUXAN ® |
| Trastuzumab | H, K, M, G, F, E, T, S, A, I | R, N, K, V, T, P, I, E, S | Herceptin HERCEPTIN ® |

TABLE 8

Single amino acid or amino acid combinations that stabilize antibodies

| Amino acid | Formulations | | Examples |
|---|---|---|---|
| A | Use of L-A or D-A in combination with other amino acids | Infliximab | AS, AG, ASG, ASL, ASM, ASF, ASV, ASG + 4th(TVMPLIERKQDHorN) |
| | | Bevacizumab | AN, AG, AM, AS, AT, ANG, ANM, ANS, AST, AGM, AGS, AGT, AMS, AMT, AST (Any combinations with one, two or three of AGNMST) |
| | | Ranibizumab | A, AN, AG, AS, AT, ANQ, ANG, ANS, ANT, AQG, AQS, AQT, AGS, AGT, AST (Any combinations with one, two or three of ANGSQT) |
| N | Use of L-N or D-N along, or in combination with other amino acids | Infliximab | NSGA |
| | | Bevacizumab | N, NG, NM, NS, NT, NA, NMA, NMS, NMT, NAT (Any combinations with one, two or three of NAMGST) |
| | | Ranibizumab | N, NA, NG, NQ, NS, NT, NAQ, NAG, NAS, NAT, NQG, NQS, NQT, NGS, NGT (Any combinations with one, two or three of NAGQST) |
| | | Trastuzumab | NR, NH, NK, NM, NG |
| D | Use of L-D or D-D in combination with other amino acids | Infliximab | DSAG, DSAGVTP, DSAGVTN, DSAGVTI |
| Q | Use of L-Q or D-Q along, or in combination with other amino acids | Infliximab | QT, QSAG, QSAGT, QSAGVTP, QSAGVTN, QSAGVTD, QSAGVTI |
| | | IgG4 | Q, QW |
| | | Ranibizumab | QA, QN, QG, QS, QT, QAN, QAG, QAS, QAT, QNG, QNS, QNT, QGS, QGT, QST |
| E | Use of L-E or D-E in combination with other amino acids | Infliximab | ESAG |
| I | Use of L-I or D-I along, or in combination with other amino acids | Infliximab | ISAG, ISAGT, ISAGVTP, ISAGVTN, ISAGVTD, ISAGVTQ |
| | | Cetuximab | IR, IK |
| L | Use of L-L or D-L in combination with other amino acids | Infliximab | LS, LAS, LASG, LASGT |
| K | Use of L-K or D-K in combination with other amino acids | Infliximab | KSAG |
| | | Cetuximab | K, KR, KI, KM, KP |
| | | Rituximab | KR, KH, KM |
| | | Trastuzumab | KR, KH, KM, KG |
| F | Use of L-F or D-F along, or in combination with other amino acids | Infliximab | FS, FG, FT, FGSA, |
| | | Rituximab | FR, FK, FH, FM |
| | | Trastuzumab | FR, FK |
| S | Use of L-S or D-S along, or in combination with other amino acids | Infliximab | S, ST, SA, SL, SG, SF, SM, SV, SP, STG, SAG, SAL, SAM, SAF, SAV, SAG + 4th(TVMPLIERKQDHorN) |
| | | Cetuximab | SR |
| | | Bevacizumab | S, ST, SA, SN, SG, SM, SAN, SAG, SAM, SAT, SNM, SGM, SGT, SMT (Any combinations with one, two or three of STANGM) |
| | | Ranibizumab | S, SA, SN, SQ, SG, ST, SAN, SAQ, SAG, SAT, SNQ, SNG, SNT, SQG, SQT, SGT (Any combinations with one, two or three of STANGQ) |

TABLE 8-continued

Single amino acid or amino acid combinations that stabilize antibodies

| Amino acid | Formulations | | Examples |
|---|---|---|---|
| T | Use of L-T or D-T along, or in combination with other amino acids | Infliximab | TS, TQ, TV, TF, TM, TW, TG, TSG, TSAG, TSAGN, TSAGD, TSAGQ, TSAGL, TSAGE, TSAGI, TSAGK, TSAGH, TSAGM, TSAGF, TSAGP, TSAGW, TSAGY, TSAGV, TSAGV with other amino acids |
| | | Bevacizumab | T, TA, TN, TG, TM, TS, TAN, TAM, TAG, TAS, TNM, TGA, TGM, TGS, TMS (Any combinations with one, two or three of TANGMS) |
| | | Ranibizumab | T, TA, TN, TG, TQ, TS, TAN, TAQ, TAG, TAS, TNQ, TGA, TGN, TGS, TNS, TQS (Any combinations with one, two or three of TANGQS) |
| W | Use of L-W or D-W along, or in combination with other amino acids | IgG4 | TR, TH, TQ |
| Y | Use of L-Y or D-Y along, or in combination with other amino acids | | No data available |
| V | Use of L-V or D-V along, or in combination with other amino acids | Infliximab | VS, VT, VAS, VASG, VASGT, VASGT+ other amino acids |
| R | Use of L-R or D-R in combination with two or more other amino acids | IgG4 | RW |
| | | Cetuximab | R, RI, RK, RM, RP, RS |
| | | Rituximab | RH, RM, RK |
| | | Trastuzumab | RK, RH, RM, RG |
| P | Use of L-P or D-P in combination with other amino acids | Infliximab | PSAG, PSAGT, PSAGVTN, PSAGVTQ, PSAGVTD |
| | | Cetuximab | PR, PK |
| M | Use of L-M or D-M in combination with other amino acids | Infliximab | MS, MSA, MSAG, MSAGT |
| | | Cetuximab | MR, MK |
| | | Bevacizumab | MS, MA, MT, MN, MG, MAN, MAG, MAS, MAT, MNS, MNT, MGS, MGT, MST (Any combinations with two or three of MASTNG) |
| | | Rituximab | MH, MR, MK |
| | | Trastuzumab | MR, MK, MH, MG |
| G | Use of L-G or D-G in combination with two or more other amino acids | Infliximab | GS, GA, GF, GT, GST, GSA, GSA + 4th(TVMPLIERKQDHorN) |
| | | Bevacizumab | GM, GS, GT, GA, GN, GAM, GAN, GAS, GAT, GMS, GMT, GST, GAM, GAT (Any combinations with two or three of GMASTN) |
| | | Ranibizumab | G, GQ, GS, GT, GA, GN, GAQ, GAN, GAS, GAT, GQS, GQT, GST, GAQ, GAT (Any combinations with one, two or three of GQASTN) |
| H | Use of L-H or D-H in combination with two or more other amino acids | Infliximab | HSAG, HSAGT |
| | | IgG4 | HW |
| | | Rituximab | HR, HM, HK |
| | | Trastuzumab | HR, HM, HK, HG |

Example 7

Formulation of Coagulation Factor IX

Factor IX, also known as the Christmas factor, is one of the serine proteases of the coagulation system. A mutation in the Factor IX gene is commonly associated with Haemophilia B, a blood clotting disorder. Factor IX was formulated in single use vials as a sterile liquid formulation containing 0.234% sodium chloride, 8 mM L-histidine, 0.8% sucrose, 208 mM glycine, 0.004% polysorbate 80 at a concentration of 7.5 mg./ml in 5 ml of solution.

For analysis, an additional amino acid was added to the Factor IX formulation at a concentration of 3% w/v and a final Factor IX concentration of 7.5 mg/ml. The solubility and the stability of each unique amino acid Factor IX formulation was evaluated following incubation of the formulation for 24 hours at 50° C. The stability of the Factor IX protein was determined for each formulation by measuring the percent of soluble aggregates in solution by SE-HPLC. The results of the analysis are shown in FIG. 19. Based on the testing conducted, it was determined that the following amino acids provided the greatest degree of stability to the Factor IX protein following high temperature incubation, G, P, A, S and T, though both V and N improved stability when compared to the Factor IX formulation without any additional amino acid.

Example 8

Formulation of C1 Esterase Inhibitor

C1 Esterase Inhibitor is a protease inhibitor belonging to the serpin superfamily. Its main function is the inhibition of the complement system to prevent spontaneous activation. C1 Esterase Inhibitor is isolated from blood plasma. 100 mg C1 Esterase Inhibitor was formulated in single use vials as a sterile liquid formulation containing 85-115 mg L-glycine, 70-100 mg sodium chloride, 25-35 mg sodium acetate in 10 ml solution with a C1 esterase concentration of 10 mg/ml.

For analysis, an additional amino acid was added to the C1 Esterase Inhibitor formulation with the tested formulation having a final C1 Esterase Inhibitor concentration of 10 mg/ml. The following amino acids were added at a concentration of 3% (w/v), K, R, G, A, T, S and V. The following amino acids were added at a concentration of 0.5% (w/v), E and D. The following amino acid was added at a concentration of 2% (w/v), N. Each formulation was evaluated for 48 hours at 45° C. and evaluated for the percent of soluble aggregates in solution by SE-HPLC at A650. Results are shown in FIG. 20. Based on the testing conducted, it was determined that the following amino acids provided the greatest degree of stability to the C1 Esterase Inhibitor protein following high temperature incubation, K, R, G, A, E, S and T, though D, V and N improved stability when compared to the C1 Esterase Inhibitor formulation without any additional amino acid.

Example 9

Formulation of Basiliximab

Basiliximab is a chimeric mouse-human monoclonal antibody to the α chain (CD25) of the IL-2 receptor of T cells. It is used to prevent rejection in organ transplantation, especially in kidney transplants. Basiliximab was formulated in single use vials as a sterile liquid formulation containing 0.99 mg disodium hydrogen phosphate, 1.61 mg NaCl, 7.21 mg potassium phosphate, 20 mg sucrose, 40 mg glycine and 80 mg mannitol in 5 ml solution with a Basiliximab concentration of 2 mg/ml.

For analysis, an additional amino acid was added to the Basiliximab formulation with the tested formulation having a final Basiliximab concentration of 2 mg/ml. The following amino acids were added at a concentration of 3% (w/v), G, V, S, A, K and P. The following amino acids were added at a concentration of 0.5% (w/v), D and E. The following amino acid was added at a concentration of 2% (w/v), N, M and I. The following amino acid was added at a concentration of 1% (w/v), Q. Each formulation was evaluated for 48 hours at 55° C. and evaluated for the percent of soluble aggregates in solution by SE-HPLC. Results are shown in FIG. 21. Based on the testing conducted, it was determined that the following amino acids provided the greatest degree of stability to the Basiliximab protein following high temperature incubation, N, M, G, I, D, E, V, S and K, though P and Q improved stability when compared to the Basiliximab formulation without any additional amino acid.

Example 10

Formulation of Panitumumab

Panitumumab is a fully human monoclonal antibody specific to the epidermal growth factor receptor. The protein generates insoluble particulates during storage at elevated temperatures. Panitumumab was formulated in single use vials as a sterile liquid formulation containing 117 mg NaCl, 136 mg. sodium acetate, pH 5.8 in 20 ml solution with a Panitumumab concentration of 10 mg/ml.

For analysis, an additional amino acid was added to the Panitumumab formulation with the tested formulation having a final Panitumumab concentration of 10 mg/ml. The following amino acids were added at a concentration of 3% (w/v), S, G, A, V and P. The following amino acid was added at a concentration of 0.1% (w/v), Y. The following amino acid was added at a concentration of 2% (w/v), N and M. Each formulation was evaluated for 48 hours at 55° C. and evaluated for the percent of soluble aggregates by SE-HPLC. Results are shown in FIG. 22. Based on the testing conducted, it was determined that the following amino acids provided the greatest degree of stability to the Panitumumab protein following high temperature incubation, S, G, A, Y, V and P, though D and M improved stability when compared to the Panitumumab formulation without any additional amino acid.

Example 11

Formulation of α-Galactosidease A

α-galactosidase A is a glycoside hydrolase enzyme that hydrolyses the terminal alpha-galactosyl moieties from glycolipids and glycoproteins. It is used in the treatment for Fabry's disease. The protein generates insoluble particulates during storage at elevated temperatures. α-galactosidase A was formulated in single use vials as a sterile liquid formulation containing 5.5 mg of agalsidase beta, as well as 33.0 mg mannitol, 3.0 mg sodium phosphate monobasic monohydrate, and 8.8 mg sodium phosphate dibasic heptahydrate in 1 ml solution with a α-galactosidase A concentration of 5 mg/ml.

For analysis, an additional amino acid was added to the α-galactosidase A formulation with the tested formulation having a final α-galactosidase A concentration of 2.5 mg/ml. The following amino acids were added at a concentration of 1% (w/v), A, G, P, S, T and V. Each formulation was evaluated for 16 hours at 45° C. and evaluated for the percent of soluble aggregates in solution by SE-HPLC. Results are shown in FIG. 23. Based on the testing conducted, it was determined that that all of the amino acids analyzed (A, G, P, S, T and V) provided a high degree of stability to the α-galactosidase A protein following high temperature incubation than the control where no amino acid was added.

Example 12

Formulation of β-Glucocerebrosidase

β-glucocerebrosidase is an enzyme with glucosylceramidase activity that is needed to cleave by hydrolysis, the beta-glucosidic linkage of the chemical glucocerebroside, an intermediate glycolipid metabolism. β-glucocerebrosidase was formulated in single use vials as a sterile liquid formulation containing 170 mg mannitol, 70 mg sodium citrates, 0.53 mg polysorbate 80 in 5 ml solution with a β-glucocerebrosidase of 20 U/ml.

For analysis, an additional amino acid was added to the a β-glucocerebrosidase A formulation with the tested formulation having a final a β-glucocerebrosidase A concentration of 20 U/ml. The following amino acids were added at a concentration of 2.5% (w/v), A, R, G, K, P, S, T and V. The following amino acid were added at a concentration of 0.5% (w/v), W. The following amino acid was added at a concentration of 1.5% (w/v), N, Q, I and M. The following amino acid was added at a concentration of 0.4% (w/v), D. The following amino acid was added at a concentration of 0.45% (w/v), E. The following amino acid was added at a concentration of 1% (w/v), L. The following amino acid was added at a concentration of 1.25% (w/v), F. Each formulation was evaluated for 48 hours at 55° C. and evaluated for turbidity at A650. Results are shown in FIG. 24. Based on the testing conducted, it was determined that the following amino acids provided the greatest degree of stability to the β-glucocerebrosidase protein following high temperature incubation, G, A, P, S, T and V, though W, R, N, D, Q, E, I, L, K, M and F improved stability when compared to the β-glucocerebrosidase formulation without any additional amino acid.

Example 13

Viscosity of Tratsuzumab

The ability of high concentrations of amino acids in a formulation with a high concentration of protein was tested by determining the estimated viscosity of the protein solution as it was pushed through a 30 gauge needle. Viscosity was measured in cP and viscosity for each solution was calculated based on a standard curve based on the viscosity of a glycerol solution pushed through the same 30 gauge needle with the same applied pressure. Tratsuzumab was formulated in single use vials as a sterile liquid formulation containing 400 mg trehalose dehydrate, 9.9 mg L-histidine HCl, 6.4 mg L-histidine, and 1.8 mg polysorbate 20 at pH 6.0 in 20 ml of solution with a Tratsuzumab concentration of 300 mg/ml. Prior to testing, the Tratsuzumab formulation was concentrated and the tested solution had a final Tratsuzumab concentration of 300 mg/ml. Five amino acids were tested, five of which were tested at high concentrations: G at 10% final concentration, F at 0.2% final concentration, V at 5% final concentration, P at both 10% and separately at 20% final concentration and A at 10% final concentration. As seen in Table 9, P showed the greatest reduction in viscosity, with the viscosity decreasing as the P concentration in the final formulation was increased.

TABLE 9

| Amino Acids | Estimated Viscosity (cP)* |
| --- | --- |
| None | 120 |
| 10% G | 187 |
| 0.2% F | 220 |
| 5% V | 220 |
| 10% P | 70 |
| 20% P | 45 |
| 10% A | 168 |

*Viscosity estimated based on a standard curve with aqueous glycerol solution.

Example 14

Viscosity of Rituximab

The ability of high concentrations of amino acids in a formulation with a high concentration of protein was tested by determining the estimated viscosity of the protein solution as it was pushed through a 30 gauge needle. Viscosity was measured in cP and viscosity for each solution was calculated based on a standard curve based on the viscosity of a glycerol solution pushed through the same 30 gauge needle with the same applied pressure. Rituximab was formulated in 0.7 mg/ml polysorbate 80, 7.35 mg/ml sodium citrate dehydrate, 9 mg/ml sodium chloride and water with a pH of 6.5 and a Rituximab concentration of 200 mg/ml. Prior to testing, the Rituximab formulation was concentrated and the tested solution had a final Rituximab concentration of 200 mg/ml. Ten amino acids were tested, five of which were tested at high concentrations: G, S, V, P and A at 10% final concentration, H and M at 2% final concentration, I at 0.1% final concentration, F at 0.2% final concentration and T at 5% final concentration. As seen in Table 10, Pro showed the greatest reduction in viscosity, with H, M, T, and V also reducing the viscosity of the Rituximab solution as compared to a Rituximab solution with no additional amino acids added.

TABLE 10

| Amino Acids | Estimated Viscosity (cP)* |
| --- | --- |
| None | 25 |
| 10% G | 62 |
| 2% H | 19 |
| 0.1% I | 34 |
| 2% M | 19 |
| 0.2% F | 21 |
| 10% S | 21 |
| 5% T | 19 |
| 10% V | 17 |
| 10% P | 12 |
| 10% A | 45 |

Example 15

Formulation with Infliximab

Proline and glycine were evaluated for their ability to provide stability to Infliximab at increasing concentrations of each amino acid. The concentration of proline and glycine ranged from 2.5% (w/v) to 20% (w/v). Infliximab was formulated in single use vials as a sterile liquid formulation containing 50 mg sucrose, 0.05 mg polysorbate 80, 0.22 mg monobasic sodium phosphate monohydrate and 0.61 mg dibasic sodium phosphate dehydrate at a pH of 7.2 and an Infliximab concentration of 150-200 mg/ml to a tested final concentration of 150 mg/ml-200 mg/ml. Each formulation was evaluated for 3 days at 45° C. Samples after incubation were diluted ten times in PBS before measuring turbidity at A650. As seen in FIG. 25, as the concentration of glycine increases in the formulation, the stability of the Infliximab in solution increased. A similar result was not seen with P, which did not stabilize the protein any better than the control that did not add an amino acid to the Infliximab formulation, even at high concentrations.

The ability of high concentrations of G and P in a formulation with a high concentration of Infliximab was tested to determine the effect of each on the viscosity of the protein solution. Viscosity was measured by injection of 50 µl sample with a plunger speed set at 50 mm/min. Injection was made by the compression of air from an empty 1 ml syringe through a 30 gauge needle and measured in cP. The control was calculated based on a standard curve based on the viscosity of a glycerol solution through the same gauge needle under the same pressure. Infliximab was formulated at a final tested concentration of 150 mg/ml. As seen in FIG. 26, as the concentration of P increased from 2.5% (w/v) to 20% (w/v), the viscosity of the protein solution decreased. The benefit of Proline was also demonstrated at pH 5 as shown in Table 11, where it is shown that the viscosity of the Infliximab solution decreases from 106 cP for the control to 40 cP for the P 10% (w/v) final formulation containing 200 mg/ml Infliximab. A similar result was not seen with G.

TABLE 11

| L-proline Concentration (w/v %) | Estimated Viscosity (cP) |
| --- | --- |
| None | 106 |
| 10% | 40 |

Further evaluations were conducted to evaluate the ability of a formulation comprising a combination of G and P to stabilize the protein and lower viscosity. The Infliximab concentration for this evaluation was 150 mg/ml. As seen in FIG. 27, the combination of P and G at a concentration of 10%

(w/v) evaluated after incubating the Infliximab solution at 45° C. for 3 days was better at stabilizing Infliximab as compared to Infliximab formulated with either P or G alone or with no amino acid. As seen in FIG. 28, the addition of G to a formulation containing P did not affect the ability of P to lower the viscosity of the Infliximab formulation and the combination lowered the viscosity to a greater degree than either the G alone or no amino acid control.

Example 16

Formulation with Tratsuzumab

[P and G were evaluated independently and then in combination for their ability to provide stability to Tratsuzumab at increasing concentrations of each amino acid. The concentration of P and G ranged from 2.5% (w/v) to 20% (w/v). Tratsuzumab was formulated in 20 mg/ml trehalose, 0.5 mg L-histidine HCl, 0.32 mg/ml L-histidine and 0.09 mg/ml polysorbate 20 at a pH of 6.0 and a Tratsuzumab concentration of 200 mg/ml. Each formulation was evaluated for 20 hours at 55° C. Stability was measured by evaluating the percent of aggregates by SEC-HPLC. As seen in FIG. 29, as the concentration of glycine increases from 2.5% (w/v) to 20% (w/v) in the formulation, the stability of the Tratsuzumab in solution increased. The combination of glycine and proline at increasing concentrations were generally better at stabilizing Tratsuzumab as compared to Tratsuzumab formulated with either P or G alone or with no amino acid. At lower concentrations, P alone did not stabilize Tratsuzumab any better than the control, though at higher concentrations P did stabilize Tratsuzumab better than the no amino acid control, but not as well as G alone or the combination of P and G.

As seen in FIG. 30, the addition of G to a formulation containing P did not affect the ability of proline to lower the viscosity of the Tratsuzmab formulation and the combination lowered the viscosity to a greater degree than either the glycine alone or no amino acid control, though both G and P alone lowered the viscosity of the Tratsuzumab formulation to a greater extent than the no amino acid control.

Example 17

Formulation with Rituximab

The ability of S and P to stabilize a Rituximab formulation was evaluated. Turbidity was measured after 20 hours at 55° C. Rituximab was formulated in 10 mM sodium citrate buffer, 0.153 M sodium chloride and 0.07% polysorbate 80 at a pH of 6.5. The final Rituximab concentration as tested was 200 mg/ml. Prior to turbidity measurement at 650 nm, the incubated samples were diluted one hundred fold. As seen in FIG. 31, as the concentration of S increases from 2.5% (w/v) to 20% (w/v) in the formulation, the stability of the Rituximab increased. The combination of S and P at increasing concentrations also stabilized Rituximab. P alone did not stabilize Rituximab any better than the control where no amino acids were added to the Rituximab formulation, even at higher amino acid concentrations.

As seen in FIG. 32, the addition of S to a formulation containing P did not affect the ability of P to lower the viscosity of the Rituximab formulation and the combination lowered the viscosity to a greater degree than either the S alone or no amino acid control, though both S and P alone lowered the viscosity of the Rituximab formulation to a greater extent than the no amino acid control.

Example 18

Formulation with Palivizumab

Palivizumab is a monoclonal antibody used in the prevention of respiratory syncytial virus infections. Palivizumab was formulated in single use vials as a sterile liquid formulation containing 0.5 mg/ml sodium chloride, 0.1 mg/ml glycine and 3.9 mg/ml histidine. The as tested Palivizumab final formulation concentration was 250 mg/ml. The ability of S and P to stabilize a Palivizumab formulation was evaluated by measuring the percent of aggregates by SEC-HPLC. As seen in FIG. 33, as the concentration of S increases from 2.5% (w/v) to 20% (w/v) in the formulation, the stability of the Palivizumab increased. The combination of S and P at increasing concentrations also stabilized Palivizumab and to a higher degree than serine alone. P alone stabilized Palivizumab, but to a lesser degree than either serine or the combination of S and P, but to a greater extent than the no amino acid added control.

As seen in FIG. 34, the addition of serine to a formulation containing P did not affect the ability of P to lower the viscosity of the Palivizumab formulation and the combination lowered the viscosity to a greater degree than either the S alone or no amino acid control, though both S and P alone lowered the viscosity of the Palivizumab formulation to a greater extent than the no amino acid control.

Example 19

Formulation of Rituximab

Rituximab is was formulated in single use vials as a sterile liquid formulation containing 10 mM sodium citrate buffer, 0.153 M sodium chloride, 0.1 M glycine and 0.07% polysorbate 80 at a pH of 6.5 and a Rituximab concentration of 5 mg/ml. For analysis, an additional amino acid was added to the Rituximab formulation with the tested formulation having a final Rituximab concentration of 10 mg/ml. The amino acids were added at a concentration of 3% (w/v). Each formulation was evaluated for 12 hours at 63° C. and evaluated for the percent of soluble aggregates by SE-HPLC at A650. Results are shown in FIG. 35. Based on the testing conducted, it was determined that the following amino acids provided the greatest degree of stability to the Rituximab protein following high temperature incubation, S, G, R, T, A, K and H, though P, V, Q, N, I, M, L, D, E, W and Y improved stability when compared to the Cetuximab formulation without any additional amino acid.

Unless otherwise defined, all technical and scientific terms used herein have the same meaning as commonly understood by one of ordinary skill in the art to which this disclosure belongs.

The disclosures illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure. The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A stable liquid pharmaceutical formulation comprising:
 an antibody, the antibody being adalimumab, alemtuzumab, alirocumab, basiliximab, bevacizumab, daratumumab, infliximab, panitumumab, ranibizumab, rituximab or trastuzumab;
 one or more amino acids to stabilize the antibody in the formulation, the one or more amino acids to stabilize the antibody including serine, threonine, alanine, glycine and valine and one or more further amino acids selected from the group consisting of isoleucine, asparagine, glutamine and aspartic acid; and
 one or more amino acids to reduce the viscosity of the formulation, the one or more amino acids to reduce viscosity of the formulation including proline,
 wherein the viscosity of the formulation is less than 100 cP.

2. The formulation of claim 1, wherein the one or more amino acids to stabilize the antibody are serine, threonine, alanine, glycine, valine and isoleucine.

3. The formulation of claim 1, wherein the one or more amino acids to stabilize the antibody are serine, threonine, alanine, glycine, valine and asparagine.

4. The formulation of claim 1, wherein the one or more amino acids to stabilize the antibody are serine, threonine, alanine, glycine, valine and glutamine.

5. The formulation of claim 1, wherein the one or more amino acids to stabilize the antibody are serine, threonine, alanine, glycine, valine and aspartic acid.

6. The formulation of claim 1, wherein the one or more amino acids to stabilize the antibody are serine, threonine, alanine, glycine, valine, glutamine and asparagine.

7. The formulation of claim 1, wherein the one or more amino acids to stabilize the antibody are serine, threonine, alanine, glycine, valine, glutamine and isoleucine.

8. The formulation of claim 1, wherein the one or more amino acids to stabilize the antibody are serine, threonine, alanine, glycine, valine, glutamine and aspartic acid.

9. The formulation of claim 1, wherein the one or more amino acids to stabilize the antibody are serine, threonine, alanine, glycine, valine, asparagine and isoleucine.

10. The formulation of claim 1, wherein the one or more amino acids to stabilize the antibody are serine, threonine, alanine, glycine, valine, asparagine and aspartic acid.

11. The formulation of claim 1, wherein the one or more amino acids to stabilize the antibody are serine, threonine, alanine, glycine, valine, isoleucine and aspartic acid.

12. The formulation of claim 1, wherein the one or more amino acids to stabilize the antibody and the one or more amino acids to reduce viscosity of the formulation are each present at a concentration of at least 0.1 mg/mL.

13. The formulation of claim 1, wherein the concentration of proline is from about 1 mg/mL to about 20 mg/mL and, when present in the formulation, the concentration of each of serine, threonine, glycine, alanine, valine, isoleucine and/or asparagine is from about 1 mg/mL to about 20 mg/mL.

14. The formulation of claim 1, wherein when present in the formulation, the concentration of each of glutamine and/or aspartic acid is from about 1.5 mg/mL to about 10 mg/mL.

15. The formulation of claim 14, wherein the concentration of each of serine and/or glycine is at least about 20 mg/mL.

16. The formulation of claim 13, wherein the concentration of each of serine, threonine, glycine, alanine, valine, and/or proline is at least 10 mg/mL.

17. The formulation of claim 13, wherein the concentration of isoleucine is at least 7 mg/mL.

18. The formulation of claim 13, wherein the concentration of asparagine is from about 3 mg/mL to about 8 mg/mL.

19. The formulation of claim 14, wherein the concentration of glutamine is from about 3 mg/mL to about 8 mg/mL.

20. The formulation of claim 15, wherein the concentration of each of serine and/or glycine is at least 25 mg/mL.

21. The formulation of claim 20, wherein the concentration of each of serine and/or glycine is at least 30 mg/mL.

22. The formulation of claim 21, wherein the concentration of serine is at least 35 mg/mL.

* * * * *